(12) United States Patent
Jiang

(10) Patent No.: US 9,169,296 B2
(45) Date of Patent: Oct. 27, 2015

(54) EXPRESSION AND ASSEMBLY OF HUMAN GROUP C ROTAVIRUS-LIKE PARTICLES AND USES THEREOF

(75)

(56) References Cited

OTHER PUBLICATIONS

Jiang, B. et al., Sequence conservation and expression of the gene encoding the outer capsid glycoprotein among human group C rotaviruses of global distribution, *Archives of Virology*, 141(2): 381-390, 1996.

Jiang, B. et al., Synthesis of Rotavirus-Like Particles in Insect Cells: Comparative and Quantitative Analysis, Biotechnology and Bioengineering, 60(3): 369-374, 1998.

Jiang, B. et al., Heterotypic protection from rotavirus infection in mice vaccinated with virus-like particles, Vaccine, 17: 1005-1013, 1999.

Kim, Y. et al., Production of hybrid double- or triple-layered virus-like particles of Group A and C rotaviruses using a baculovirus expression system, Virology, 302(1): 1-8, Oct. 10, 2002.

Lin, S.-C. et al., Expression and Assembly of Human Group C Rotavirus VLPs in Insect Cells, Poster, 10th Annual Meeting, Baculovirus and Insect Cell Culture, San Francisco, CA 2007.

Madore, H. et al., Biochemical and immunologic comparison of virus-like particles for a rotavirus subunit vaccine, Vaccine, 17(19): 2461-2471, May 14, 1999.

Moon, S. et al., First detection of group C rotavirus in children with acute gastroenteritis in South Korea, Clinical Microbiology and Infection, 1-4, 2010.

O'Neal, C. et al., Rotavirus Virus-Like Particles Administered Mucosally Induce Protective Immunity. Journal of Virology, 71(11): 8707-8717, 1997.

Sabara, M. et al., Assembly of Double-Shelled Rotaviruslike Particles by Simultaneous Expression of Recombinant VP6 and VP7 Proteins, Journal of Virology, 65(12): 6994-6997, 1991.

Steele, A.D. and V.L.A. James, Seroepidemiology of Human Group C Rotavirus in South Africa, Journal of Clinical Microbiology, 37(12): 4142-4144, 1999.

Vieira, H. et al., Triple layered rotavirus VLP production: kinetics of vector replication, mRNA stability and recombinant protein production, Journal of Biotechnology, 120(1): 72-82, Jul. 14, 2005.

Zeng, C. et al., Characterization and Replicase Activity of Double-Layered and Single-Layered Rotavirus-Like Particles Expressed from Baculovirus Recombinants, *Journal of Virology*, 70(5): 2736-2742, 1996.

Clark, K.B. et al., Synthesis and Characterization of Human Group C Rotavirus VLPs in Insect Cells, Abstract, 2008 Annual Meeting of the American Society for Virology, Ithaca, New York, 2008.

Tosser, G. et al., Expression of the Major Capsid Protein VP6 of Group C Rotavirus and Synthesis of Chimeric Single-Shelled Particles by Using Recombinant Baculoviruses, *Journal of Virology*, 66(10): 5825-5831, 1992.

Gonzalez, S. & J.L. Affranchino, Assembly of double-layered virus-like particles in mammalian cells by coexpression of human rotavirus VP2 and VP6, *Journal of General Virology*, 76:2357-2360, 1995.

Jiang, B. et al., Parental Rotavirus Vaccines, *Chinese Journal of Vaccines and Immunization*, 11:77-79, 2005.

Esona, M. et al., Molecular characterization of human rotavirus vaccine strain CDC-9 during sequential passages in Vero cells, *Human Vaccines*, 6(3): 1-7, Mar. 2010.

Jiang, B. et al., Rotavirus vaccines for global use, *Human Vaccines*, 6(5): 1-3, May 2010.

\* cited by examiner

Figure 5A

```
                 10         20         30         40         50         60         70         80
              ....|....|....|....|....|....|....|....|....|....|....|....|....|....|....|....|
ASP88         ................................................................................
Bristol       MISRNRRRNNQQKDIGKEKQLETIIDKEVKENKDSTKEDKLVVTEESNGDVTAVKEQSNNINLQKNDLVKEVMNIQNQTL
Cowden        MISRNRRRNNQQKNIEKEKQLETIINKEVKENKDSMKEDKLVVTEESNGDVTTAKEQSNNINLQKNDLVKEVMNIQNQTL
ASP88         MISRNRRRNTQQKDAEKEKQTENVEEKELKEAKEQVADEKQVITEENVDSPKDVKEQSNTVNLQKNDLVKEVINIQNQTL 90        100        110        120        130        140        150        160
              ....|....|....|....|....|....|....|....|....|....|....|....|....|....|....|....|
ASP88         NTVVAENKVEIEEIVKKYIPSYNTDSLIVKRLTEIQESSAKTYNTLFRLFTPVKSYLYDINGEKKLSTRWYWKLLKDDLP
Bristol       NTVVTENKVEIEEIVKKYIPSYNTDSLIVKLJTEIQESSAKTYNTLFRLFTPVKSYLYDINGEKKLSTRWYWKLLKDDLP
Cowden        NTIVAENKVEIEEVVKKYIPSYSTDKLIVKLJTEIQESSAKTYNKLFRLFTPVKSYLYDVNGEKKLSTRWYWKLLKDDLP 170        180        190        200        210        220        230        240
              ....|....|....|....|....|....|....|....|....|....|....|....|....|....|....|....|
ASP88         AGDYSVRQFFLSLYLNVLEGMPDYIMLRDMAVDNPYSAEAGKIVDGKSKEILVELYQDQMTEGYIRRYMSELRHKISGET
Bristol       AGDYSVRQFFLSLYLNVLEEMPDYIMLRDMAVDNPYSAEAGKIVDGKSKEILIELYQDQMTEGYIRRYMSELRHKISGET
Cowden        AGDYSVRQFFLSLYLNVLDEMPDYVMLRDMAVDNPYSAEAGKIVDEKSKEILVEIYQDQMTEGYIRRYMSDLRHISGET 250        260        270        280        290        300        310        320
              ....|....|....|....|....|....|....|....|....|....|....|....|....|....|....|....|
ASP88         NTAKYPAILHPVDNELNQYFLEHQLIQPLTTRNIAELIPTQLYHDPNYVFNIDAAFLTNSRFVPPYLTQDRIGLHDGFES
Bristol       NTAKYPAILHPVDNELNQYFLEHQLIQPLTTRNIAELIPTQLYHDPNYVFNIDAAFLTNSRFVPPYLTQDRIGLHDGFES
Cowden        NTAKYPAILHPVDNELNKYFLEHQLIQPLTTRNIAELIPTQLYHDPNYVFNIDAAFLTNSRFVPPYLTQDRIGLHDGFES 330        340        350        360        370        380        390        400
              ....|....|....|....|....|....|....|....|....|....|....|....|....|....|....|....|
ASP88         IWDSKTHADYVSARRFIPDLTELVDAEKQIKEMAAHLQLEAITTVQVESQFLAGISAAAANEAFKFIIGSVLSTRTIAVEF
Bristol       IWDSKTHADYVSARRFIPDLTELVDAEKQIKEMAAHLQLEAITTVQVESQFLAGISAAAANEAFKFIIGSVLSTRTIAVEF
Cowden        IWDAKTHADYVSARRFVPDLTELVDAEKQMKEMAAHLQLEAITTVQVESQFLAGISAAAANEAFKFIIGTVLSTRTIAVEF 410        420        430        440        450        460        470        480
              ....|....|....|....|....|....|....|....|....|....|....|....|....|....|....|....|
ASP88         ITSNYMSLASCMYLMTIMPSEIFLRESLVAMRLAIINTLIYPALGLAQMHYQAGEVRTPFELAEMRVANRSIRQWLHHCN
Bristol       ITSNYMSLASCMYLMTIMPSEIFLRESLVAMQLAIINTLIYPALGLAQMHYQAGEVRTPFELAEMQVANRSIRQWLHHCN
Cowden        ITSNYMSLASCMYLMTIMPSEIFLRESLVAMQLAVINTLTYPALGLAQMHYQAGEIRTPFELAEMQVANRPIRQWLHHCN
```

Figure 5B

```
               490        500        510        520        530        540        550        560
             ....|....|....|....|....|....|....|....|....|....|....|....|....|....|....|....|
ASP88        
Bristol      TLQFGRQITEGIIHLRFTNDIMTGRIVNLFSTMLVALSSQPFATYPLDYKRSVQRALQLLSNRTAQIADLTRLIVYNYTT
Cowden       TLQFGRQITEGIIHLRFTNDIMTGRIVNLFSTMLVALSSQPFATYPLDYKRSVQRALQLLSNRTAQIADLTRLIVYNYTT
             TLQFGRQVTEGVTHLRFTNDIMTGRIVNLFSTMLVALSSQPFATYPLDYKRSVQRALQLLSNRTAQIADLTRLIVYNYTT 570        580        590        600        610        620        630        640
             ....|....|....|....|....|....|....|....|....|....|....|....|....|....|....|....|
ASP88        
Bristol      LSACIVMNMHLVGTLTVERIQATSLTSLMMLISNKTVIPEPSSLFSYFSSNINFLTNYNEQIDNVVAEIMAAYRLNLYQQ
Cowden       LSACIVMNMHLVGTLTVERIQATSLTSLMMLISNKTVIPEPSSLFSYFSSNINFLTNYNEQIDNVVAEIMAAYRLNLYQQ
             LSACIVMNMHLVGTLTVERIQATALTSLIMLISNKTVIPEPSSLFSYFSSNINFLTNYNEQIDNVVAEIMAAYRLDLYQQ 650        660        670        680        690        700        710        720
             ....|....|....|....|....|....|....|....|....|....|....|....|....|....|....|....|
ASP88        
Bristol      KMLMLVTRFVSRLYIFDAPKIPPDQMYRLRLRNRLRNIPVERRRADVFFRIIMNNRDLIEKTSERICQGVLLSYTPMPLTYVE
Cowden       KMLMLVTRFVSKLYIFDAPKIPPDQMYRLRLRNRLRNIPVERRRADVFFRIIMNNRDLIEKTSERICQGVLLSYTPMPLTYVE
             LSACIVTRFVSRLYIFDAPKIPPDQMYRLRLRNRLRNIPVERRRADVFFRIIMNNRDLIEKTSERICQGVLLSYSPMPLTYVE 730        740        750        760        770        780        790        800
             ....|....|....|....|....|....|....|....|....|....|....|....|....|....|....|....|
ASP88        
Bristol      DVGLTNVINDTNNFQIINIEEIEKTGDYSAITNALLRDTPIILKGAIPYVTNSSVIDVLSKVDTTVFASIVKDRDISKLK
Cowden       DVGLTNVINDTNSFQIINIEEIEKTGDYSAITNALLRDTPIILKGAIPYVTNSSVIDVLSKVDTTVFASIVKDRDISKLK
             DVGLTNVVNDTNGFQIINIEEIEKTGDYSAITNALLRDTPIILKGAIPYVTNSSVIDVLSKIDTTVFASIVKDRDISKLK 810        820        830        840        850        860        870        880
             ....|....|....|....|....|....|....|....|....|....|....|....|....|....|....|....|
ASP88        
Bristol      PIKFIINSDSSEYYLVHNNKWTPTTTTAVYKARSQQFDIQHSVSMLESNLFFVVYNDLFKYIKTTTVLPINAVSYDGARI
Cowden       PIKFIINSDSSEYYLVHNNKWTPTTTTAVYKARSQQFDIQHSVSMLESNLFFVVYNDLFKYIKTTTVLPINAVSYDGARI
             PIKFTINSDSSEYYLVHNNKWTPTTTTAVYKARSQQFNIQHSVSMLESNLFFVVYNDLFKYIKTTTVLPINAVSYDGARI ASP88        MQET  (SEQ ID NO. 1)
Bristol      MQET  (SEQ ID NO. 16)
Cowden       MQET  (SEQ ID NO. 17)
```

Figure 6A

```
                    10         20         30         40         50         60         70         80
                    ....|....|....|....|....|....|....|....|....|....|....|....|....|....|....|....|
Bristol-VP2         GGCTTAAAAAGATCAGTTGAGGACAAATCGTTCAAGATGATAAGCAGAAACAGGCGCAGAAATAATCAACAAAAAAACAT
Asp88-VP2           ------------TCGAGGACAAATCGTCCAGATGATAAGCAAACAGGCGCAGAAATAACCAACAAAAAGATAT
Cowden-VP2          GGTTAAAAAGATCAATCGAGGACAAATCGTCCAAGATGATAAGCAGAAATAGACGTAGAAACACTCAACAGAAGATGC 90        100        110        120        130        140        150        160
                    ....|....|....|....|....|....|....|....|....|....|....|....|....|....|....|....|
Bristol-VP2         AGAAAAGAGAAACAATTAGAGACTATAATTAACAAAGAAGTTAAGGAAAACAAAGATTCTATGAAAGAAGATAAGCTAG
Asp88-VP2           AGGAAAAGAGAAACAATTAGAGACTATAATTGACAAAGAAGTAAAGGAAAACAAAGATTCTACAAAAGAAGATAAGCTAG
Cowden-VP2          TGAAAAGGAAAAGCAGAGACAGAGAAATGTGGAGGAGAAAGAGATAAAGGAAGCTAAAGAACAAGTTAAAGATGAAAAGCAAG 170        180        190        200        210        220        230        240
                    ....|....|....|....|....|....|....|....|....|....|....|....|....|....|....|....|
Bristol-VP2         TAGTTACAGAAGAAAGCAATGAGACGTCACAACTGCTAAAGAACAATCGAATATATTAATTTACAAAAGAATGATTTG
Asp88-VP2           TAGTTACGGAAGAAAGTAATGTGACGTCACGTCACAACTGCTAAAGAACAATCGAATATATTAATTTACAAAGAATGATTTG
Cowden-VP2          TGATTACAGAAGAAAACGTCGATAGTTCCTAAGGATGTTAAAGAACAATCAAACACCGTAAATCTACAAAAAAAATGACTTA 250        260        270        280        290        300        310        320
                    ....|....|....|....|....|....|....|....|....|....|....|....|....|....|....|....|
Bristol-VP2         GTTAAAGAAGTCATGATCATGAAATATACAGAATCAAACATTAAATACAGTAGTTACTGAGAATAAAGTTGAAATAGAAGAATAGT
Asp88-VP2           GTTAAAGAAGTCATGATCATGAATATACAGAATCAAACATTAAATACAGTAGTTGCTGAGAATAAAGTTGAAATAGAAGAAATAGT
Cowden-VP2          GTTAAAGAAGTTATAATATCCAAATCAAACATTGAATACAAATAGTTGCTGAGAATAAAGTTGAAATGGAAATTGAAGAAGTGGT 330        340        350        360        370        380        390        400
                    ....|....|....|....|....|....|....|....|....|....|....|....|....|....|....|....|
Bristol-VP2         TAAAAAATACATTCCATCATATATACTGATAGCCTCATTGTTAAAAAGTTAACTGAAATCCAGGAATCAAGTGCTAAAA
Asp88-VP2           TAAAAAATACATTCCCTCATATAATACTGACAGCCTTATTGTTAAAAAGTTAACTCAGGAATCCAGGAATCAAGTGCTAAAA
Cowden-VP2          TAAAAAGTATATTCCATCATCATCAACTGACACTCAACTCAAGCTAATAGTTAAAAATTAACTGAAATTCAAGAATCAAGTGCTAAAA 410        420        430        440        450        460        470        480
                    ....|....|....|....|....|....|....|....|....|....|....|....|....|....|....|....|
Bristol-VP2         CATTAATACATTGTTTAGATTATTTACTCCAGTTAAAAGTTATTTATAAGATATAATGGTGAGAAAAATTATCGACT
Asp88-VP2           CATATAATACATTATTCAGATTATTTACTCCAGTTAAAAGTTATTTATTATGACATAAATGGTGAGAAAAATTATCGACT
Cowden-VP2          CATACAATAAATTGTTTAGATTATTTACACCGGTTAAGAGTTATCTATAGATCTAATAGATCTAAATGAGAAGAGAAAAACTATCCACT
```

Figure 6B

```
                       490        500        510        520        530        540        550        560
                   ....|....|....|....|....|....|....|....|....|....|....|....|....|....|....|....|
Bristol-VP2        AGATGGTATTGGAAATTGCTCAAAGATGATTACCTGCTGGTGATTACTCAGTTAGACAATTCTTCCTGTCACTATATTT
Asp88-VP2          AGATGGTATTGGAAATTGCTCAAAGATGATTACCTGCTGGTGATTACTCAGTTAGACAATTCTTCCTGTCACTATATTT
Cowden-VP2         AGATGGTATTGGAAACTACTTAAGATGATCATCCTGGTGATTACTCAGTTAGACAATTCTTTCTATCTTTATACTT 570        580        590        600        610        620        630        640
                   ....|....|....|....|....|....|....|....|....|....|....|....|....|....|....|....|
Bristol-VP2        AAATGTTTTAGAGGAAATGCCCGATTACATAATGCTTCGTGATATGGCAGTGGATAACCATATTCAGCAGAAGCAGGTA
Asp88-VP2          AAATGTTTTAGAGGAAATGCCCGATTACATAATGCTTCGTGATATGGCAGTGGATAACCATATTCAGCAGAAGCAGGTA
Cowden-VP2         GAATGTATTAGATGAAGAAATGCCTGATTATGTTATGCTTCGTGATATGGCTGTGGATAATCCATATTCAGCAGAGGCAGGAA 650        660        670        680        690        700        710        720
                   ....|....|....|....|....|....|....|....|....|....|....|....|....|....|....|....|
Bristol-VP2        AAATCGTAGATGGAAAGTCTAAAGAATTTGATTGAACTATATCAAGACCAGATGACAGAAGGATATATTAGAAGATAT
Asp88-VP2          AAATCGTAGATGGAAAGTCTAAAGAATTTTAGTTGAACTATATCAAGACCAAATGACAGAAGGGTATATTAGAAGATAT
Cowden-VP2         AAATAGTAGATGAAAATCAAAAGAATCCTAGTAGAATATATATCAAGATCAAATGACTGAGGGTATATACGAAGATAT 730        740        750        760        770        780        790        800
                   ....|....|....|....|....|....|....|....|....|....|....|....|....|....|....|....|
Bristol-VP2        ATGTCTGAATTAAGACATAAAATATCTGGAGAGACATAATACTGCAAAATACCCAGCTATTCTACATCCCGTGGATAATGA
Asp88-VP2          ATGTCTGAATTAAGACATAAAATATCTGGAGAGACATAATACTGCAAAATACCCAGCTATTCTACATCCCGTGGATAATGA
Cowden-VP2         ATGTCTGATTGAGACATAGAATATCTGGTGAAACGAATACTGCTAAATATCCAGCTATTTTACATCCTGTAGATGAAGA 810        820        830        840        850        860        870        880
                   ....|....|....|....|....|....|....|....|....|....|....|....|....|....|....|....|
Bristol-VP2        ACTTAATCAATACTTTCTTGAGCATCAGTAATTCAACCATTAACTACAGGAACATTGCAGAATTGATTCAACCAAT
Asp88-VP2          GCTTAATCAATACTTTCTTGAGCATCAGTAATTCAACCATTAACTACAGGAACATTGCAGAATTGATTCAACCAAT
Cowden-VP2         ACTAAATAATACTTTCTTGAGCACCACCAACTGATTCAACCTGATTCAACTGATTCACTGACTACAGAAGAAATATAGCAGAATTAATTCAACTCAAT 890        900        910        920        930        940        950        960
                   ....|....|....|....|....|....|....|....|....|....|....|....|....|....|....|....|
Bristol-VP2        TATATCATGATCCAATTACGTTTTAATATTGATGCAGCCTTTTTAACAAATTCAAGATTTGTTCCACCATACTTAACA
Asp88-VP2          TATATCATGATCCAATTACGTTTTAATATTGATGCAGCCTTTTTAACAAATTCAAGATTTGTTCCACCATACTTAACA
Cowden-VP2         TGTATCATGATCCAAATTATGTGTTAACATTGATGCTGCATTTTTAGCAAACTCAAGATTTGTTCCACCGTATCTAACA
```

Figure 6C

```
                        970         980         990        1000        1010        1020        1030        1040
                   ....|....|....|....|....|....|....|....|....|....|....|....|....|....|....|....|
Bristol-VP2        CAGGATAGGATTGGATTACATGATGATGATTGAATCAATATGGGATTCAAAAACTCATGCTGATTACGTTTCAGCTAGAAG
Asp88-VP2          CAGGATAGGATTGGATTACATGATGATGATTCGAATCAATATGGGATTCAAAAACCCATGCTGATTACGTTTCAGCTAGAAG
Cowden-VP2         CAAGATAGAATTGGATTACATGATGATGATTGAGTGATTTGGATGCAAAACACATGCTGATTACGTTTCAGCTAGAAG 1050        1060        1070        1080        1090        1100        1110        1120
                   ....|....|....|....|....|....|....|....|....|....|....|....|....|....|....|....|
Bristol-VP2        ATTTATACCTGATTTAACTGAACTGGTGGTGGATGCTGAAAGCAAATAAAGAAATGGCTGCACATTTACAACTAGAGGCTA
Asp88-VP2          ATTTATACCTGATTTAACTGAACTGGTGGTAGATGCTGAAAGCAAATAAAGAAATGGCTGCACATTTACAACTAGAGGCTA
Cowden-VP2         ATTTGTACCTGATTTAACTGAGTTGATGCTGAGTGCTGAAAAACAGATGAAAGAAATGGCAGCACATTTACAGCTTGAAGCTA 1130        1140        1150        1160        1170        1180        1190        1200
                   ....|....|....|....|....|....|....|....|....|....|....|....|....|....|....|....|
Bristol-VP2        TTACGGTACAGTTGAATCACAATTTTTAGCAGGAATTAGTGCTGCTGCTGCGCAGCTAATGAAGCGTTAAATTTATAATTGGC
Asp88-VP2          TTACAGTACAGTTGAATCACAATTTTTAGCGGGAATTAGTGCTGCTGCGCAGCTAATGAAGCGTTCAAATTTATAATTGGC
Cowden-VP2         TTACAGTGCAAGTTGAATCACAATTCTTGGCAGGAATTAGTGCAGCGGCAGCTAATGAAGCATTAAGTTAAGTTATAATTGGT 1210        1220        1230        1240        1250        1260        1270        1280
                   ....|....|....|....|....|....|....|....|....|....|....|....|....|....|....|....|
Bristol-VP2        TCAGTTTTATCTACCAGAACAATAGCTGTAGAATTCATAACCTCAAACTATATGTCACTAGCATCATGTATGTATTTAAT
Asp88-VP2          TCAGTTTTATCTACCAGAACAATAGCTGTAGAATTCATAACCTCAAACTATATGTCGTTAGCATCATGTATGTATTTAAT
Cowden-VP2         ACTGTGCTGTCAACTAGAACAATAGCTAGAATTCATCACATCAAATTATATGTCATTAGCGTCATTAGCGTCATGTATGTATTTAAT 1290        1300        1310        1320        1330        1340        1350        1360
                   ....|....|....|....|....|....|....|....|....|....|....|....|....|....|....|....|
Bristol-VP2        GACTATTATGCCATCAGAGATTTTCTTAAGAGAATCATTAGTTGCTATGCAATTAGCAATAATAATAAATACCCTTATTTATC
Asp88-VP2          GACTATTATGCCATCAGAGATTTTCTTGAGAGAATCATTAGTTGCTATGCAATTAGCAATAATAATAAATACCCTTATTTATC
Cowden-VP2         GACGATTATGCCATCAGAATCTTTTGAGAGAATCGTTGCTAGTGCAATGCAGTTAGCAGTTAGCAGTAATAAATACTCTTACCTATC
```

Figure 6D

```
                    1370       1380       1390       1400       1410       1420       1430       1440
               ....|....|....|....|....|....|....|....|....|....|....|....|....|....|....|....|
Bristol-VP2    CAGCTCTAGGTTTAGCGCAAATGCATTATCAAGCAGGTGAAGTGAGGACTCCATTCGAATTAGCTGAAATGCAAGTAGCT
Asp88-VP2      CAGCTCTAGGTTTAGCGCAAATGCATTATCAAGCAGGTGAAGTGAGGACCCCATTCGAATTAGCTGAGATGCGAGTAGCT
Cowden-VP2     CAGCTTTAGGATTAGCACAAATGCATTATCAGGCAGGTGAAATAAGAACGCCCTTGAACTAGCAGAAATGCAAGTAGCA 1450       1460       1470       1480       1490       1500       1510       1520
               ....|....|....|....|....|....|....|....|....|....|....|....|....|....|....|....|
Bristol-VP2    AATAGATCTATTAGACAATGGTTACATCATTGTAATACACTTCAATTTGGTAGACAGATAACGAAGGGATAATTCATCT
Asp88-VP2      AATAGATCTATTAGACAATGGTTACATCATTGTAATACACTTCAATTTGGTAGACAGATAACGAAGGGATAATTCATCT
Cowden-VP2     AATAGGCCCATTAGGCAATGGTTGCATCATTGTAATACACTTCAATTTGGCAGACAGTAACTGAAGGAGTAACACATCT 1530       1540       1550       1560       1570       1580       1590       1600
               ....|....|....|....|....|....|....|....|....|....|....|....|....|....|....|....|
Bristol-VP2    ACGATTTACTAATGATATCATGACAGGCAGGATAGTAGTTATTTTCAACAATGTTAGTGGCTCTATCATCTCAGCCTT
Asp88-VP2      ACGATTTACTAATGATATCATGACAGGTAGGATAGTAGTTATTTTCAACAATGTTAGTGGCTTATCATCTCAGCCAT
Cowden-VP2     ACGGTTTACAAATGACATCATGACAGGTAGAATAGTAGTTAATCTCTTTCAACATGTGGTAGCTTATCATCTCAGCCTT 1610       1620       1630       1640       1650       1660       1670       1680
               ....|....|....|....|....|....|....|....|....|....|....|....|....|....|....|....|
Bristol-VP2    TCGCTACATATCCTTTAGACTATAAAAGATCTGTACAAAGAGCGTTACAACTTTTATCAAATAGAACAGCTCAAATAGCA
Asp88-VP2      TCGCTACATATCCTTTAGACTATAAAAGATCTGTACAAAGAGCATTACAACTTTATCAAATAGAACAGCCCAAATAGCA
Cowden-VP2     TTGCTACATATCCATTAGATTACAAAAGATCGTCCAGAGAGCATTACAGCATTACAGCTTCTTTCAAACAGGACTGCTCAAATAGCT 1690       1700       1710       1720       1730       1740       1750       1760
               ....|....|....|....|....|....|....|....|....|....|....|....|....|....|....|....|
Bristol-VP2    GATTAACCAGATTAAATAGTATACAATTATACTACATTATCGCTTGTATAGTTATGAATATGCATTAGTAGGAACTCT
Asp88-VP2      GATTAACCAGATTAAATAGTATACAATTATACTACATTATCGCATGTATAGTCATGTATAGTCATGAATATGCATTAGTAGGAACTCT
Cowden-VP2     GATTTGACTAGATTAAATAGTGTACAACTATACAACATTGTCAGCATGCATAGTCATGAACATGCATTGGTTGGAACCTT 1770       1780       1790       1800       1810       1820       1830       1840
               ....|....|....|....|....|....|....|....|....|....|....|....|....|....|....|....|
Bristol-VP2    TACTGTTGAACGTATACAGGCCACTTCTCTAACTTCTTTAATGATGTTAATCTCTAATAAGACAGTTATTCCGGAACCAT
Asp88-VP2      TACTGTTGAACGTATACAGGCCACTTCTCTAACTTCTTTAATGATGTTAATTTCTAATAAGACAGTTATTCCAGAACCAT
Cowden-VP2     AACTGTAGAACGTATACAAGCTACAGCTTAACTTCACTGATATCTGATAATAATGTTGATATCCAATAAAACGGTTATTCCAGAACCAT
```

Figure 6E

```
                   1850       1860       1870       1880       1890       1900       1910       1920
                   ....|....|....|....|....|....|....|....|....|....|....|....|....|....|....|....|
Bristol-VP2        CGTCTCTTTTTCATATTTCTCTAGTAACATTAATTTCTTACAAATTATAATTTCTTACAAATTGATAATGGTAGCAGAA
Asp88-VP2          CGTCTCTTTTTCATATTTCTCTAGTAACATTAATTTCTTACAAATTATAATTTCTTACAAATTGATAATGGTAGCAGAA
Cowden-VP2         CATCCCTCTTTTCATACTTTCTAGTAATATATTAATTTCTTGACAAACTACAATGAACAGATTGATAACGTAGTGGCTGAA 1930       1940       1950       1960       1970       1980       1990       2000
                   ....|....|....|....|....|....|....|....|....|....|....|....|....|....|....|....|
Bristol-VP2        ATAATGGCCGCATATAGATTGAATTTATATCAACAGAAAATGTTGATGCTCGTTACCCAGATTTGTGTCAAAGTTATACAT
Asp88-VP2          ATAATGGCCGCATATAGATTGAATTTATATCAACAGAAAATGTTGATGCTCGTTACCAGGTTTGTCAAGGTTGTACAT
Cowden-VP2         ATAATGGCAGCATACAGACTACGATCTATATCAACAGAAAATGCTAATGCTTGTTACTCAGTTGTTTCACGACTGTACAT 2010       2020       2030       2040       2050       2060       2070       2080
                   ....|....|....|....|....|....|....|....|....|....|....|....|....|....|....|....|
Bristol-VP2        ATTTGATGCTCCTAAGATACCACCAGATCAGATGTATAGATTAAGAAACCGATTAAGAAATATTCCAGTTGAAAGAAGAA
Asp88-VP2          ATTTGATGCTCCTAAAATACCGCCAGATCAGATGTATAGATTAAGAAACCGATTAAGAAATATTCCAGTTGAAAGAAGAA
Cowden-VP2         ATTTGATGCTCCTAAGATACCACCAGACCAGATGTATAGATTAAGAAATAGACTGAGGAACATTCCAGTTGAAAGAAGAA 2090       2100       2110       2120       2130       2140       2150       2160
                   ....|....|....|....|....|....|....|....|....|....|....|....|....|....|....|....|
Bristol-VP2        GAGCTGACGTATTCAGAATTATTATGAATATTAGAGATTTAATCGAAAAAACATCAGACGTATATGCCAGGGTGTGCTG
Asp88-VP2          GAGCTGATGTGTTCAGAATTATTATGAATATTAGAGATTTAATCGAAAAAACATCAGACATCAGACGTATATGTCAGGGTGTGTG
Cowden-VP2         GAGCAGAGTGTTCAGAGAATCATTATGAATAACAGAGATCTTATAGAGATAACAGAGAAACATCAGAAAACATCAGACGACCATTGTCAAGGAGTGTTA 2170       2180       2190       2200       2210       2220       2230       2240
                   ....|....|....|....|....|....|....|....|....|....|....|....|....|....|....|....|
Bristol-VP2        TTATCTTATACCAATGCCTTTAACTTACGTTGAAGATGTCGGGTTAACAAATGTAATTAATGACACTAATAGCTTTCA
Asp88-VP2          TTATCTTATACCAATGCCTTAACTTACGTTGAAGATGTCGGGTTAACAAATGTAATTAATGACACTAATAACTTCCA
Cowden-VP2         CTATCATTATCACCAATGCCATTAACATCATGTTGAGGAGTGGTTGTTGACAAATGTGGTTAATGACACTAATGGTTTTCA 2250       2260       2270       2280       2290       2300       2310       2320
                   ....|....|....|....|....|....|....|....|....|....|....|....|....|....|....|....|
Bristol-VP2        AATAATTAATATTGAAGAAATTGAAGAAGACCGTGACTATTCAGCTATAACGAATGCATTACTTCGGATACTCCAATCA
Asp88-VP2          AATAATTAATATTGAAGAAATTGAAGAAGACCGTGACTATTCAGCCATAACGAATGCATTACTTCGGATACTCCAATTA
Cowden-VP2         GATAATAAACATTGAAGAAATCGAGAAGACAGTGACTATTCAGCAATTACAAACGCATTACTCCGTGATGATACTCCAATCA
```

Figure 6F

```
                       2330       2340       2350       2360       2370       2380       2390       2400
                  ....|....|....|....|....|....|....|....|....|....|....|....|....|....|....|....|
Bristol-VP2       TATTGAAAGGTGCGATTCCATATGTTACTAACTCATCATCAGTAATTCATGTTTTATCTAAAGTGGACACCACAGTGTTCGCA
Asp88-VP2         TATTGAAAGGTGCGATTCCATATGTTACTAACTCATCATCAGTAATTCATGTTTTATCTAAAGTGGACACCACAGTGTTCGCA
Cowden-VP2        TACTGAAGGCGCTATTCCGTACGTTACCAATTCATCAGTAATAGATGTTCTATCTAAAATAGATACAACAGTGTTTGCG 2410       2420       2430       2440       2450       2460       2470       2480
                  ....|....|....|....|....|....|....|....|....|....|....|....|....|....|....|....|
Bristol-VP2       AGCATTGTAAAAGATAGGGACATTTCAAAGTTAAAACCAATAAAATTCATAATTAATTCAGATTCATCCGAATATTATTT
Asp88-VP2         AGCATCGTAAAAGATAGGGATATTTCAAAGTTAAAACCAATAAAATTCATAATTAATTCAGATTCATCCGAATATTATTT
Cowden-VP2        AGTATCGTTAAAGACAGAGATATTTCAAAATTCAAAATTAAAACCGATAAAATTCACAATTAATTCAGACTCATCAGAATACTATTT 2490       2500       2510       2520       2530       2540       2550       2560
                  ....|....|....|....|....|....|....|....|....|....|....|....|....|....|....|....|
Bristol-VP2       AGTACATAATAATAAATGACACCAACAACAACTACACAGCAGTATATAAAGCTAGATCTCAGCAATTTGATATACAACATT
Asp88-VP2         AGTACACAATAATAAATAAATGACACCAACAACAACTACAGCAGTATATAAAGCTAGATCTCAGCAATTTGATATACAACATT
Cowden-VP2        AGTATACAATAATAAATGACACAACAACAACAACTGCTGTGTACAAACCAGATCTCAGCAATTTATATACAACATT 2570       2580       2590       2600       2610       2620       2630       2640
                  ....|....|....|....|....|....|....|....|....|....|....|....|....|....|....|....|
Bristol-VP2       CAGTATCAATGCTAGAGTCAAACTTATTTTTGTGTATATAATGATTATTTAAATACATTAAAACCACTACAGTTCTG
Asp88-VP2         CAGTATCAATGCTAGAGTCAAACTTATTTTTTGTGTATATAATGATTATTTAAATACATTAAAACCACTACAGTTCTG
Cowden-VP2        CAGTGTCAATGTTAGAGTCAAACTTGTTCTTTGTTGTTATATAATGATCTGTTTAAGTACATCAAAACAACTACAGTATTA 2650       2660       2670       2680       2690       2700       2710       2720
                  ....|....|....|....|....|....|....|....|....|....|....|....|....|....|....|....|
Bristol-VP2       CCGATAAATGCTGTCTCCTATGACGGTGCAAGAATATGCAAGAAACATAAATGATTGTATAGTATCATCTTGTGACGAC
Asp88-VP2         CCGATAAATGCTGTCTCTCTATGATGGTGCAAGAATGGTGCAAGAATATGCAAGAAACATAAATGATTGTATAGTATCATCTTGTAACGAC
Cowden-VP2        CCAATCAATGCCGTGTCTATGATGGTGCGAGAATTATGCAGGAAACATGACTGATTAATTAATATATCATCTTGTGATGAC 2730
                  ....|....|...
Bristol-VP2       CTCAAACTTGTGGCT (SEQ ID No. 19)
Asp88-VP2         CTCAAACTCTGTGGCT (SEQ ID No. 18)
Cowden-VP2        CTCAAACTCTGTGGCT (SEQ ID No. 44)
```

Figure 7A

| Nucleotide | | | | | | | | |
|---|---|---|---|---|---|---|---|---|
| | * | 20 | * | 40 | * | 60 | * | 80 |
| S1/CDC | | | | | | | | : 80 |
| Bristol/UK | ..........................C.............G.................................. | | | | | | | : 80 |
| Jajeri/Nig | ..............................................G.............................. | | | | | | | : 80 |
| CMH004/TH | ...............A.............................................................. | | | | | | | : 80 |
| v508/India | ..........................................................C................... | | | | | | | : 80 |
| China | | | | | | | | : 80 |
| BCN6/Spain | ATGGATGTACTTTTTCTATAGCGAAAACTGTGTCAGATCTTAAAAAGAAAGTTGTAGTTGGAACAATTTATACTAATGT | | | | | | | : 80 |

| | * | 100 | * | 120 | * | 140 | * | 160 |
|---|---|---|---|---|---|---|---|---|
| S1/CDC | | | | | | | | : 160 |
| Bristol/UK | ...........................................A.................................. | | | | | | | : 160 |
| Jajeri/Nig | .....................................................T........................ | | | | | | | : 160 |
| CMH004/TH | .....................................................T........................ | | | | | | | : 160 |
| v508/India | ..................................G............................................ | | | | | | | : 160 |
| China | ........................C...................A...G............T................. | | | | | | | : 160 |
| BCN6/Spain | AGAAGATGTTGTACAACAGAATGATTGATTAGAACTTTGAATGAAATATTTTCATACTGGTGGCATTGGAACAC | | | | | | | : 160 |

| | * | 180 | * | 200 | * | 220 | * | 240 |
|---|---|---|---|---|---|---|---|---|
| S1/CDC | | | | | | | | : 240 |
| Bristol/UK | ......................C.................C...................................... | | | | | | | : 240 |
| Jajeri/Nig | ......................G........................................................ | | | | | | | : 240 |
| CMH004/TH | .....T.......................................C................................. | | | | | | | : 240 |
| v508/India | ..........................A..................................................... | | | | | | | : 240 |
| China | ..........C......................G.............................................. | | | | | | | : 240 |
| BCN6/Spain | AGCCTCAGAAGAGTGGAATTTTCAGTCACTACCACAATTGGGTACAACTTTATTAAAATTAGATGATAATTATGTTCAATCA | | | | | | | : 240 |

| | * | 260 | * | 280 | * | 300 | * | 320 |
|---|---|---|---|---|---|---|---|---|
| S1/CDC | | | | | | | | : 320 |
| Bristol/UK | ...C............................................................................ | | | | | | | : 320 |
| Jajeri/Nig | | | | | | | | : 320 |
| CMH004/TH | | | | | | | | : 320 |
| v508/India | | | | | | | | : 320 |
| China | | | | | | | | : 320 |
| BCN6/Spain | ACTAGAGGCATAATTGATTTTTATCATCTTTTTATAGAAGCTGTATGTGATGATGAAATTGTTAGAGAAGCTTCAAGAAA | | | | | | | : 320 |

Figure 7B

```
                       *        340         *        360         *        380         *        400
S1/CDC              : ............................................................................ : 400
Bristol/UK          : ............................................................................ : 400
Jajeri/Nig          : ............................................................................ : 400
CMH004/TH           : ............................................................................ : 400
v508/India          : ..........C................................................G............... : 400
China               : .........................................G.................................. : 400
BCN6/Spain          : TGGTATGCAACCTCAATCACCAGCTCTTATATTATTATCTTCATCAAAATTTAAAACAATTAATTTTAATAATAGTTCTC : 400

*        420         *        440         *        460         *        480
S1/CDC              : ............................................................................ : 480
Bristol/UK          : ..........T................................................................. : 480
Jajeri/Nig          : ............................................................................ : 480
CMH004/TH           : ..................................................T......................... : 480
v508/India          : ........................................................G................... : 480
China               : ..............................................A............G............... : 480
BCN6/Spain          : AATCTATCAAAAAATTGGAATGCTCTCAATCAGACGTGAGAATCCTGTATATGAGTACAAAAATCCAATGTTGTTTGAATAT : 480

*        500         *        520         *        540         *        560
S1/CDC              : .............................................................................T : 560
Bristol/UK          : .........G................................................................... : 560
Jajeri/Nig          : ............................................................................. : 560
CMH004/TH           : .....................................T..T................................... : 560
v508/India          : .................................................C......................... : 560
China               : ..............T.............................................................. : 560
BCN6/Spain          : AAAAAATTCTTATATTTTACAACGCGCAAATCCACAATTGGAAGCGTCATGGGTTTAAGATATATTATACAACAGTAATAC : 560

*        580         *        600         *        620         *        640
S1/CDC              : ............................................................................ : 640
Bristol/UK          : ............................................................................ : 640
Jajeri/Nig          : ....................................T..........A........................... : 640
CMH004/TH           : ............................................................................ : 640
v508/India          : ..................................G......................................... : 640
China               : ..........................T..............................A.T............... : 640
BCN6/Spain          : TTGTCAAATTGCAGCATTTGATTCCACCCTAGCTGAAATGCCAAACAATACGCAACGCTTCGTTTATATAATGGCAGAC : 640
```

Figure 7C

```
                         *         660         *         680         *         700         *         720
S1/CDC        :  ............................................................................................:  720
Bristol/UK    :  ..................C.........................................................................:  720
Jajeri/Nig    :  ............................................................................................:  720
CMH004/TH     :  .......................C....................................................................:  720
v508/India    :  ............................................................................................:  720
China         :  ..................C..............T..........................................................:  720
BCN6/Spain    :  TAAAAAGACCCATATCAAATGTTTAATGAAAATAGAAGCTGTGCTCCAAATATAAGCAACCAACTATTTTACTTGAT                    :  720

*         740         *         760         *         780         *         800
S1/CDC        :  ............................................................................................:  800
Bristol/UK    :  ............................................................................................:  800
Jajeri/Nig    :  .....................A...G...........................C..T..................................:  800
CMH004/TH     :  ............................................................................................:  800
v508/India    :  .....................A...............G.....................................................:  800
China         :  ............................................G........C.....................................:  800
BCN6/Spain    :                                         .A.................C..................................:  800
              :  CCTAATAATCAAACAACTTGGCTTTTTAATCCGGTACAATTAATGAACATTACCATTGAATTCTATAATAATGG                      :  800

*         820         *         840         *         860         *         880
S1/CDC        :  ............................................................................................:  880
Bristol/UK    :  ............................................................................................:  880
Jajeri/Nig    :  ............................................................................................:  880
CMH004/TH     :  ............................................................................................:  880
v508/India    :  ...........................C.............................................A.................:  880
China         :  ....................................G.......................................................:  880
BCN6/Spain    :  TCAACTAATTGATATGCTTCGAAATATGGGAATAGTTACTGTAAGAACTTTGATTCTTATAGAATAACAATTGACATGA                 :  880

*         900         *         920         *         940         *         960
S1/CDC        :  ............................................................................................:  960
Bristol/UK    :  ............................................................................................:  960
Jajeri/Nig    :  ............................................................................................:  960
CMH004/TH     :  ..................C.........................................................................:  960
v508/India    :  ..........................A....C...........................................................:  960
China         :  ........G..........................C.......................................................:  960
BCN6/Spain    :  TTAGACCAGCTGCTATGACTCAATACGTTCAACGAATTTTCCACAAGGTGGACCTATCATCATTTCAGGCTACATATATG                :  960
```

Figure 7D

```
              *         980         *        1000         *        1020         *        1040
S1/CDC      : ............................................................................ : 1040
Bristol/UK  : .................T......................G................................... : 1040
Jajeri/Nig  : ..........................A................................................. : 1040
CMH004/TH   : ............................................................................ : 1040
v508/India  : .....G...................T.........................C........................ : 1040
China       : ........................................G................................... : 1040
BCN6/Spain  : TTAACATTAAGTATATTAGATGCTACCACAGAGTCCGTTCTATGTGATTCTCATTCAGTAGAATATTCAATAGTAGCAAA : 1040

*        1060         *        1080         *        1100         *        1120
S1/CDC      : ............................................................................ : 1120
Bristol/UK  : ...T........................................................................ : 1120
Jajeri/Nig  : ..........A..................A.............................................. : 1120
CMH004/TH   : ............................................................................ : 1120
v508/India  : .................................C.......................................... : 1120
China       : .....................................................T...................... : 1120
BCN6/Spain  : ...T................A....................................................... : 1120
              CGTCAGAAGAGATTCAGCGATGCCAGCTGGAACTGTTTTCAACGGGATTCCATGGGAACACACTATCCAATTACA

*        1140         *        1160         *        1180         *
S1/CDC      : ..................................................................  : 1185 (SEQ ID No. 31)
Bristol/UK  : ...........................T......................................  : 1185 (SEQ ID No. 25)
Jajeri/Nig  : ...................G..............................................  : 1185 (SEQ ID No. 26)
CMH004/TH   : ..................................................................  : 1185 (SEQ ID No. 27)
v508/India  : ..................................................................  : 1185 (SEQ ID No. 28)
China       : ..................................................................  : 1185 (SEQ ID No. 29)
BCN6/Spain  : ...........................T......................................  : 1185 (SEQ ID No. 30)
              CTGTTGCTCAAGAAGATAATTTAGAAAGATTATTGTTAATCGCATCTGTGAAGAGAATGGTAATG            (SEQ ID No. 41)
```

Figure 8A

Amino Acid

```
                        *        20         *        40         *        60         *        80
S1/CDC       : ................................................................................ :  81
Bristol/UK   : ..............E................................................................. :  81
JajeriNig    : ............................................Y................................... :  81
CMH004/TH    : ......................................................H........................ :  81
v508/India   : ..............................................V................................. :  81
China        : ..............................................V................................. :  81
BCN6/Spain   : MDVLFSIAKTVSDLKKKVVVGTIYTNVEDVVQQTNELIRTLNGNIFHTGGIGTQPQKEWNFQLPQLGTTLLNLDDNYVQST :  81

*       100         *       120         *       140         *       160
S1/CDC       : ................................................................................ : 162
Bristol/UK   : ................................................................................ : 162
JajeriNig    : ..............................................................V................. : 162
CMH004/TH    : ................................................................................ : 162
v508/India   : ...................................L............................................ : 162
China        : ................................................................................ : 162
BCN6/Spain   : RGIIDFLSSFIEAVCDDEIVREASRNGMQPQSPALILLSSSKFKTINFNNSSQSIKNWNAQSRRENPVYEYKNPMLFEYKN : 162

*       180         *       200         *       220         *       240
S1/CDC       : ................................................................................ : 243
Bristol/UK   : ................................................................................ : 243
JajeriNig    : ...............I................................................................ : 243
CMH004/TH    : ................................................................................ : 243
v508/India   : ................................................................................ : 243
China        : .............I.................................................................. : 243
BCN6/Spain   : SYILQRANPQFGSVMGLRYYITSNTCQIAAFDSTLAENAPNNTQRFYNGRLKRPISNVLMKIEAGAPNISNPTILPDPNN : 243

*       260         *       280         *       300         *       320
S1/CDC       : ................................................................................ : 324
Bristol/UK   : ................................................................................ : 324
JajeriNig    : ................................................................................ : 324
CMH004/TH    : ...............................I................................................ : 324
v508/India   : ................................................................................ : 324
China        : ..................................................R.....Q....................... : 324
BCN6/Spain   : QTTWLFNPVQLMNGTFTIEFYNNGQLIDMVRNMGIVTVRTFDSYRITIDMIRPAAMTQVVQRIFPQGGPYHFQATYMLTLS : 324
```

Figure 8B

```
                    *         340         *         360         *         380         *
S1/CDC       : ............................................................................ : 395 (SEQ ID No. 32)
Bristol/UK   : ............................................................................ : 395 (SEQ ID No. 35)
JajeriNig    : ............................................................................ : 395 (SEQ ID No. 36)
CMH004/TH    : ............................................................................ : 395 (SEQ ID No. 37)
v508/India   : ............................................................................ : 395 (SEQ ID No. 38)
China        : ....................................................T....................... : 395 (SEQ ID No. 39)
BCN6/Spain   : ILDATTESVLCDSHSVEYSIVANVRRDSAMPAGTVFQPGFPWEHTLSNYTVAQEDNLERLLLIASVKRMVM         : 395 (SEQ ID No. 40)
                                                                  (SEQ ID No. 24)
```

Figure 9A

```
              10         20         30         40         50         60         70         80
              ....|....|....|....|....|....|....|....|....|....|....|....|....|....|....|....|
S-1_VP6       ATCTCATTCACAATGGATGTACTTTTTTCTATAGCGAAAACCGTGTCAGAATCTTAAAGAGAAAGTTGTAGTTGGAACAAT 90        100        110        120        130        140        150        160
              ....|....|....|....|....|....|....|....|....|....|....|....|....|....|....|....|
S-1_VP6       TTATACTAAATGTAGAAAGATGTTGTACAACAGACAATGAATTGATTAGAACTTTGAATGGAAATATTTTCAATACTGTG 170        180        190        200        210        220        230        240
              ....|....|....|....|....|....|....|....|....|....|....|....|....|....|....|....|
S-1_VP6       GCATTGGAACACAGCCTCAGAAAGAGTGGAATTTTCAGCTCCACCACTTTATTAAATTTAGATGATAAT 250        260        270        280        290        300        310        320
              ....|....|....|....|....|....|....|....|....|....|....|....|....|....|....|....|
S-1_VP6       TATGTTCAATCAACTAGAGGCATAATTGATTTTTTATCATCTTTTATGAAGAAGCTGTATGTGATGAATGAATTGTTAGAGA 330        340        350        360        370        380        390        400
              ....|....|....|....|....|....|....|....|....|....|....|....|....|....|....|....|
S-1_VP6       AGCTTCAAGAAATGGTATGCAACCTCAATCACCAGCTCTCTATATTATTATCTTCATCAAAATTTAAAACAATTAATTTTA 410        420        430        440        450        460        470        480
              ....|....|....|....|....|....|....|....|....|....|....|....|....|....|....|....|
S-1_VP6       ATAATAGTTCTCAATCTATCAAAAATTGGAATGCTCAATCAAGACGTGAGAATCCTGTATATGAGTACAAAAATCCAATG 490        500        510        520        530        540        550        560
              ....|....|....|....|....|....|....|....|....|....|....|....|....|....|....|....|
S-1_VP6       ATAATATATAAAAATTCTTATATTTTACAACAACGCGCAAATCCACAATTTGGAAGCGTCATGGGTTTAAGATATTATAC 570        580        590        600        610        620        630        640
              ....|....|....|....|....|....|....|....|....|....|....|....|....|....|....|....|
S-1_VP6       TTCTTTGAATATAAAAATTGTCAAATTGCAGCATTTGAATTCCACCCTAGCTGAAAATGCACCAAATATAACGCAAGCTTCGTTT 650        660        670        680        690        700        710        720
              ....|....|....|....|....|....|....|....|....|....|....|....|....|....|....|....|
S-1_VP6       AACAAGTAAATATTTGTCAAATAGACCCATAATCAAATGTTTAATGAAAATAGAAGCTGTGCTCCAAATATAAGCAACCAAGACT

730
              ....|....
S-1_VP6       ATAATGGCAGACTAAAAGA
```

Figure 9B

```
               730         740        750        760        770        780        790        800
            ....|....|....|....|....|....|....|....|....|....|....|....|....|....|....|....|
S-1_VP6     ATTTTACCTGATCCTAATAATCAAACAACTTGGCTTTTTAATCCGGTACAATTAATGAATGGAAGATTACCATTGAATT 810        820        830        840        850        860        870        880
            ....|....|....|....|....|....|....|....|....|....|....|....|....|....|....|....|
S-1_VP6     CTATAATAATGGTCAACTAATTGATATGGTTCGAAATATGGGAATAGTTACTGTAAGAACTTTTGATTCTTATAGAATAA 890        900        910        920        930        940        950        960
            ....|....|....|....|....|....|....|....|....|....|....|....|....|....|....|....|
S-1_VP6     CAATTGACATGATTAGACCAGCTGCTATGACTCAATACGTTCAACGAATTTTCCACAAGGTGGACCTTATCATTTTCAG 970        980        990       1000       1010       1020       1030       1040
            ....|....|....|....|....|....|....|....|....|....|....|....|....|....|....|....|
S-1_VP6     GCTACATATATGTTAACATTAAGTATATTAGATGCTACCACAGAGTCCGTTCTATGTGATTCTCATTCAGTAGAATATTC 1050       1060       1070       1080       1090       1100       1110       1120
            ....|....|....|....|....|....|....|....|....|....|....|....|....|....|....|....|
S-1_VP6     AATAGTAGCAAACGTCAGAGAGATTCAGCAATGCCAGCTGGAACTGTTTTTCAACCGGGATTCCATGGGAACACACAC 1130       1140       1150       1160       1170       1180       1190       1200
            ....|....|....|....|....|....|....|....|....|....|....|....|....|....|....|....|
S-1_VP6     TATCCAATTACACTGTTGCTCAAGAAGATAATTTAGAAAGATTATTGTTAATCGCATCTGTGAAGAGAATGGTAATGTAG 1210       1220       1230       1240       1250       1260       1270       1280
            ....|....|....|....|....|....|....|....|....|....|....|....|....|....|....|....|
S-1_VP6     ATAAGCTAGAAGACTAAACATCTTCTATGCGGCCTACATACCATGTAGCATGAATCACGACTGGGTTTAGTCCATGCTCG 1290       1300       1310       1320       1330       1340
            ....|....|....|....|....|....|....|....|....|....|....|....|....
S-1_VP6     CATAGGGCAAATATGCATGATATGGATGATCCCCAGAAGGATGAAATGTGAACTATGTGGCT (SEQ ID No. 46)
```

```
                       570        580        590        600        610        620        630        640
                  ....|....|....|....|....|....|....|....|....|....|....|....|....|....|....|....|
Bristol-VP6_X59843 GATATTATACAACAAGTAATACTTGTCAAATTGTCAGCATTTGATTCCACCCTAGCTGAAAATGCACCAAACAATACACAA
S-1_VP6            GATATTATACAACAAGTAATACTTGTCAAATTGTCAGCATTTGATTCCACCCTAGCTGAAAATGCACCAAATAATACGCAA 650        660        670        680        690        700        710        720
                  ....|....|....|....|....|....|....|....|....|....|....|....|....|....|....|....|
Bristol-VP6_X59843 CGCTTCGTTTATAATGGCAGACTAAAAAGACCCATATCAAACGTTTAATGAAAATAGAAGCTGGTGCTCCAAATATAAG
S-1_VP6            CGCTTCGTTTATAATGGCAGACTAAAAAGACCCATATCAAACGTTTAATGAAAATAGAAGCTGGTGCTCCAAATATAAG 730        740        750        760        770        780        790        800
                  ....|....|....|....|....|....|....|....|....|....|....|....|....|....|....|....|
Bristol-VP6_X59843 CAACCCAACTATTTTACCTGATCCTAATAATAATCAAACAACTTGGCTTTTTAATCCGTACAATTAATGAATGGAACATTTA
S-1_VP6            CAACCCAACTATTTTACCTGATCCTAATAATAATCAAACAACTTGGCTTTTTAATCCGTACAATTAATGAATGGAACATTTA 810        820        830        840        850        860        870        880
                  ....|....|....|....|....|....|....|....|....|....|....|....|....|....|....|....|
Bristol-VP6_X59843 CCAATTGAATTCTATAATGTCAACTAATTGATAATGGTTCGAAATATGGAATAGTTACTGTAAGAACTTTTGATTCT
S-1_VP6            CCAATTGAATTCTATAATGTCAACTAATTGATAATGGTTCGAAATATGGAATAGTTACTGTAAGAACTTTTGATTCT 890        900        910        920        930        940        950        960
                  ....|....|....|....|....|....|....|....|....|....|....|....|....|....|....|....|
Bristol-VP6_X59843 TATAGAATAACAATTGACATGATTAGACCAGCTGCTATGACTCAATACGTTCAACGAATTTTCCACAAGGTGGACCTTA
S-1_VP6            TATAGAATAACAATTGACATGATTAGACCAGCTGCTATGACTCAATACGTTCAACGAATTTTCCACAAGGTGGACCTTA 970        980        990        1000       1010       1020       1030       1040
                  ....|....|....|....|....|....|....|....|....|....|....|....|....|....|....|....|
Bristol-VP6_X59843 TCATTTTCAGGCTACATATATGTTAACATTAAGTATATTAGATGCTACCACAGAGTCCGTTCTATGTGATTCTCATTCAG
S-1_VP6            TCATTTTCAGGCTACATATATGTTAACATTAAGTATATTAGATGCTACCACAGAGTCCGTTCTATGTGATTCTCATTCAG 1050       1060       1070       1080       1090       1100       1110       1120
                  ....|....|....|....|....|....|....|....|....|....|....|....|....|....|....|....|
Bristol-VP6_X59843 TGGAATATTCAATAGTAGCAAACGTTAGAGAGAGATTCAGCGATGCCAGCTGAACTGTTTTTCAACCGGGATTCCATGG
S-1_VP6            TAGAATATTCAAATAGTAGCAAACGTCAGAAGAGATTCAGCAATGCCAGCTGGAACTGTTTTTCAACCGGGATTCCATGG
```

Figure 10C

```
                         1130      1140      1150      1160      1170      1180      1190      1200
                    ....|....|....|....|....|....|....|....|....|....|....|....|....|....|....|....|
Bristol-VP6_X59843  GAACACACACTATCCAATTACACTGTTGCTCAAGAAGATAAATTAGAAAGATTAATTGTTAATTGCATCTGTGAAGAGAAT
S-1_VP6             GAACACACACTATCCAATTACACTGTTGCTCAAGAAGATAAATTAGAAAGATTATTGTTAATCCATCTGTGAAGAGAAT 1210      1220      1230      1240      1250      1260      1270      1280
                    ....|....|....|....|....|....|....|....|....|....|....|....|....|....|....|....|
Bristol-VP6_X59843  GGTAATGTAGAGATAAGCTAGAGGGCTAAACATCTTCTATGCGGCCTACATACCATGTAGCATGAATCACGACTGGGTTTAG
S-1_VP6             GGTAATGTAGAGATAAGCTAGAAGACTAAACATCTTCTATGCGGCCTACATACCATGTAGCATGAATCACGACTGGGTTTAG 1290      1300      1310      1320      1330      1340      1350
                    ....|....|....|....|....|....|....|....|....|....|....|....|....|....|
Bristol-VP6_X59843  TCCATGCTTGCATAGGGGCAAATATGCAATGATATGATGATGATCCCAAGAAGGATGAAATGAACTATGTGGCT  (SEQ ID No. 47)
S-1_VP6             TCCATGCTCGCATAGGGGCAAATATGCAATGATATGCATGATGATCCCCAGAAGGATGAAATGAACTATGTGGCT  (SEQ ID No. 46)
```

EXPRESSION AND ASSEMBLY OF HUMAN GROUP C ROTAVIRUS-LIKE PARTICLES AND USES THEREOF

REFERENCE TO RELATED APPLICATIONS

This application claims priority from U.S. Provisional Patent Application Ser. No. 61/130,615 filed May 29, 2008 and U.S. Provisional Patent Application Ser. No. 61/111,425 filed Nov. 5, 2008, the entire content of both are incorporated herein by reference.

GOVERNMENT SPONSORSHIP

This invention was made by the Centers for Disease Control and Prevention, an agency of the United States Government.

FIELD OF THE INVENTION

The present invention relates to group C rotaviruses (GpC RV) and rotavirus-like particles, methods of producing immunogenic rotavirus-like particles, immunogenic compositions inclusive of rotavirus-like particles and methods for eliciting an immune response using compositions inclusive of rotavirus-like particles, as well as producing a diagnostic for rotavirus infection.

BACKGROUND OF THE INVENTION

Rotaviruses are a diverse set of pathogens classified into groups A through G based on the distinct characteristics of the inner capsid protein, VP6. Among these, GpC RV has been identified as a pathogen in humans and attributed to outbreaks and sporadic cases of gastroenteritis worldwide in young children <3 years of age (8, 13, 15, 25, 26, 29, 30) and in older children and adults (2, 15, 20, 21, 25, 26, 30, 32). While some studies have reported low detection rates in children with diarrhea (1, 2, 4, 26, 29), seroprevalence studies have demonstrated that GpC RV is a commonplace pathogen with a much higher occurrence in adults (4, 6, 10, 20, 27, 31).

One possible cause of low GpC RV detection is the unavailability of adequate diagnostic tools. While PCR is a frequently employed technique, it is often insensitive for diagnosis of GpC RV due to the instability of its capsid proteins and the degradation of its RNA genome. It is also not an accessible technique to many clinical laboratories that are involved in diagnostics of samples from patients with gastroenteritis. If a more practical and economical tool, like a GpC RV-specific enzyme immunoassay (EIA), was available, testing of large numbers of samples could be performed to better estimate GpC RV disease burden. Propagation of the Cowden strain, a prototype porcine GpC RV, has been successful and antibodies to this virus have been employed for GpC RV diagnostics (13, 28, 30, 33, 34). However their specificity and sensitivity to human GpC RV is questionable. Progress in the development of a sensitive and specific EIA for human GpC RV has been stunted by its fastidious growth in cell culture. To circumvent the prior art problems of GpC RV fastidious growth problem, VP6 from a human GpC RV was expressed in insect cells using the Baculovirus System and antibody to this recombinant protein was employed in seroprevalence studies (6, 11, 31). To the best of our knowledge, these reagents have not been utilized for viral detection in human specimens and their specificity to GpC RV remains questionable.

GpC RV are a cause of acute gastroenteritis in children and adults that is distinct from group A RV. Human group A RV detection methods are well established and widely available while group C RV diagnostics are only available in a few reference laboratories. Since native human group C RV are unstable and cannot be grown in cell culture, reagents from animal group C RV have been used for diagnostics. However these diagnostic tools may not be sensitive or specific enough for human strains. Thus, sensitive and specific detection methods and reagents for human group C RV are not readily available. Consequently, the burden of GpC RV disease has not been clearly established.

Thus, there exists a need for a human specific group C rotavirus diagnostic. There also exists a need for a human group C RV-like particle for use in such a diagnostic and for eliciting an immune response as a vaccine.

SUMMARY OF THE INVENTION

An isolated recombinant human rotavirus group C virus-like particle including human rotavirus group C VP6 protein and a human rotavirus group C VP7 protein is provided according to embodiments of the present invention. In further embodiments, an isolated recombinant human rotavirus group C virus-like particle including human rotavirus group C VP6 protein, a human rotavirus group C VP7 protein and a human rotavirus group C VP2 protein is provided. According to certain embodiments, the isolated recombinant human rotavirus group C virus-like particles of the present invention are free of other human rotavirus group C proteins such as VP1, VP3, VP4, NSP1, NSP2, NPS3, NSP4, NSP5, NSP6 and NSP7.

Isolated recombinant human rotavirus group C virus-like particles are provided according to embodiments of the present invention which include human rotavirus group C VP6 protein including the amino acid sequence of SEQ ID No. 32. Isolated recombinant human rotavirus group C virus-like particles are provided according to embodiments of the present invention which include human rotavirus group C VP7 protein including the amino acid sequence of SEQ ID No. 34. In particular embodiments, isolated recombinant human rotavirus group C virus-like particles are provided according to embodiments of the present invention which include human rotavirus group C VP6 protein including the amino acid sequence of SEQ ID No. 32 and human rotavirus group C VP7 protein including the amino acid sequence of SEQ ID No. 34.

Isolated recombinant human rotavirus group C virus-like particles are provided according to embodiments of the present invention which include the human rotavirus group C VP2 protein including the amino acid sequence of SEQ ID No. 1. In further embodiments, isolated recombinant human rotavirus group C virus-like particles are provided according to embodiments of the present invention which include human rotavirus group C VP6 protein including the amino acid sequence of SEQ ID No. 32, human rotavirus group C VP7 protein including the amino acid sequence of SEQ ID No. 34 and human rotavirus group C VP2 protein including the amino acid sequence of SEQ ID No. 1.

Processes for detection of a human rotavirus group C antibody in a biological sample are provided according to embodiments of the present invention which include contacting a first biological sample with a plurality of isolated recombinant human rotavirus group C virus-like particles and detecting the formation of a complex between an anti-human rotavirus group C antibody present in the first biological sample and the plurality of isolated recombinant human rotavirus group C virus-like particles, to obtain a first signal indicative of the presence of an anti-human rotavirus group C antibody.

Anti-human rotavirus group C vaccines are provided according to embodiments of the present invention which includes isolated recombinant human rotavirus group C virus-like particles admixed with a pharmaceutically acceptable carrier.

Processes of delivering a cargo moiety to a cell are provided according to embodiments of the present invention which include introducing a cargo moiety into an internal space defined by an isolated recombinant human rotavirus group C virus-like particle and contacting the isolated recombinant human rotavirus group C virus-like particle and a cell.

Exemplary cargo moieties are a label, an antigen, a nucleic acid sequence encoding a protein or peptide, and a therapeutic agent.

Anti-human rotavirus group C antibody assay kits are provided according to embodiments of the present invention which include isolated recombinant human rotavirus group C virus-like particles and at least one ancillary reagent. Optionally, the virus-like particles are attached to a solid substrate.

Immunogenic compositions are provided according to embodiments of the present invention which include an isolated recombinant human rotavirus group C virus-like particle described herein and a pharmaceutically acceptable carrier. Optionally, an inventive immunogenic composition includes an immunological adjuvant.

Processes of generating an immunological response in a human including administering an immunogenic composition including an inventive human rotavirus group C virus-like particle to a human are provided according to embodiments of the present invention. Optionally, an inventive process includes administering the immunological composition to a mucosal surface.

An isolated polypeptide including an amino acid sequence of: a) an amino acid sequence having at least 98% to the amino acid sequence set forth in SEQ ID NO: 1 (ASP88 VP2 amino acid sequence); b) an amino acid sequence having at least 99% to the amino acid sequence set forth in SEQ ID NO: 1 (ASP88 VP2 amino acid sequence); c) an amino acid sequence set forth in SEQ ID NO: 1 (ASP88 VP2 amino acid sequence); or d) an amino acid sequence set forth in SEQ ID NO: 32 (S 1 VP6 amino acid sequence) is provided according to embodiments of the invention. An isolated nucleic acid molecule including a nucleotide sequence encoding the isolated polypeptide including an amino acid sequence of: a) an amino acid sequence having at least 98% to the amino acid sequence set forth in SEQ ID NO: 1 (ASP88 VP2 amino acid sequence); b) an amino acid sequence having at least 99% to the amino acid sequence set forth in SEQ ID NO: 1 (ASP88 VP2 amino acid sequence); c) an amino acid sequence set forth in SEQ ID NO: 1 (ASP88 VP2 amino acid sequence); or d) an amino acid sequence set forth in SEQ ID NO: 32 (S 1 VP6 amino acid sequence) is provided according to embodiments of the invention.

Immunogenic compositions are provided according to embodiments of the present invention including a polypeptide including at least one amino acid sequence of any of SEQ ID NOS: 1-13 wherein said amino sequence is an antigenic epitope recognized by an antibody. Optionally, such an immunogenic composition further includes a rotavirus-like particle described herein.

An antibody is provided according to embodiments of the present invention that is specific for a group C rotavirus and which does not recognize a group A rotavirus. In particular embodiments, an antibody according to embodiments of the present invention is specific for an amino acid sequence of any of SEQ ID NOS: 3-13 and does not recognize a group A rotavirus.

An isolated polypeptide is provided according to embodiments of the present invention that includes at least one amino acid sequence of SEQ ID NO: 3 or 8. An isolated nucleic acid molecule including a nucleotide sequence encoding the isolated polypeptide that includes at least one amino acid sequence of SEQ ID NO: 3 or 8 is provided according to embodiments of the present invention.

Vectors including an isolated nucleic acid molecule including a nucleotide sequence encoding the isolated polypeptide that includes at least one amino acid sequence of SEQ ID NO: 3 or 8 are provided according to embodiments of the present invention. Isolated host cells including a vector of the present invention are provided according to particular embodiments.

Processes of forming a human group C rotavirus-like particle are provided according to embodiments of the present invention which include constructing a first vector comprising a nucleic acid molecule comprising a sequence encoding a human group C rotavirus VP6 capsid protein operably linked to a promoter that drives expression of said protein in an insect cell; constructing a second vector comprising a nucleic acid molecule comprising a sequence encoding a human group C rotavirus VP7 capsid protein operably linked to a promoter that drives expression of said protein in an insect cell; and infecting an insect cell culture with said first and second baculovirus vector under conditions that promote expression of the VP6 capsid protein and VP7 capsid protein and association to form the human group C rotavirus-like particle. In further embodiments, processes of forming a human group C rotavirus-like particle include constructing a third vector comprising a nucleic acid molecule comprising a sequence encoding a human group C rotavirus VP2 core protein operably linked to a promoter that drives expression of said protein in an insect cell; and infecting an insect cell culture with said first baculovirus vector, second baculovirus vector, and third baculovirus vector under conditions that promote expression of the VP6 capsid protein, and VP7 capsid protein and said VP2 core protein.

BRIEF DESCRIPTION OF THE DRAWINGS

FIGS. 5A-5B show an amino acid sequence alignment for Group C rotavirus VP2 proteins from human strain ASP88 (SEQ ID NO: 1); "Bristol" human strain (SEQ ID NO: 16, Accession CAC 44890) and "Cowden" porcine strain (SEQ ID NO: 17, Accession M74217);

FIGS. 6A-6F show a nucleotide sequence alignment of sequences encoding human Group C VP-2 for inventive strain ASP88 (SEQ ID NO: 18), "Cowden" porcine strain (SEQ ID No. 44) and Bristol (SEQ ID NO: 19, Accession AJ303139);

FIGS. 7A-7D show a nucleotide sequence alignment of sequences encoding human Group C VP-6 for inventive strain S-1 (SEQ ID NO: 31) relative to conventional strains Bristol (SEQ ID NO: 25, Accession CAA42504); Jajeri (SEQ ID NO: 26, Accession AAK26534); CMH004 (SEQ ID NO: 27, Accession ABR31794); V508 (SEQ ID NO: 28, Accession AAX13496); China (SEQ ID NO: 29, Accession BAB83829); and BCN6 (SEQ ID NO: 30, Accession CAJ41549);

FIGS. 8A-8B show an amino acid sequence alignment of sequences encoding human Group C VP-6 for inventive strain S-1 (SEQ ID NO: 32) relative to conventional strains Bristol (SEQ ID NO: 35, Accession CAA42504); Jajeri (SEQ ID NO: 36, Accession AAK26534); CMH004 (SEQ ID NO: 37, Accession ABR31794); V508 (SEQ ID NO: 38, Accession AAX13496); China (SEQ ID NO: 39, Accession BAB83829); and BCN6 (SEQ ID NO: 40, Accession CAJ41549);

FIGS. 9A-9B show a nucleotide sequence of human rotavirus VP6 protein from S-1 strain (SEQ ID No. 46) including an open reading frame, 5' and 3' non-coding sequences; and FIGS. 10A-10C show a nucleotide sequence alignment of sequences encoding human Group C VP-6 and including 5' and 3' non-coding sequences for inventive strain S-1 (SEQ ID NO: 46) and Bristol VP6 (SEQ ID No. 47).

DETAILED DESCRIPTION OF THE INVENTION

Figure 1:
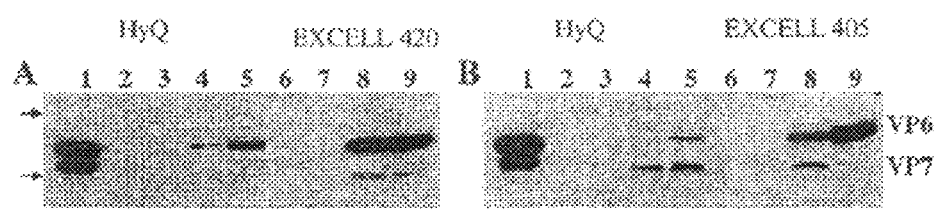
FIG. 1A is an image of an electrophoretic gel showing the kinetics of GpC RV VP6 and VP7 expression in Sf9 cells in different media.
FIG. 1B is an image of an electrophoretic gel showing the kinetics of GpC RV VP6 and VP7 expression in Hi5 (B) cells in different media.
Figure 2:
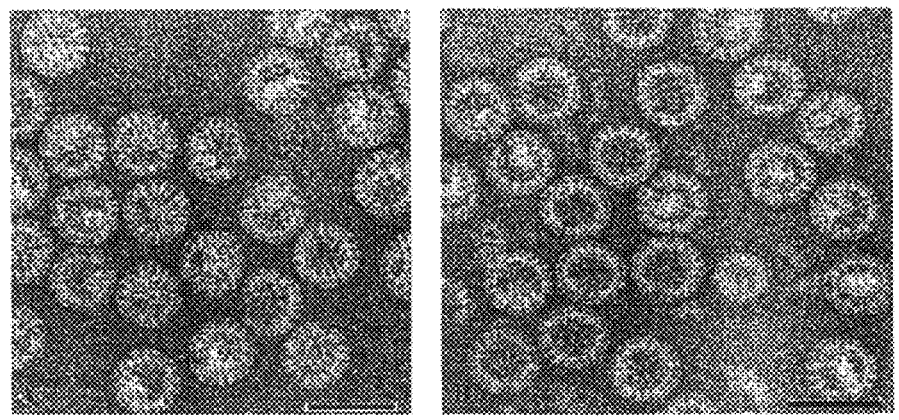
FIG. 2A is an image of an electron micrograph of human GpC RV VLPs formed by self-assembly of recombinant human rotavirus C VP2, VP6, and VP7 proteins expressed in Sf9 cells infected with recombinant baculoviruses at an MOI of 1 each.
FIG. 2B is an image of an electron micrograph of human GpC RV VLPs formed by self-assembly of recombinant human rotavirus C VP6 and VP7 proteins expressed in Sf9 cells infected with recombinant baculoviruses at an MOI of 1.4 each.
Figure 3:
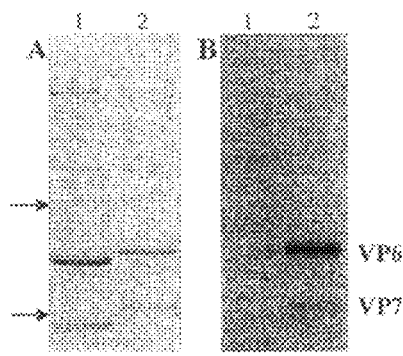
FIG. 3A is an image showing Coomassie blue staining of major structural viral proteins from GpA RV YK-1 and human rotavirus GpC VLPs.
FIG. 3B is an image of an immunoblot showing the comparison of major structural viral proteins from GpA RV YK-1 and human rotavirus GpC VLPs.
Figure 4:
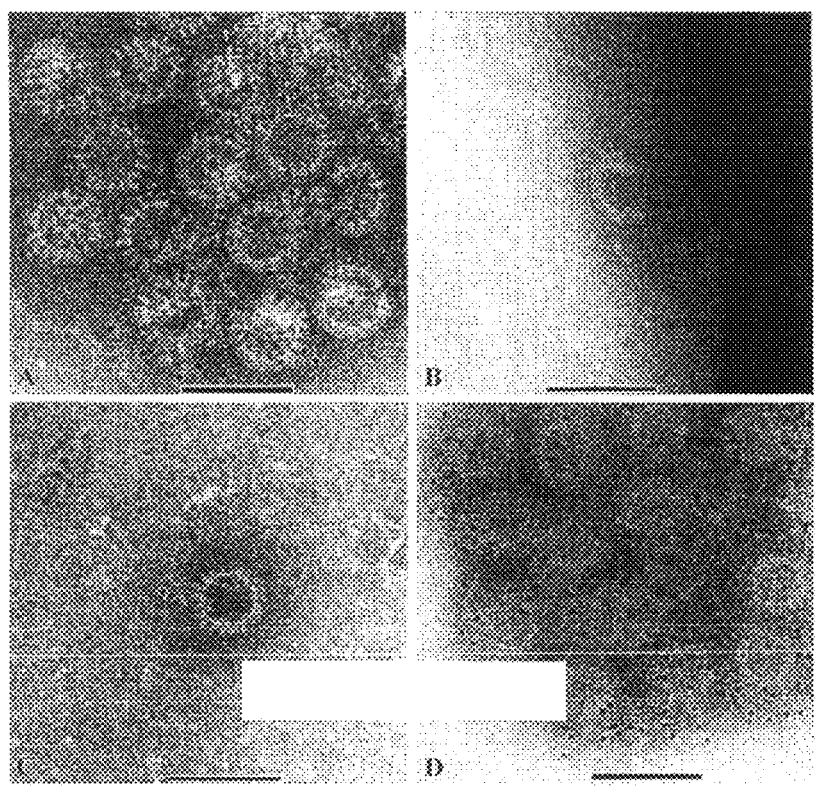
FIG. 4A is an image of an immunoelectron micrograph showing human GpC RV VLPs immunostained with GpC-specific rabbit hyperimmune serum.
FIG. 4B is an image of an immunoelectron micrograph showing human GpC RV VLPs immunostained with GpA-specific rabbit hyperimmune serum.
FIG. 4C is an image of an immunoelectron micrograph showing GpA RV immunostained with GpC-specific rabbit hyperimmune serum.
FIG. 4D is an image of an immunoelectron micrograph showing GpA RV immunostained with GpA-specific rabbit hyperimmune serum.

Group C rotavirus (GpC RV) is a causative agent of acute gastroenteritis in children and adults. Characterization of GpC RV has only been accomplished to date with porcine and bovine strains that can be grown in cell culture. Because human GpC RVs are unstable and cannot be cultivated in cell culture, reagents and sensitive and specific detection methods are not available. Consequently, the impact of GpC RV on diarrheal disease has not been clearly established.

Demonstrated herein is the expression of the major inner and outer capsid human GpC proteins VP6 and VP7 and the human GpC core protein VP2 and the self-assembly of human GpC VP6/7 virus-like particles (VLPs) or human GpC VP2/6/7 VLPs. Antibodies to these human GpC RV VLPs show highly specific reactivities with the corresponding GpC but not GpA RV.

The ability to produce large amounts of human GpC RV antigenic materials, such as human GpC RV proteins and VLPs, and the availability of high quality antibody reagents provide sensitive and specific diagnostic assays and provide tools for investigation of the epidemiology and disease burden of GpC RV in humans.

The instant invention has numerous uses including, but not limited to, detection of human rotavirus C antibodies in biological samples, diagnosis of human rotavirus C infection, identification of individuals previously or currently infected with human rotavirus C, as an antigen for generation of antibodies and for the development of therapeutics for prophylaxis or treatment of disease associated with human rotavirus C infection.

In accordance with the present invention, various techniques and terms including, but not limited to, conventional molecular biology, microbiology, immunology and recombinant DNA techniques and terms, may be used which are known by those of skill in the art. Such techniques and terms are described and/or defined in detail in standard references such as J. Sambrook and D. W. Russell, Molecular Cloning: A Laboratory Manual, Cold Spring Harbor Laboratory Press, 3rd Ed., 2001; F. M. Ausubel et al., Eds., Short Protocols in Molecular Biology, Current Protocols, Wiley, 2002; Wild, D., The Immunoassay Handbook, 3rd Ed., Elsevier Science, 2005; Gosling, J. P., Immunoassays: A Practical Approach, Practical Approach Series, Oxford University Press, 2005; and Harlow, E. and Lane, D., Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B.K.C. Lo, Antibody Engineering: Methods and Protocols, Methods in Molecular Biology, Humana Press, 2003; Crowther, J. R., The ELISA Guidebook (Methods in Molecular Biology), Humana Press, 2000; and other references described herein.

Human Rotavirus C Virus-Like Particles

Human rotavirus C virus-like particles (VLPs) are provided according to the present invention. The term "virus-like particle" refers to a capsid defining an internal space. The internal space defined by the capsid is "empty" of an intact human rotavirus C genome and the human rotavirus C VLPs of the present invention are therefore non-replicating and incapable of causing human rotavirus C-associated disease.

Human rotavirus C VLPs include human rotavirus C VP6 and VP7 proteins according to embodiments of the present invention. In further embodiments of the present invention, human rotavirus C VLPs include human rotavirus C VP2, VP6 and VP7 proteins.

Genes encoding human rotavirus C proteins VP2, VP6 and VP7 have been identified and sequenced.

Any human Group C RV VP6 protein can be included in human rotavirus C VLPs of the present invention. Examples of human Group C RV VP6 proteins that can be included in human rotavirus C VLPs of the present invention include VP6 protein of human Group C strain S-1 VP6 (SEQ ID NO: 32); Bristol strain (SEQ ID NO: 35, Accession CAA42504); Jajeri strain (SEQ ID NO: 36, Accession AAK26534); CMH004 strain (SEQ ID NO: 37, Accession ABR31794); V508 strain (SEQ ID NO: 38, Accession AAX13496); China strain (SEQ ID NO: 39, Accession BAB83829); and BCN6 strain (SEQ ID NO: 40, Accession CAJ41549).

Human Group C RV VP6 proteins that can be included in human GpC RV VLPs include those known by NCBI Accession numbers BAB83829, AAK26535, AAK26534, AAX13496, AAX13492, AAX13491, CAJ41551, CAJ41550, CAJ41549, AAW82662, AAW82661, ABD96606, ABD96605, ABD96604, AAA47340, AAA47339, CAA42504, AAX08120, ABR31794, YP_392512, P69481, P69483 and P69482.

Any human Group C RV VP7 protein can be included in human rotavirus C VLPs of the present invention. Examples of human Group C RV VP7 proteins that can be included in human GpC RV VLPs include those known by NCRI Accession numbers BAB83828, AAX16188, AAX16187, AAX16186, CAJ41554, CAJ41553, CAJ41552, AAW82659, AAD25388, BAA20340, BAA20339, AAQ93808, AAQ93807, AAA47352, BAF73591, BAF73590, BAF73589, BAF73588, BAF73587, BAD20702, BAD20701, BAD20700, BAD20699, AAK26533, AAK26530, ABR31795, BAC53881, BAC53880, BAC53879, BAC53878, BAC53877, BAC53876, BAC53875, BAC53874, ABE01860, ABE01859, ABE01858, AAF33400, AAF33399, AAF33398, AAF33397, AAF33396, AAF33395, AAF33394, AAF33393, AAF33392, AAF33391, AAF33390, AAF33389, BAA33952, P30216, ABO25864 and 2209225A.

Any human Group C RV VP2 protein can be included in human rotavirus C VLPs of the present invention. Examples of human Group C RV VP2 proteins that can be included in human rotavirus C VLPs of the present invention include VP2 protein of human Group C strain ASP88 VP2 (SEQ ID NO: 1); and Bristol strain (SEQ ID NO: 16, Accession CAB52753).

In addition to these VP2, VP6 and VP7 amino acid sequences, the term VP2, VP6 or VP7 amino acid sequence encompasses variants. In particular embodiments, a VP2, amino acid sequence included in a VLP composition of the present invention is a variant of ASP88 VP2 (SEQ ID No. 1). In further embodiments, a VP6, amino acid sequence included in a VLP composition of the present invention is a variant of S-1 VP6 (SEQ ID No. 32). In further embodiments, a VP7, amino acid sequence included in a VLP composition of the present invention is a variant of S-1 VP7 (SEQ ID No. 34).

In another aspect, the invention provides a rotavirus-like particle having a core VP2 structural protein of human group C RV of strain ASP88 protein (SEQ ID NO: 1) or a fragment or variant thereof.

In another aspect, the invention provides a rotavirus-like particle comprising VP6 capsid protein and VP7 capsid protein, or fragments or variants thereof, with the proviso that said particle does not comprise an amino acid sequence set forth in (SEQ ID NO: 16; Bristol).

In another aspect, the invention provides an isolated polypeptide comprising an amino acid sequence selected from the group consisting of: a) an amino acid sequence having at least 98% identity to the amino acid sequence set forth in SEQ ID NO: 1 (ASP88 VP2 amino acid sequence); b) an amino acid sequence having at least 99% identity to the amino acid sequence set forth in SEQ ID NO: 1 (ASP88 VP2 amino acid sequence); c) an amino acid sequence set forth in SEQ ID NO: 1 (ASP88 VP2 amino acid sequence); and d) an amino acid sequence set forth in SEQ ID NO: 32 (S-1 VP6 amino acid sequence).

In another aspect, the invention provides an isolated nucleic acid molecule comprising a nucleotide sequence encoding one or more of the inventive polypeptides described herein. In certain embodiments the invention provides an isolated nucleic acid molecule encoding VP2 selected from the group consisting of: a) an isolated nucleic acid molecule encoding an inventive polypeptide having at least 98% identity to the amino acid sequence set forth in SEQ ID NO: 1 (ASP88 VP2 amino acid sequence); b) an isolated nucleic acid molecule encoding an inventive polypeptide having at least 99% identity to the amino acid sequence set forth in SEQ ID NO: 1 (ASP88 VP2 amino acid sequence); c) an isolated nucleic acid molecule encoding an inventive polypeptide set forth in SEQ ID NO: 1 (ASP88 VP2 amino acid sequence); and d) an isolated nucleic acid molecule encoding an inventive amino acid sequence set forth in SEQ ID NO: 32 (S-1 VP6 amino acid sequence).

In another aspect, the invention provides an immunogenic composition that includes a polypeptide containing at least one amino acid sequence of:

```
                                        (SEQ ID NO: 2)
LETIIDKEVK ENKDSTKDEK LVVTEESNGD VTA, (SEQ ID NO: 3)
LETIINKEVK ENKDSMKEDK LVVTEESNGD VTT, (SEQ ID NO: 4)
TENVEEKEIK EAKEQVKDEK QVITEENVDS PKD, (SEQ ID NO: 5)
KLTEIQESSA KTYNTLFRLF TP, (SEQ ID NO: 6)
NYRNSRIKCQ TYNKLFRL, (SEQ ID NO: 7)
LNVLEG MPDYIMLRDM AV, (SEQ ID NO: 8)
LNVLEE MPDYIMLRDM AV, (SEQ ID NO: 9)
LNVLDE MPDYVMLRDM AV, (SEQ ID NO: 10)
AAHLQLE AITVQVESQF LAGISAAAAN EA, (SEQ ID NO: 11)
LQCKLNH NSWQELVHGR NE, (SEQ ID NO: 12)
LSACIVMNMH LVG,
and (SEQ ID NO: 13)
IPPDQMYRLR NRLRNIP;
``` wherein said amino sequence is an antigenic epitope recognized by an antibody.

In another aspect, the invention provides a antibody preparation that recognizes an amino acid sequence of:

```
                                        (SEQ ID NO: 2)
LETIIDKEVK ENKDSTKDEK LVVTEESNGD VTA, (SEQ ID NO: 3)
LETIINKEVK ENKDSMKEDK LVVTEESNGD VTT, (SEQ ID NO: 4)
TENVEEKEIK EAKEQVKDEK QVITEENVDS PKD, (SEQ ID NO: 5)
KLTEIQESSA KTYNTLFRLF TP, (SEQ ID NO: 6)
NYRNSRIKCQ TYNKLFRL, (SEQ ID NO: 7)
LNVLEG MPDYIMLRDM AV, (SEQ ID NO: 8)
LNVLEE MPDYIMLRDM AV,
```

```
LNVLDE MPDYVMLRDM AV,                          (SEQ ID NO: 9)

(SEQ ID NO: 10)
AAHLQLE AITVQVESQF LAGISAAAAN EA, (SEQ ID NO: 11)
LQCKLNH NSWQELVHGR NE, (SEQ ID NO: 12)
LSACIVMNMH LVG,
and (SEQ ID NO: 13)
IPPDQMYRLR NRLRNIP.
```

In another aspect, the invention provides a vector comprising the inventive nucleic acid molecules described herein.

In another aspect, the invention provides an isolated host cell comprising one or more of the inventive vectors described herein.

The inventive methods and compositions are not limited to the VP proteins and polypeptides having the amino acid sequence described herein in detail. Where appropriate, variants, such as homologs from other strains and groups, may be used.

As used herein, the term "variant" defines either a naturally occurring genetic mutant of a human rotavirus C virus or a recombinantly prepared variation of a human rotavirus C virus, each of which contain one or more mutations in its genome compared to a reference human rotavirus C VP2, VP6 or VP7. The term "variant" may also refer to either a naturally occurring variation of a given peptide or a recombinantly prepared variation of a given peptide or protein in which one or more amino acid residues have been modified by amino acid substitution, addition, or deletion.

Preferred are human rotavirus C proteins having at least 95%, 96%, 97%, 98% or 99% identity to SEQ ID No. 1, SEQ ID No. 32 or SEQ ID No. 34. Further preferred are human rotavirus C proteins having 99% or greater identity to SEQ ID No. 1, SEQ ID No. 32 or SEQ ID No. 34.

Mutations can be introduced using standard molecular biology techniques, such as site-directed mutagenesis and PCR-mediated mutagenesis. One of skill in the art will recognize that one or more amino acid mutations can be introduced without altering the functional properties of the human rotavirus C VP2, VP6 or VP7 proteins.

It is also recognized by one of ordinary skilled in the art that VP protein and polypeptide variants encompass conservative amino acid substitutions in the amino acid sequences of the VP proteins and polypeptides set forth in detail herein. Conservative amino acid substitutions can be made in human rotavirus C VP2, VP6 or VP7 proteins to produce human rotavirus C VP2, VP6 or VP7 protein variants. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamate, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

Human rotavirus C VP2, VP6 or VP7 variants can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

In addition, as will be appreciated by one of skill in the art, due to the degeneracy of the genetic code, more than one nucleic acid will encode an identical protein. Thus, nucleic acids encoding the VP proteins and polypeptides or a variant thereof are not limited to those nucleic acids described herein in detail.

Variants of VP proteins and polypeptides having 95%, 96%, 97%, 98%, or 99% homology to the amino acid sequence described herein in detail are operable in the described methods and compositions. Variants of nucleic acids having 95%, 96%, 97%, 98%, or 99% homology to the nucleotide sequence described herein in detail are operable in the described methods and compositions.

"Homology" refers to sequence similarity or, alternatively, sequence identity, between two or more polynucleotide sequences or two or more polypeptide sequences.

The terms "percent identity" and "% identity", as applied to polynucleotide sequences, refer to the percentage of identical nucleotide matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Percent identity between polynucleotide sequences may be determined using one or more computer algorithms or programs known in the art or described herein. For example, percent identity can be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989; CABIOS 5:151-153) and in Higgins, D. G. et al. (1992; CABIOS 8:189-191). For pairwise alignments of polynucleotide sequences, the default parameters are set as follows: Ktuple=2, gap penalty=5, window=4, and "diagonals saved"=4. The "weighted" residue weight table is selected as the default.

Alternatively, a suite of commonly used and freely available sequence comparison algorithms which can be used is provided by the National Center for Biotechnology Information (NCBI) Basic Local Alignment Search Tool (BLAST) (Altschul, S. F. et al. (1990) J. Mol. Biol. 215:403-410), which is available from several sources, including the NCBI, Bethesda, Md., and on the NCBI World Wide Web site available on the Internet. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively on the Internet via the NCBI World Wide Web site as well. The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.12 (Apr. 21, 2000) set at default parameters. Such default parameters may be, for example: Matrix:BLOSUM62; Reward for match: 1; Penalty for mismatch: −2; Open Gap: 5 and Extension Gap: 2 penalties; Gap x drop-off: 50; Expect: 10; Word Size: 11; Filter: on.

Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or sequence listing, may be used to describe a length over which percentage identity may be measured.

The phrases "percent identity" and "% identity", as applied to polypeptide sequences, refer to the percentage of identical residue matches between at least two polypeptide sequences aligned using a standardized algorithm. Methods of polypeptide sequence alignment are well known. Some alignment methods take into account conservative amino acid substitutions. Such conservative substitutions, explained in more detail above, generally preserve the charge and hydrophobicity at the site of substitution, thus preserving the structure (and therefore function) of the polypeptide. The phrases "percent similarity" and "% similarity", as applied to polypeptide sequences, refer to the percentage of residue matches, including identical residue matches and conservative substitutions, between at least two polypeptide sequences aligned using a standardized algorithm. In contrast, conservative substitutions are not included in the calculation of percent identity between polypeptide sequences.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. The PAM250 matrix is selected as the default residue weight table.

Alternatively the NCBI BLAST software suite may be used. For example, for a pairwise comparison of two polypeptide sequences, one may use the "BLAST 2 Sequences" tool Version 2.0.12 (Apr. 21, 2000) with blastp set at default parameters. Such default parameters may be, for example: Matrix: BLOSUM62; Open Gap: 11 and Extension Gap: 1 penalties; Gap x drop-off: 50; Expect: 10; Word Size: 3; Filter: on.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or sequence listing, may be used to describe a length over which percentage identity may be measured.

Furthermore, fragments of the proteins and polypeptides and variants thereof are encompassed in the methods and compositions of the invention, so long as the fragment is operable in effecting the relevant biological activity as understood by the ordinarily skilled artisan. Thus, for example, fragments include fragments of VP2 proteins and polypeptides; where the fragment is contained in a virus-like particle when expressed in an insect cell culture along with a VP6 and VP7 protein or polypeptide, or a variant or fragment thereof. Thus, for example, fragments include fragments of VP6 proteins and polypeptides; where the fragment is contained in a virus-like particle when expressed in an insect cell culture along with a VP7 protein or polypeptide, or a variant or fragment thereof. Thus, for example, fragments include fragments of VP7 proteins and polypeptides; where the fragment is contained in a virus-like particle when expressed in an insect cell culture along with a VP6 protein or polypeptide, or a variant or fragment thereof. Fragments also encompass those fragments which effect an immunogenic response as described herein for a VP protein, polypeptide or a variant there.

Processes for Making VLPs

VP2 core protein and the VP6 and VP7 capsid proteins and polypeptides (VP proteins and polypeptides) described in the compositions and methods described herein can be generated by recombinant methods, such as the inventive methods described herein, or by suitable expression methods known to the ordinarily skilled artisan where appropriate. Nucleic acid sequences encoding the VP proteins and polypeptides are isolated as exemplified by nucleic acid sequences described herein.

VLPs are produced using recombinant nucleic acid technology according to embodiments of the present invention. VLP production includes introducing a recombinant expression vector encompassing a DNA sequence encoding human rotavirus C VP2, VP6 and/or VP7 into a host cell.

Specific nucleic acid sequences encoding human rotavirus C VP2, VP6 or VP7 introduced into a host cell to produce human rotavirus C VLPs are It is appreciated that due to the degenerate nature of the genetic code, alternate nucleic acid sequences encode human rotavirus C VP2, VP6 or VP7 and variants thereof, and that such alternate nucleic acids may be included in an expression vector and expressed to produce human rotavirus C VLPs of the present invention.

In embodiments of the present invention, a nucleic acid sequence which is substantially identical to SEQ ID No. 31, SEQ ID NO: 46, or SEQ ID No. 48 encoding human rotavirus GpC VP6, is included in an expression vector and expressed to produce human rotavirus C VLPs of the present invention. In further embodiments of the present invention, a nucleic acid sequence which is substantially identical to SEQ ID No. 33 encoding human rotavirus GpC VP7, is included in an expression vector and expressed to produce human rotavirus C VLPs of the present invention. In further embodiments of the present invention, a nucleic acid sequence which is substantially identical to SEQ ID No. 18, SEQ ID No. 42 or SEQ ID No. 43 encoding human rotavirus GpC VP2, is included in an expression vector and expressed to produce human rotavirus C VLPs of the present invention.

A nucleic acid sequence which is substantially identical to SEQ ID No. 31 or SEQ ID NO: 46 is characterized as having a complementary nucleic acid sequence capable of hybridizing to SEQ ID No. 31, SEQ ID NO: 46, or SEQ ID No. 48 under high stringency hybridization conditions. Similarly, a nucleic acid sequence which is substantially identical to SEQ ID No. 33, SEQ ID No. 18, SEQ ID No. 42 or SEQ ID No. 43, is characterized as having a complementary nucleic acid sequence capable of hybridizing to SEQ ID No. 33 or SEQ ID No. 18, SEQ ID No. 42 or SEQ ID No. 43, respectively, under high stringency hybridization conditions.

The term "nucleic acid" refers to RNA or DNA molecules having more than one nucleotide in any form including single-stranded, double-stranded, oligonucleotide or polynucleotide. The term "nucleotide sequence" refers to the ordering of nucleotides in an oligonucleotide or polynucleotide in a single-stranded form of nucleic acid.

The term "complementary" refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone. Under highly stringent conditions, SEQ ID No. 31, SEQ ID No. 33 and SEQ ID No. 18 will hybridize to the complement of substantially identical targets and not to unrelated sequences.

The term "expression vector" refers to a recombinant vehicle for introducing a DNA sequence encoding one or more human rotavirus C proteins into a host cell where the DNA sequence is expressed to produce the one or more human rotavirus C proteins.

In particular embodiments, a DNA sequence encoding one or more human rotavirus C proteins includes an open reading frame encoding the one or more human rotavirus C proteins.

In further embodiments, 5' non-coding sequence and/or 3' non-coding sequence is present in addition to the open reading frame encoding the one or more human rotavirus C proteins. Preferably, where 5' non-coding sequence and/or 3' non-coding sequence is present, it is contiguous with the DNA sequence encoding one or more human rotavirus C proteins, 5' non-coding sequence, if any, is positioned upstream (5') of the start codon and 3' non-coding sequence, if any, is positioned downstream (3') of the stop codon.

In particular embodiments, an expression vector including SEQ ID No. 42 or a substantially identical nucleic acid sequence is expressed to produce human rotavirus C VP2 and self-assembled VLPs in cells containing the expression vector. SEQ ID No. 42 includes an open reading frame encoding human rotavirus C VP2 from strain Asp88. Optionally, 5' non-coding sequence and/or 3' non-coding sequence of human rotavirus C VP2 from strain Asp88 is included in the expression vector. For example, 1-36 nucleotides of 5' non-coding sequence can be included contiguous with the 5' end of the nucleotide sequence encoding human rotavirus C VP2 from strain Asp88. In particular embodiments, an expression vector including SEQ ID No. 18 or a substantially identical nucleic acid sequence is expressed to produce human rotavirus C VP2 and self-assembled VLPs in cells containing the expression vector. In further embodiments, an expression vector including SEQ ID No. 43 or a substantially identical nucleic acid sequence is expressed to produce human rotavirus C VP2 and self-assembled VLPs in cells containing the expression vector.

In additional embodiments, an expression vector including SEQ ID No. 31, SEQ ID NO: 46, SEQ ID No. 48 or a substantially identical nucleic acid sequence is expressed to produce human rotavirus C VP6 and self-assembled VLPs in cells containing the expression vector.

In additional embodiments, an expression vector including SEQ ID No. 33, SEQ ID No. 45, or a substantially identical nucleic acid sequence is expressed to produce human rotavirus C VP7 and self-assembled VLPs in cells containing the expression vector.

In further embodiments, an expression vector including SEQ ID No. 31, SEQ ID NO: 46, SEQ ID No. 48 or a substantially identical nucleic acid sequence and SEQ ID No. 33, SEQ ID No. 45, or a substantially identical nucleic acid sequence is expressed to produce human rotavirus C VP6, human rotavirus C VP7 and self-assembled VLPs, in cells containing the expression vector.

In further embodiments, an expression vector including SEQ ID No. 31, SEQ ID NO: 46, SEQ ID No. 48 or a substantially identical nucleic acid sequence, SEQ ID No. 33, SEQ ID No. 45, or a substantially identical nucleic acid sequence and SEQ ID No. 18, SEQ ID No. 42, SEQ ID No. 43, or a substantially identical nucleic acid sequence is expressed to produce human rotavirus C VP6, human rotavirus C VP7, human rotavirus C VP2 and self-assembled VLPs in cells containing the expression vector.

In still further embodiments, a first expression vector including SEQ ID No. 31, SEQ ID NO: 46, SEQ ID No. 48 or a substantially identical nucleic acid sequence and a second expression vector including SEQ ID No. 33, SEQ ID No. 45, or a substantially identical nucleic acid sequence are both expressed to produce human rotavirus C VP6, human rotavirus C VP7 and self-assembled VLPs in cells containing the expression vectors.

In still further embodiments, a first expression vector including SEQ ID No.31, SEQ ID NO: 46, SEQ ID No. 48 or a substantially identical nucleic acid sequence, a second expression vector including SEQ ID No. 33, SEQ ID No. 45, or a substantially identical nucleic acid sequence and a third expression vector including SEQ ID No. 18, SEQ ID No. 42, SEQ ID No. 43, or a substantially identical nucleic acid sequence are expressed to produce human rotavirus C VP6, human rotavirus C VP7, human rotavirus C VP2, and self-assembled VLPs in cells containing the expression vectors.

In addition to one or more DNA sequences encoding proteins of human rotavirus C, one or more DNA sequences encoding additional proteins can be included in an expression vector. For example, such additional proteins include non-human rotavirus C proteins such as reporters, including, but not limited to, beta-galactosidase, green fluorescent protein and antibiotic resistance reporters; and antigens.

Expression vectors are known in the art and include plasmids and viruses, for example. An expression vector contains a DNA molecule that includes segment encoding a polypeptide of interest operably linked to one or more regulatory elements that provide for transcription of the segment encoding the polypeptide of interest. Such regulatory elements include, but are not limited to, promoters, terminators, enhancers, origins of replication and polyadenylation signals.

In particular embodiments, the recombinant expression vector encodes human rotavirus C VP2 of SEQ ID No. 1, a protein having at least 95% identity to SEQ ID No. 1, a protein encoded by SEQ ID No. 42, or a protein encoded by a nucleic acid sequence substantially identical to SEQ ID No. 42.

In particular embodiments, the recombinant expression vector encodes human rotavirus C VP6 of SEQ ID No. 32, a protein having at least 95% identity to SEQ ID No. 32, a protein encoded by SEQ ID No. 31, or a protein encoded by a nucleic acid sequence substantially identical to SEQ ID No. 31.

In particular embodiments, the recombinant expression vector encodes human rotavirus C VP7 of SEQ ID No. 34, a protein having at least 95% identity to SEQ ID No. 34, a protein encoded by SEQ ID No. 33 or SEQ ID No. 45, or a protein encoded by a nucleic acid sequence substantially identical to SEQ ID No. 33 or SEQ ID No. 45.

In further embodiments, the recombinant expression vector encodes human rotavirus C VP6 of SEQ ID No. 32, a protein having at least 95% identity to SEQ ID No. 32, a protein encoded by SEQ ID No. 31, or a protein encoded by a nucleic acid sequence substantially identical to SEQ ID No. 31; and human rotavirus C VP7 of SEQ ID No. 34, a protein having at least 95% identity to SEQ ID No. 34, a protein encoded by SEQ ID No. 33 or SEQ ID No. 45, or a protein encoded by a nucleic acid sequence substantially identical to SEQ ID No. 33 or SEQ ID No. 45.

A preferred expression vector of the present invention is a baculovirus.

Expression of human rotavirus C VP2, VP6 and/or VP7 encoded by a recombinant expression vector is accomplished by introduction of the expression vector into a eukaryotic or prokaryotic host cell expression system such as an insect cell, mammalian cell, yeast cell, bacterial cell or any other single or multicellular organism recognized in the art. In preferred embodiments, a eukaryotic host cell is used. Host cells are optionally primary cells or immortalized derivative cells. Immortalized cells are those which can be maintained in-vitro for at least 5 replication passages.

Host cells containing the recombinant expression vector are maintained under conditions where human rotavirus C proteins are produced. The human rotavirus C proteins self-associate to produce VLPs of the present invention in the host cell.

The invention provides a host cell containing a nucleic acid sequence according to the invention. Host cells may be cultured and maintained using known cell culture techniques such as described in Celis, Julio, ed., 1994, Cell Biology Laboratory Handbook, Academic Press, N.Y. Various culturing conditions for these cells, including media formulations with regard to specific nutrients, oxygen, tension, carbon dioxide and reduced serum levels, can be selected and optimized by one of skill in the art.

A preferred cell line of the present invention is a eukaryotic cell line, preferably an insect cell line, such as Sf9 or Hi5, transiently or stably expressing one or more full-length or partial human rotavirus C proteins. Such cells can be made by transfection (proteins or nucleic acid vectors), infection (viral vectors) or transduction (viral vectors). The cell lines for use in the present invention are cloned using known cell culture techniques familiar to one skilled in the art. The cells are cultured and expanded from a single cell using commercially available culture media under known conditions suitable for propagating cells.

In a preferred embodiment human rotavirus C VLPs are produced by infection of a host cell with at least one recombinant baculovirus encoding human rotavirus C protein(s).

It is appreciated that a single baculovirus may encode either a single human rotavirus C protein or multiple human rotavirus C proteins. The resulting infected cells are then cultured under conditions whereby the encoded human rotavirus C proteins from the respective recombinant baculoviruses are produced and self assemble to form the capsids. The resulting human rotavirus C VLPs are then optionally and preferably isolated.

In further preferred embodiments, the recombinant baculovirus encodes at least human rotavirus C VP6 of SEQ ID No. 32, a protein having at least 95% identity to SEQ ID No. 32, a protein encoded by SEQ ID No. 31, or a protein encoded by a nucleic acid sequence substantially identical to SEQ ID No. 31, SEQ ID NO: 46 or SEQ ID No. 48; and human rotavirus C VP7 of SEQ ID No. 34, a protein having at least 95% identity to SEQ ID No. 34, a protein encoded by SEQ ID No. 33 or SEQ ID No. 45, or a protein encoded by a nucleic acid sequence substantially identical to SEQ ID No. 33 or SEQ ID No. 45.

In a further option, the recombinant baculovirus encodes human rotavirus C VP2 of SEQ ID No. 1, a protein having at least 95% identity to SEQ ID No. 1, a protein encoded by SEQ ID No. 42, or a protein encoded by a nucleic acid sequence substantially identical to SEQ ID No. 42.

Any suitable baculovirus known in the art is operable in the instant inventive process. Preferably, the baculovirus is Autographa california nuclear polyhedrosis virus.

Processes for infecting cells with baculovirus are known in the art. Following infection of a host cell the inventive process proceeds by culturing the host cells under conditions such that protein(s) produced self assemble to form VLPs.

A VLP of the present invention optionally includes a non-human rotavirus C protein or peptide in contact with or bonded to at least one of the human rotavirus C proteins VP2, VP6 or VP7. Bonding of the non-human rotavirus C protein or peptide is achieved, for example, by expression of a fusion construct including a nucleic acid sequence encoding VP2, VP6 or VP7 and the non-human rotavirus C protein or peptide. Thus, the non-human rotavirus C protein or peptide is optionally a fusion protein or peptide wherein the non-human rotavirus C protein is synthesized as a single polypeptide chain with a human rotavirus C structural protein.

The non-human rotavirus C protein is optionally fused with glutathione-S-transferase (GST) for rapid isolation. A human rotavirus C protein is also optionally fused to GST.

Chemical bonding methods are optionally used to bond a VLP and a non-human rotavirus C protein or peptide, illustratively including reaction using a cross-linking agent such as carbodiimide or glutaraldehyde.

In particular embodiments, the non-human rotavirus C protein or peptide included in the VLP includes one or more antigenic epitopes such that the VLP serves to present the one or more antigenic epitopes to the immune system of a subject to induce antibody generation.

In a further option, the non-human rotavirus C protein or peptide is a targeting moiety such as a receptor ligand or receptor. A targeting moiety is included in the VLP to direct the VLP to a target, such as to a particular cell type.

Human rotavirus C VLPs produced in a host cell are optionally isolated. The term "isolated" in reference to a human rotavirus C VLP describes a human rotavirus C VLP which is separated from a cell in which the human rotavirus C VLP is produced and which is substantially free of host cell components not intended to be associated with the human rotavirus C VLP. Generally, human rotavirus C VLPs are separated from whole cell extracts of host cells. Numerous processes of isolating VLPs are known in the art and are applicable to isolation of human rotavirus C VLPs illustratively including sucrose continuous and discontinuous gradients, cesium chloride single and multi-density gradient centrifugation, size-exclusion chromatography, antigen capture chromatography, affinity chromatography, or other suitable process known in the art. An exemplary method for isolating human rotavirus C VLPs of the present invention is described in Gillock, ET. et al, 1997. J. Virol., 71:2857-2865.

Human rotavirus C VLPs having different compositions, that is, different "types" of human rotavirus C VLPs are optionally present in a composition of the present invention. For example, human rotavirus C VLPs including human rotavirus C VP2 are optionally included in a composition with antigen presenting human rotavirus C VLPs including a non-human rotavirus C protein or peptide and/or human rotavirus C VLPs containing a cargo moiety.

In one aspect, the invention provides a method of making a human group C rotavirus-like particle comprising: constructing a first baculovirus vector comprising a nucleic acid molecule comprising a sequence encoding a human group C RV VP6 capsid protein operably linked to a baculovirus promoter that drives expression of said protein in an insect cell; constructing a second baculovirus vector comprising a nucleic acid molecule comprising a sequence encoding a human group C RV VP7 capsid protein operably linked to a baculovirus promoter that drives expression of said protein in an insect cell; and infecting an insect cell culture with said first and second baculovirus vector under conditions that promote expression of the VP6- and VP7 capsid proteins.

In one embodiment of the present invention, the method further comprises constructing a third baculovirus vector comprising a nucleic acid molecule comprising a sequence encoding a human group C RV VP2 core protein operably linked to a baculovirus promoter that drives expression of said protein in an insect cell; and infecting an insect cell culture with said first, second, and third baculovirus vector under conditions that promote expression of the VP6 capsid protein and VP7 capsid protein and said VP2 core protein.

In another aspect, the invention provides a rotavirus-like particle made by the herein described inventive method.

A virus-like particle containing a fragment of the VP proteins described herein can be formed by any of the above described methods for making a human group C rotavirus-like particle, and also includes: constructing a third baculovirus vector comprising a nucleic acid molecule comprising a sequence encoding a core protein operably linked to a baculovirus promoter that drives expression of said protein in an insect cell; infecting an insect cell culture with said first, second, and third baculovirus vector under conditions that promote expression of the VP6- and VP7 capsid proteins, and the VP2 core protein.

In one embodiment of the present invention, the core protein is a group C VP2 protein of ASP 88 strain.

Rotavirus particles are harvested, typically from cell culture supernatant for inclusion in an immunogenic composition including a vaccine composition. The rotavirus particles may be isolated from the cell culture supernatant, for example by filtration and/or centrifugation. The isolated rotavirus particles are optionally lyophilized, such as for later resuspension in a pharmaceutically acceptable carrier.

Pharmaceutical Compositions and Processes

Pharmaceutical Compositions and Processes

Vaccines and methods for their use to induce active immunity and protection against human rotavirus C-induced illness in a subject are provided according to the present invention.

In particular embodiments, human rotavirus C VLPs are administered as antigens for prevention or treatment of human rotavirus C infection such as by serving as an active vaccine component, or by eliciting an immune response in a host organism. Vaccine delivery may occur prior to or following human rotavirus C infection of a host organism or patient. A vaccine optionally contains one or more adjuvants and preservatives or other pharmaceutically acceptable carrier.

In particular embodiments, vaccine compositions include one or more types of human rotavirus C VLP admixed with a pharmaceutically acceptable carrier.

The term "pharmaceutically acceptable carrier" refers to a carrier which is substantially non-toxic to a subject and substantially inert to the human rotavirus C VLPs included in a vaccine composition. A pharmaceutically acceptable carrier is a solid, liquid or gel in form and is typically sterile and pyrogen free.

An immunogenic composition of the present invention may be in any form suitable for administration to a subject.

An immunogenic composition is administered by any suitable route of administration including oral and parenteral such as intravenous, intradermal, intramuscular, intraperitoneal, mucosal, nasal, or subcutaneous routes of administration.

For example, an immunogenic composition for parenteral administration may be formulated as an injectable liquid including a rotavirus and a pharmaceutically acceptable carrier. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of a desirable particle size in the case of dispersions, and/or by the use of a surfactant, such as sodium lauryl sulfate. A stabilizer is optionally included such as, for example, EDTA, EGTA, and an antioxidant.

A solid dosage form for administration or for suspension in a liquid prior to administration illustratively includes capsules, tablets, powders, and granules. In such solid dosage forms, rotavirus particles are admixed with at least one carrier illustratively including a buffer such as, for example, sodium citrate or an alkali metal phosphate illustratively including sodium phosphates, potassium phosphates and calcium phosphates; a filler such as, for example, starch, lactose, sucrose, glucose, mannitol, and silicic acid; a binder such as, for example, carboxymethylcellulose, alignates, gelatin, polyvinylpyrrolidone, sucrose, and acacia; a humectant such as, for example, glycerol; a disintegrating agent such as, for example, agar-agar, calcium carbonate, plant starches such as potato or tapioca starch, alginic acid, certain complex silicates, and sodium carbonate; a solution retarder such as, for example, paraffin; an absorption accelerator such as, for example, a quaternary ammonium compound; a wetting agent such as, for example, cetyl alcohol, glycerol monostearate, and a glycol; an adsorbent such as, for example, kaolin and bentonite; a lubricant such as, for example, talc, calcium stearate, magnesium stearate, a solid polyethylene glycol or sodium lauryl sulfate; a preservative such as an antibacterial agent and an antifungal agent, including for example, thimerosal, sorbic acid, gentamycin and phenol; and a stabilizer such as, for example, EDTA, EGTA, and an antioxidant.

Solid dosage forms optionally include a coating such as an enteric coating. The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied having a thickness such that the entire coating does not dissolve in the gastrointestinal fluids at pH below 3 associated with stomach acids, yet dissolves above pH 3 in the small intestine environment. It is expected that any anionic polymer exhibiting a pH-dependent solubility profile is readily used as an enteric coating in the practice of the present invention to achieve delivery of the active agent to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particular enteric coating material includes acrylic acid polymers and copolymers described for example U.S. Pat. No. 6,136,345.

The enteric coating optionally contains a plasticizer to prevent the formation of pores and cracks that allow the penetration of the gastric fluids into the solid dosage form. Suitable plasticizers illustratively include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g. hydroxypropylcellulose, acids or bases) to solubilize or disperse the coating material, and to improve coating performance and the coated product.

Liquid dosage forms for oral administration include rotavirus and a pharmaceutically acceptable carrier formulated as an emulsion, solution, suspension, syrup, or elixir. A liquid dosage form of a vaccine composition of the present invention may include a wetting agent, an emulsifying agent, a suspending agent, a sweetener, a flavoring, or a perfuming agent.

Detailed information concerning customary ingredients, equipment and processes for preparing dosage forms is found in Pharmaceutical Dosage Forms: Tablets, eds. H. A. Lieberman et al., New York: Marcel Dekker, Inc., 1989; and in L. V. Allen, Jr. et al., Ansel's Pharmaceutical Dosage Forms and Drug Delivery Systems, 8th Ed., Philadelphia, Pa.: Lippincott, Williams & Wilkins, 2004; A. R. Gennaro, Remington: The Science and Practice of Pharmacy, Lippincott Williams & Wilkins, 20th ed., 2003; and J. G. Hardman et al., Goodman & Gilman's The Pharmacological Basis of Therapeutics, McGraw-Hill Professional, 10th ed., 2001.

An adjuvant is optionally included in a virus composition according to embodiments of the present invention. Adjuvants are known in the art and illustratively include Freund's adjuvant, aluminum hydroxide, aluminum phosphate, aluminum oxide, saponin, dextrans such as DEAE-dextran, vegetable oils such as peanut oil, olive oil, and/or vitamin E acetate, mineral oil, bacterial lipopolysaccharides, peptidoglycans, and proteoglycans.

The term "subject" is used herein to refer to a human. Non-human animals, illustratively including cows, horses, sheep, goats, pigs, dogs, cats, birds, poultry, and rodents, are also referred to by the term subject in particular embodiments of the present invention.

A vaccine composition of the present invention may be in any form suitable for administration to a subject.

A vaccine composition is administered by any suitable route of administration including oral and parenteral such as intravenous, intradermal, intramuscular, intraperitoneal, mucosal, nasal, or subcutaneous routes of administration.

The phrase "therapeutically effective amount" refers to an amount effective to induce an immunological response and prevent or ameliorate signs or symptoms of human rotavirus C-mediated disease. Induction of an immunological response in a subject can be determined by any of various techniques known in the art, illustratively including detection of anti-human rotavirus C antibodies, measurement of anti-human rotavirus C antibody titer and/or lymphocyte proliferation assay. Signs and symptoms of human rotavirus C-mediated disease may be monitored to detect induction of an immunological response to administration of a vaccine composition of the present invention in a subject.

Administration of a vaccine composition according to a method of the present invention includes administration of one or more doses of a vaccine composition to a subject at one time in particular embodiments. Alternatively, two or more doses of a vaccine composition are administered at time intervals of weeks—years. A suitable schedule for administration of vaccine composition doses depends on several factors including age and health status of the subject, type of vaccine composition used and route of administration, for example. One of skill in the art is able to readily determine a dose and schedule of administration to be administered to a particular subject.

Immunogenicity of human rotavirus C VLPs is tested by any of various assays known in the art. In a particular example, purified human rotavirus C VLPs are administered intramuscularly to mice with or without an adjuvant. Immunogenicity is assayed by measuring immunoglobulin titers including IgM, IgA and/or IgG in blood samples obtained at various times after administration.

Neutralizing antibody titers are measured by neutralization assays known in the art, such as those generally described in Kuby, J., Immunology, 3rd ed. W.H. Freeman and Co., New York, N.Y., 1997. Since human rotavirus C does not grow in culture, sera from mice injected with human rotavirus C VLPs are serially diluted two-fold in duplicate wells and incubated with trypsin-activated porcine rotavirus C. Activated porcine rotavirus C or serum-free MEM medium is incubated in the absence of mouse serum and serve as positive and negative controls, respectively. MA104 cells in MEM medium supplemented with trypsin are added to each well. After incubation at 37° C. for 18 hours, cells are fixed with formalin. Porcine rotavirus C antigens in the fixed MA104 cells are detected by incubating cells with HRP-labeled rabbit IgG against human rotavirus VLPs, and then tetramethyl benzidine. Neutralizing antibody titer in a serum is defined as the reciprocal of the highest dilution giving a 70% reduction in absorbance value compared to that in the virus control.

Optionally, antibodies raised to immunogenic human rotavirus C VLPs are administered to a subject for prevention or therapeutic treatment relating to human rotavirus C-mediated disease.

Additional therapeutics that are optionally administered with the vaccine composition or antibodies raised to human rotavirus C VLPs include antivirals such as amantadine, rimantadine, gancyclovir, acyclovir, ribavirin, penciclovir, oseltamivir, foscarnet zidovudine (AZT), didanosine (ddI), lamivudine (3TC), zalcitabine (ddC), stavudine (d4T), nevirapine, delavirdine, indinavir, ritonavir, vidarabine, nelfinavir, saquinavir, relenza, tamiflu, pleconaril, interferons; steroids and corticosteroids such as prednisone, cortisone, fluticasone and glucocorticoid; antibiotics; analgesics; antidiarrheals, fluid replacement; or other treatments for rotavirus infection.

The invention also provides a pharmaceutical kit that includes one or more receptacles containing one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In a preferred embodiment, the kit contains an antibody specific for human rotavirus C VP2, human rotavirus C VP6, human rotavirus C VP7, the polypeptide of SEQ ID NO: 1, an epitope or a variant thereof, the polypeptide of SEQ ID NO: 32, an epitope or a variant thereof, the polypeptide of SEQ ID NO: 34, an epitope or a variant thereof, or any human rotavirus C epitope, a polypeptide or protein of the present invention, or a nucleic acid molecule of the invention, alone or in combination with adjuvants, antivirals, antibiotics, analgesic, bronchodilators, or other pharmaceutically acceptable excipients. The present invention further encompasses kits comprising a container containing a pharmaceutical composition of the present invention and instructions for use.

Also provided is a diagnostic kit for detecting human rotavirus C infection that contains human rotavirus C VLPs as reagents for the detection of human rotavirus C antibodies. It is further appreciated that a diagnostic kit optionally includes ancillary reagents such as buffers, solvents, a detectable label and other reagents necessary and recognized in the art for detection of an antibody in a biological sample.

Detection of Anti-Human Rotavirus C Antibodies

Human rotavirus C VLPs are used to detect anti-human rotavirus C antibodies in a biological sample according to embodiments of a process of the present invention.

The term "biological sample" refers to a sample obtained from a biological organism, a tissue, cell, cell culture medium, or any medium suitable for mimicking biological conditions, or from the environment. Non-limiting examples include, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, and vitreal fluid, feces, and nasal secretions. Environmental samples such as sewage or water samples can be used. In a preferred embodiment, the sample is serum, plasma or whole blood.

A process of detecting anti-human rotavirus C antibodies in a biological sample according to the present invention includes contacting a biological sample with recombinant human rotavirus C VLPs and detecting formation of a complex between anti-human rotavirus C antibodies present in the biological sample and the human rotavirus C VLPs. Formation of the complex between anti-human rotavirus C antibodies present in the biological sample and the human rotavirus C VLPs is indicative of exposure of the subject to human rotavirus C sufficient to activate the immune system of the subject to produce anti-human rotavirus C antibodies. Formation of the complex specifically indicates presence of anti-human rotavirus C antibodies since other enteric virus antibodies, particularly anti-human rotavirus A antibodies, do not form a complex with the human rotavirus C VLPs.

In a preferred embodiment, human rotavirus C VLPs are used to detect anti-human rotavirus C antibodies in a biological sample to diagnose current and recent human rotavirus C infection in a subject.

In a further preferred embodiment human rotavirus C VLPs are used in a process of assessing the immune status of an individual with respect to past or present exposure to a human rotavirus C antigen in human rotavirus C infection susceptible organisms, particularly in a human subject.

Detecting formation of a complex between anti-human rotavirus C antibodies present in a biological sample and human rotavirus C VLPs is achieved by any of various methods known in the art, illustratively including detection of a label attached to human rotavirus C VLPs or attached to the anti-human rotavirus C antibodies. The term "label" or "labeled" refers to any composition which can be used to detect, qualitatively or quantitatively, a substance attached to the label. Suitable labels include a fluorescent moiety, a radioisotope, a chromophore, a bioluminescent moiety, an enzyme, a magnetic particle, an electron dense particle, and the like. The term "label" or "labeled" is intended to encompass direct labeling of human rotavirus C VLPs or an antibody by coupling (i.e., physically linking) a detectable substance to the human rotavirus C VLPs or antibody, as well as indirect labeling of the human rotavirus C VLPs or antibody by interaction with another reagent that is directly labeled. An example of indirect labeling of a primary antibody includes detection of a primary antibody using a fluorescently labeled secondary antibody.

Labels used in detection of complex formation depend on the detection process used. Such detection processes are incorporated in particular assay formats illustratively including ELISA, western blot, immunoprecipitation, immunocytochemistry, immuno-fluorescence assay, liquid chromatography, flow cytometry, other detection processes known in the art, or combinations thereof.

In one embodiment, an ELISA is used to detect the presence of human rotavirus C antibodies in a biological sample.

In one configuration of an ELISA for human rotavirus C antibodies, human rotavirus C VLPs are coated on a support such as a microtiter plate, beads, slide, silicon chip or other solid support such as a nitrocellulose or PVDF membrane. A biological sample is incubated with the human rotavirus C VLPs on the support and the presence of complex between antibodies to human rotavirus C and human rotavirus C VLPs is detected by standard ELISA protocols. For example, a complex between human rotavirus C VLPs and human rotavirus C antibodies is detected by reaction of a labeled secondary antibody with the anti-human rotavirus C antibodies and detection of the label.

Another example of an ELISA for human rotavirus C antibodies is a sandwich ELISA. One embodiment of a sandwich ELISA includes depositing a binding antibody onto a solid support. The binding antibody is optionally a non-competing antibody that recognizes human rotavirus C VLPs. The binding antibody is incubated with human rotavirus C VLPs. The complex is washed to remove any unbound material and a detectable label, such as a fluorescently labeled antibody directed to human rotavirus C VLPs, is applied. The detectable label is detected, if present, indicating the presence of anti-human rotavirus C antibody in the biological sample.

Further details of ELISA assays in general are found in Crowther, J. R., The ELISA Guidebook (Methods in Molecular Biology), Humana Press, 2000; and Wild, D., The Immunoassay Handbook, 3rd Edition, Elsevier Science, 2005.

A human rotavirus C antibody detection kit is provided including one or more types of human rotavirus C VLPs and ancillary reagents for use in detecting anti-human rotavirus C antibodies in a biological sample. Ancillary reagents are any signal producing system materials for detection of a complex between an anti-human rotavirus C antibody and a human rotavirus C VLP in any suitable detection process such as ELISA, western blot, immunoprecipitation, immunocytochemistry, immuno-fluorescence, mass spectrometry, or other assay known in the art.

Optionally, an anti-human human rotavirus C antibody assay kit according to embodiments of the present invention includes human rotavirus C VLPs attached to a solid substrate. Suitable solid substrates include, but are not limited to, microtiter plates, chips, tubes, membranes, such as nylon or nitrocellulose membranes, and particles, such as beads. Attachment of protein-containing materials to solid substrates is well-known in the art and includes, but is not limited to, adsorption.

In a preferred embodiment, a human rotavirus C antibody detection kit of the present invention illustratively includes one or more types of human rotavirus C VLPs; and one or more ancillary reagents such as a high binding microtiter plate or other support, blocking agent, washing buffer such as phosphate buffered saline, a labeled anti-immunoglobulin antibody, and matching detection agents, swab or other sample collection devices, control reagents such as labeled non-competing or unlabelled reagents, control nucleotide sequence and relevant primers and probes, and other materials and reagents for detection. The kit optionally includes instructions printed or in electronically accessible form and/or customer support contact information.

Anti-immunoglobulin antibodies in a signal producing system or otherwise are optionally labeled with a fluorophore, biotin, peroxidase, or other enzymatic or non-enzymatic detection label. It is appreciated that a signal producing system may employ an unlabeled primary antibody and a labeled secondary antibody derived from the same or a different organism. It is further appreciated that non-antibody signal producing systems are similarly operable.

It is further appreciated that a kit optionally includes ancillary reagents such as buffers, solvents, a detectable label and other reagents necessary and recognized in the art for detection of an antibody in a biological sample.

VLPs Containing a Cargo

Optionally, the VLP contains a cargo in the internal space defined by the VLP. In particular embodiments, a cargo moiety is a substance to be delivered to a subject or cell. Exemplary cargo moieties include an antigen, a nucleic acid which is not an intact human rotavirus C genome and a therapeutic agent.

Particularly provided is a process of delivery of genetic information whereby genetic material is encapsulated in a human rotavirus C capsid which is then introduced into a host cell. The genetic material is optionally DNA or RNA, or modifications thereof. The genetic information is optionally derived from a human rotavirus C or other viral or nonviral organism, or is synthetic.

A cargo is incorporated in the internal space defined by a human rotavirus C VLP by any of various methods including introducing the cargo into a host cell such that human rotavirus C VLPs are produced in the presence of the cargo and thereby include the cargo in the internal space. Alternatively or additionally, a cargo is incorporated in the internal space by incubating produced human rotavirus C VLPs with the cargo such that the cargo enters the internal space, e.g. by diffusion.

VLP Antibodies

Human rotavirus C VLPs are used as antigens for production of monoclonal or polyclonal antibodies to human rotavirus C for clinical use such as in therapy, analysis or diagnosis; or laboratory research.

In a preferred embodiment, human rotavirus C VLPs are used for eliciting human rotavirus C specific antibody or T cell responses to the VP2, VP6, VP7 or any antigen included in the human rotavirus C VLPs, in vivo (e.g., for protective or therapeutic purposes or for providing diagnostic antibodies) and in vitro (e.g., by phage display technology or another technique useful for generating synthetic antibodies).

As used herein, the terms "antibody" and "antibodies" relate to monoclonal antibodies, polyclonal antibodies, bispecific antibodies, multispecific antibodies, human antibodies, humanized antibodies, chimeric antibodies, camelized antibodies, single domain antibodies, single-chain Fvs (scFv), single chain antibodies, disulfide-linked Fvs (sdFv), and anti-idiotypic (anti-Id) antibodies (including, e.g., anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site. Immunoglobulin molecules are of any type (e.g., IgG, IgE, IgM, IgD, IgA and IgY), class (e.g., IgG1, IgG2, IgG3, IgG4, IgA1 and IgA2), or subclass.

As used herein, the term "antibody fragment" defines a fragment of an antibody that immunospecifically binds to a human rotavirus C virus, any epitope of the human rotavirus C virus or human rotavirus C VLP. Antibody fragments may be generated by any technique known to one of skill in the art. For example, Fab and F(ab')2 fragments may be produced by proteolytic cleavage of immunoglobulin molecules, using enzymes such as papain (to produce Fab fragments) or pepsin (to produce F(ab') 2 fragments). F(ab') 2 fragments contain the complete light chain, and the variable region, the CH 1 region and the hinge region of the heavy chain. Antibody fragments are also produced by recombinant DNA technologies. Antibody fragments may be one or more complementarity determining regions (CDRs) of antibodies.

Human rotavirus C-specific antibodies are provided according to the present invention which specifically bind to human rotavirus C and do not specifically bind to other rotavirus types such as rotavirus A, B, D, E, F and G.

A hybridoma cell line expressing monoclonal antibody raised against human rotavirus C VLPs of the present invention specifically binds to human rotavirus C and does not specifically bind to other rotavirus types such as rotavirus A, B, D, E, F and G.

An antibody raised to human rotavirus C VLPs by any of the methods known in the art, is optionally purified by any method known in the art for purification of an immunoglobulin molecule, for example, by ion exchange chromatography, affinity, particularly by affinity for the specific antigen or size exclusion; centrifugation; differential solubility; or by any other standard techniques for the purification of proteins. It is also appreciated that an inventive antibody or fragments thereof may be fused to heterologous polypeptide sequences known in the art to facilitate purification.

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. (Morrison, 1985, Science, 229:1202; U.S. Pat. Nos. 5,807,715; 4,816,567; and 4,816, 397). Humanized antibodies are antibody molecules from non-human species that bind the desired antigen having one or more complementarity determining regions (CDRs) from the non-human species and framework regions from a human immunoglobulin molecule. Often, framework residues in the human framework regions are substituted with the corresponding residue from the CDR donor antibody to alter, preferably improve, antigen binding. These framework substitutions are identified by methods well known in the art, such as by modeling of the interactions of the CDR and framework residues to identify framework residues important for antigen binding and sequence comparison to identify unusual framework residues at particular positions. (U.S. Pat. No. 5,585, 089; Riechmann et al., 1988, Nature 332:323). Antibodies can be humanized using a variety of techniques known in the art including, for example, CDR-grafting (PCT publication WO 91/09967; U.S. Pat. Nos. 5,225,539; 5,530,101 and 5,585,089), veneering or resurfacing (Studnicka et al., 1994, Protein Engineering 7(6):805 814; Roguska et al., 1994, PNAS. 91:969 973), and chain shuffling (U.S. Pat. No. 5,565, 332).

Completely human antibodies are particularly desirable for therapeutic treatment of human patients. Human antibodies can be made by a variety of methods known in the art including phage display methods described above using antibody libraries derived from human immunoglobulin sequences. (U.S. Pat. Nos. 4,444,887 and 4,716,111).

Human antibodies are readily produced using transgenic mice which are incapable of expressing functional endogenous immunoglobulins, but which can express human immunoglobulin genes.

An inventive antibody is optionally fused or conjugated to heterologous polypeptides may be used in vitro immunoassays and in purification methods such as affinity chromatography. (PCT publication Number WO 93/21232; U.S. Pat. No. 5,474,981).

An inventive antibody is optionally attached to solid supports, which are particularly useful for immunoassays or purification of the polypeptides of the invention or fragments, derivatives, analogs, or variants thereof, or similar molecules having the similar enzymatic activities as the polypeptide of the invention. Such solid supports include, but are not limited to, glass, cellulose, polyacrylamide, nylon, polystyrene, polyvinyl chloride or polypropylene.

Assays for Human Rotavirus C

Anti-human rotavirus C VLP antibodies of the present invention are used to detect human rotavirus C in a biological sample in embodiments of the present invention.

An assay for human rotavirus C in a biological sample of the present invention includes contacting a biological sample with an anti-human rotavirus C antibody and detecting formation of a complex between anti-human rotavirus C antibody and the human rotavirus C present in the biological sample. Formation of the complex is indicative of current infection by human rotavirus C in a subject from which a biological sample is obtained. Formation of the complex specifically indicates presence of human rotavirus C since other rotavirus types such as rotavirus A, B, D, E, F and G, do not form a complex with an anti-human rotavirus C antibody of the present invention.

In a specific embodiment, the processes further involve obtaining a biological sample from a subject, contacting the sample with a compound or agent capable of detecting the presence of human rotavirus C nucleic acid in the sample in order to confirm presence of human rotavirus C in the sample.

In further embodiments, a control sample is assayed for presence of human rotavirus C and/or anti-human rotavirus C antibodies and results are compared with a test sample to ascertain a difference in presence or amount of human rotavirus C or anti-human rotavirus C antibodies.

In another aspect, the invention provides a method of determining exposure of a human or animal to a group C rotavirus comprising: contacting a biological sample of said human or animal with the inventive rotavirus-like particle described herein, under conditions which promote binding of antibodies in said biological sample to said rotavirus-like particles; and detecting binding of antibodies within the biological sample with the rotavirus-like particles. For the purposes of determining exposure of a human or animal to a group C rotavirus, biological sample typically is blood and/or feces;

however, biological sample also includes a sample from other tissues; e.g. an intestinal biopsy.

The invention also encompasses kits for detecting the presence of human rotavirus C in a test sample. The kit, for example, includes an anti-human rotavirus C antibody and optionally includes a reagent such as a labeled secondary antibody or agent capable of detecting an antibody in a complex with a human rotavirus C and, in certain embodiments, for determining the titer in the sample.

Embodiments of inventive compositions and methods are illustrated in the following examples. These examples are provided for illustrative purposes and are not considered limitations on the scope of inventive compositions and methods.

EXAMPLE 1

Cloning and construction of baculovirus recombinants. Segment 5, encoding VP6, from human group C RV strain S-1 was amplified by RT-PCR using BMJ44 (5'-AGC-CAC-ATA-GTT-CAC-ATT-TC-3') (SEQ ID NO: 14) and BMJ141 (5'-ATC-TCA-TTC-ACA-ATG-GAT-G-3') (SEQ ID NO: 15) (28). Segment 8, encoding VP7, from strain S-1 was amplified by RT-PCR using primers BMJ13 (5'-AGC-CAC-ATG-ATC-TTG-TTT-3') (SEQ ID NO: 20) and BMJ14 (5'-GGC-ATT-TAA-AAA-AGA-AGA-3') (SEQ ID NO: 21) (13, 28). Segment 2, encoding VP2, from strain ASP88 was amplified by RT-PCR using BMJ197 (5'-TCG-AGG-ACA-AAT-CGT-CCA-AG-3') (SEQ ID NO: 22) and BMJ180 (5'-AGC-CAC-AGA-GTT-TGA-GGT-C-3') (SEQ ID NO: 23). Cloning and construction of recombinant baculovirus expressing S-1 VP7 was previously described (14). DNA fragments of segment 2 and 5 were cloned into vector pVL1393 and transfections were performed with the Bac-N-Blue transfection kit (Gibco, Grand Island, N.Y.). Baculovirus constructs were amplified in Spodoptera frugiperda 9 (Sf9) cell culture for 2 passages, plaque purified, and then amplified for two more passages in Sf9 cells in serum-free HyQ SFX-Insect media (Hyclone, Logan, Utah).

FIGS. 5A-5B provide an amino acid sequence alignment for VP2 from strain ASP88 described above (SEQ ID NO: 1); human group C VP2 strain referred to as "Bristol" with protein (SEQ ID NO: 16) has NCBI Accession CAC 44890, version CAC 44890.1 GI: 15027005; as well as the porcine VP2 referred to as "Cowden" (SEQ ID NO: 17).

FIGS. 6A-6F show a nucleotide sequence alignment of sequences encoding human Group C VP-2 for inventive strain ASP88 (SEQ ID NO: 18), Cowden porcine strain (SEQ ID No. 44) and Bristol (SEQ ID NO: 19, Accession AJ303139). The start and stop codons are underlined.

FIGS. 7A-7D show a nucleotide sequence alignment of sequences encoding human Group C VP-6 for inventive strain S-1 relative to conventional strains Bristol (SEQ ID NO: 25, Accession CAA42504); Jajeri (SEQ ID NO: 26, Accession AAK26534); CMH004 (SEQ ID NO: 27, Accession ABR31794); V508 (SEQ ID NO: 28, Accession AAX13496); China (SEQ ID NO: 29, Accession BAB83829); and BCN6 (SEQ ID NO: 30, Accession CAJ41549). It is noted that FIGS. 7A-7D provide the sequence comparison in a format standard in the art wherein a "dot" indicates identity with a reference sequence. In FIGS. 7A-7D, the reference sequence is a consensus sequence (SEQ ID No. 41).

FIGS. 8A-8B show an amino acid sequence alignment of sequences encoding human Group C VP-6 for inventive strain S-1 (SEQ ID NO: 32) relative to conventional strains Bristol (SEQ ID NO: 34, Accession CAA42504); Jajeri (SEQ ID NO: 35, Accession AAK26534); CMH004 (SEQ ID NO: 36, Accession ABR31794); V508 (SEQ ID NO: 37, Accession AAX13496); China (SEQ ID NO: 38, Accession BAB83829); and BCN6 (SEQ ID NO: 39, Accession CAJ41549). It is noted that FIGS. 8A-8B provide the sequence comparison in a format standard in the art wherein a "dot" indicates identity with a reference sequence. In FIGS. 8A-8B, the reference sequence is a consensus sequence (SEQ ID No. 24).

TABLE I

Comparison of VP2 Genes of Group C Rotaviruses

|  | Asp88 | Bristol[3] | Cowden[2] |
|---|---|---|---|
| ORF | 2652 | 2652 | 2652 |
| Size (aa) | 884 | 884 | 884 |
| MW (kDa)[4] | 101.57 | 101.67 | 101.68 |
| Nucleotide and amino acid homology | | | |
| Asp88 | — | 97.2 | 83.2 |
| Bristol | 98.5 | — | 82.9 |
| Cowden | 92.8 | 92.6 | — |

Table I shows results of a comparison of VP2 Genes of Group C rotaviruses. MEGA version 4 program was used for the sequence analysis of the VP2 genes containing a single ORF extending from nt 37-2688. Results indicate that the nucleotide sequence encoding Asp88 VP2 has 97.2% homology to the nucleotide sequence encoding Bristol VP2, the nucleotide sequence encoding Asp88 VP2 has 83.2% homology to the nucleotide sequence encoding Cowden (porcine) VP2, and the nucleotide sequence encoding Bristol VP2 has 82.9% homology to the nucleotide sequence encoding Cowden VP2. Further, the amino acid sequence of Asp88 VP2 has 98.5% homology to the amino acid sequence of Bristol VP2, the amino acid sequence of Asp88 VP2 has 92.8% homology to the amino acid sequence of Cowden (porcine) VP2, and the amino acid sequence of Bristol VP2 has 92.6% homology to the amino acid sequence of Cowden VP2. Accession numbers of group C rotavirus Bristol strain is AJ303139. [2]Cowden VP2 sequence was resequenced. [3]Bristol sequence is found in Chen, Z. et al, 2002.

EXAMPLE 2

Cells and superinfections. Sf9 or High Five (Hi5) insect cells were grown and maintained in EX-CELL 420 or 405 media (Sigma, Lenexa, Kans.) or HyQ SFX-INSECT media in shaker flasks at 27° C. Sf9 and Hi5 cells were subcultured every 3 or 4 days at a concentration of $1 \times 10^6$ cells/ml and $5 \times 10^5$ cells/ml, respectively. Stationary superinfections were performed by seeding Sf9 cells in HyQ or EX-CELL 420 and Hi5 cells in HyQ or EX-CELL 405 into a T150 flask at a concentration of $3 \times 10^5$ cells/ml. Baculovirus constructs (rVP2, rVP6 and rVP7) were added at a multiplicity of infection (MOI) of 1 each. Infections were carried out without proteinase inhibitors and infected cultures were harvested at day 5. Large scale VLP production was performed in suspension culture by seeding Sf9 cells in EX-CELL 420 into fernbach flasks at a concentration of $1 \times 10^6$ cells/ml. Baculovirus recombinants were added one day later at an MOI of 1.4 each and harvested on day 4.

EXAMPLE 3

Western blot. Sodium dodecyl sulfate-polyacrylamide gel electrophoresis (SDS-PAGE) was carried out with 12% separating and 5% stacking gels using the Laemmli discontinuous buffer system (16). Samples were heated at 97° C. for 5 min with 10% β-mecaptoethanol prior to loading and then electrophoresed. Proteins were transferred to a PVDF membrane in transfer buffer (25 mM Tris, 192 mM glycine, 10% methanol). After blocking with 10% (for unpurified GpC RV proteins) blotto in PBS-T for 1-2 hrs at room temperature or 15% (for purified GpC RV proteins) blotto in PBS-T overnight at 4° C., membranes were incubated with porcine hyperimmune serum (1:2,000) to Cowden in 5% blotto in PBS-T overnight at 4° C. or rabbit hyperimmune serum (1:20,000) to human GpC VLPs in 10% blotto in PBS-T for 1 h. Membranes were washed in PBS-T, incubated with horseradish peroxidase (HRP) goat anti-pig (1:142,000) (KPL, Gaithersburg, Md.) in 5% blotto or HRP-goat anti rabbit (1:20,000) (Pierce, Rockford, Ill.) in 10% blotto. GpC RV proteins were visualized with Supersignal West Femto Maximum Sensitivity Substrate Kit (Pierce, Rockford, Ill.) by exposing membranes to film and processing with medical film processor SRX-101A (Konica Minolta, Jakarta, Indonesia).

EXAMPLE 4

Purification of VLPs. Infected cell cultures were clarified twice at 15,344×g for 30 min at 4° C. with a JA-14 rotor in J2-MC centrifuge. Clarified supernatants were layered over 35% sucrose cushions and centrifuged for two hrs at 107,000×g (4° C.) with the SW32Ti rotor in an Optima L-80 XP Ultracentrifuge (Beckman Coulter, Fullerton, Calif.). Pellets were resuspended in TNC buffer (10 mM Tris pH 7.4, 140 mM NaCl, 5 mM CaCl2), re-clarified in a microcentrifuge and treated twice sequentially with equal volume Vertrel (Miller-Stephenson, Danbury, Conn.). Samples were centrifuged 10 min at 2,095×g (4° C.) with a SX4750A rotor in the Allegra X-12R tabletop centrifuge (Beckman Coulter, Fullerton, Calif.). The aqueous layer was overlaid on top of a CsCl solution (1.2738 g/ml) and centrifuged 17-18 hrs at 111,000×g (4° C.) with the SW40Ti rotor. Fractions that contained VLPs were collected, diluted in TNC, and pelleted out by centrifugation at 107,000×g (4° C.) for 1 hr in the SW32Ti rotor. Particles were resuspended in Hanks balanced salt solution (Gibco, Grand Island, N.Y.) supplemented with 10% sorbitol.

EXAMPLE 5

Electron microscopy and immunoelectron microscopy. GpC RV VLPs were examined by electron microscopy (EM) and immunoelectron microscopy (IEM) as previously described with modifications (19). Briefly, 1% ammonium molybdate-1% trehalose in water (pH 6.95) was used to provide negative contrast on specimens adsorbed to nickel formvar-carbon filmed grids (9). Each grid was pretreated with 1% alcian blue 8GX in water to enhance hydrophilicity and provide cationic charges to the film surface prior to applying specimens. IEM was done by mixing 1 μl of purified GpC RV VLPs or GpA RV RRV with 1 μl of rabbit antibody to GpA or GpC RV diluted 1:500 and applying to nickel formvar-carbon coated grids. After incubation for 0.5-1 hr, the grids were blotted with filter paper, rinsed with 0.1 M Tris buffer supplemented with 0.4% acetylated bovine serum albumin (BSA) (Aurion, Hatfield, Pa.), and incubated for 30 min with goat anti-rabbit secondary antibody conjugated to 6 nm colloidal gold (1:20). Grids were rinsed twice with Tris buffer without BSA and with deionized water, blotted, stained with ammonium molybdate-trehalose, and viewed within an FEI Technai BioTwin transmission electron microscope at 120 KV accelerating voltage. Images were captured digitally with a 2K×2K AMT digital camera.

EXAMPLE 6

Production of antisera to GpC VLPs. Rabbits (Covance, Denver, Pa.) were screened for the presence of GpA and C RV antibodies by antigen capture EIA prior to immunization. Rabbit CD94, which tested negative for GpA and C antigens, was selected for antibody production. CD94 was injected subcutaneously with 50 μg GpC VLPs formulated in Freud's complete adjuvant. Subsequent doses formulated with Freud's incomplete adjuvant were administered three weeks after the previous injection. Five injections in total were administered. The first bleed was 10 days after dose two and all subsequent bleeds were scheduled three weeks after the previous bleed. All bleeds tested positive for GpC RV antibody and were pooled.

EXAMPLE 7

Enzyme Immunoassays (EIAs). 96-well plates were coated with 100 μl supernatant from GpA RRV infected MA104 cell cultures or GpC VLPs in recombinant baculovirus-infected Sf9 cells diluted (1:100) in coating buffer and incubated overnight at 37° C. Plates were washed with PBS-T and then blocked with 150 μl 5% blotto for 1 hr at 37° C. Plates were washed and then incubated with 100 of serially diluted hyperimmune serum from rabbits CD94, CD8, and 8807A in diluent (1% blotto, 0.5% polyoxethylene ether W1 in PBS) for 2 hrs at 37° C. Rabbit CD8 was immunized with GpA RV RRV, whereas rabbit 8807A was naturally infected with GpA RV and also immunized with GpC RV Cowden. Plates were washed and then incubated with HRP goat anti-rabbit IgG (KPL, Gaithersburg, Md.) diluted (1:3,000) in diluent for 1 hr at 37° C. Plates were washed 6 times with PBS-T and then reacted with 100 μl of tetramethyl benzidine (TMB) for 10 min. Reactions were stopped with 100 μl 1N HCl and plates were read at Abs450. Antibody titers were defined as the reciprocal of the highest dilution of serum giving a net optical density (OD) value (OD with virus minus OD with blotto) above 0.1.

EXAMPLE 8

Kinetics of GpC RV protein synthesis in Sf9 and Hi5 cells. Sf9 and Hi5 cells in EX-CELL or HyQ media were infected with GpC RV VP2, VP6, and VP7 baculovirus recombinants at an MOI of 1 each and infected cultures were harvested on days 3, 4 and 5. Infected cultures were clarified and analyzed by Western blot using Cowden specific porcine hyperimmune serum to determine the expression profiles of proteins secreted into the supernatant. FIGS. 1A and 1B are electrophoretic gels showing the kinetics of GpC RV VP6 and VP7 expression in Sf9, FIG. 1A, or Hi5, FIG. 1B, cells in different media. In both FIGS. 1A and 1B, lane 1, Cowden strain; lanes 2-5, infected cultures in HyQ harvested 0, 3-5 dpi; and lanes 6-9, infected cultures in EX-CELL harvested at 0, 3-5 dpi. GpC RV VP6 and VP7 are indicated on the right. Molecular markers 54 kDa and 37.5 kDa are indicated by arrows on the left.

Expression of GpC RV VP6 and VP7 increased with time, with the highest levels seen at 4 or 5 days post infection (dpi) in Sf9 and Hi5 cells. Use of EX-CELL media resulted in higher rotavirus protein yields in both cell lines. Higher protein expression was achieved in EX-CELL media than in HyQ medium and similar levels of protein expression were observed in Sf9 and Hi5 cells. The cell line Sf9 and EX-CELL 420 were used in further examples of GpC RV protein production described herein. Human GpC RV VP2 was not detectable with the serum used.

EXAMPLE 9

Self-assembly and characterization of GpC RV VLPs. Superinfections of Sf9 cells with rVP2, rVP6 and rVP7 at an MOI of 1 each resulted in the formation of intact GpC RV VLPs that have the structural order of typical rotavirus.

FIG. 2A is an image of an electron micrograph showing VLPs purified from cultures of Sf9 cells in EX-CELL 420 medium that were infected with recombinant baculoviruses encoding human rotavirus C VP2, VP6, and VP7 at an MOI of 1 each. FIG. 2B is an image of an electron micrograph showing VLPs purified from cultures of Sf9 cells in EX-CELL 420 medium that were infected with recombinant baculoviruses encoding human rotavirus C VP6 and VP7 at an MOI of 1.4 each. VLPs shown in FIGS. 2A and 2B were stained with 5% ammonium molybdate-1% trehalose. The bar in FIGS. 2A and 2B represents 100 nm.

Sf9 cells were also superinfected with all three recombinant viruses at various MOIs (0.1, 0.2, 1 and 2 each) in order to optimize conditions for VLP production. EM analysis of supernatants demonstrated better VLP formation in superinfections performed at the higher MOIs of 1 and 2. To determine if VP2 is essential for VLP formation, superinfections were performed with and without rVP2 and analysis was performed by EM. Because robust VLP formation was demonstrated without rVP2, all subsequent experiments were performed excluding this recombinant.

Biochemical composition and antigenicity of purified VP6/7 VLPs were compared with a GpA RV strain, YK-1, by SDS-PAGE and Western blot. Images comparing major structural viral proteins from GpA RV YK-1 and GpC VLPs by SDS-PAGE and Western blot are shown in FIGS. 3A and 3B, respectively.

Proteins from purified YK-1 (lane 1) and VLPs (lane 2) were separated on a 12% SDS-PAGE and stained by coomassie blue, FIG. 3A, or analyzed by Western blot, FIG. 3B. For western blot, proteins were transferred to a PVDF membrane and incubated with rabbit hyperimmune serum to GpC VLPs. GpC RV VP6 and VP7 are indicated on the right. Arrows indicate molecular weight markers 54 kDa and 37.5 kDa.

Human GpC recombinant proteins VP6 and VP7 migrate at similar molecular weights and are present at similar ratios as seen in GpA YK-1, indicating a proper molar ratio in assembled VLPs, illustrate in FIG. 3A. Western blot performed with human GpC VLP specific antibody demonstrated that these human rotavirus C VLPs were antigenic and of good quality, illustrated in FIG. 3B.

EXAMPLE 10

Antigenic reactivity of GpC RV antibody. Rabbit polyclonal antibody was produced to purified human rotavirus C VLPs. Prior to immunization, rabbit CD94 had no antibody to GpA or C RV and after inoculations developed a high antibody titer to GpC RV (Table II). In controls, rabbit CD8, immunized with RRV, gave strong positive response to GpA RV, whereas rabbit 8807A, which was naturally infected with GpA RV and immunized with GpC RV Cowden strain, had similar antibody titers to GpA and GpC RV antigens. Hyperimmune serum from rabbit CD94 was utilized to enhance EIA that employs only porcine hyperimmune sera (8). This assay proved to specifically detect GpC RV antigens (VLPs and Cowden) but did not react with other control samples, such as MA104, Sf9 cells, and GpA RV RRV.

TABLE II

Antibody Titers in Hyperimmune Sera to GpA and C Rotaviruses

| | | Reciprocal of IgG Titer | | | |
|---|---|---|---|---|---|
| | Rotavirus | Group A (RRV) | | Group C (VLPs) | |
| Rabbit | Antigen | Pre | Post | Pre | Post |
| CD94 | GpC VLPs | <100 | <100 | <100 | 51,200 |
| CD8 | GpA RRV | ND | 25,600 | ND | <100 |
| 8807A | GpC Cowden & GpA | ND | 1,600 | ND | 3,200 |

Hyperimmune sera were tested and antibody titers were determined as described in the text.
Pre = pre-immunization serum.
Post = post-immunization serum.
ND = not determined.

Human GpC RV VLPs were further characterized by examining their antigenic properties with immunoelectron microscopy using rabbit hyperimmune sera to GpA and C RV FIG. 4A shows GpC RV VLPs immunostained with GpC-specific rabbit hyperimmune serum. FIG. 4B shows GpC RV VLPs immunostained with GpA-specific rabbit hyperimmune serum. FIG. 4C shows GpA RV immunostained with GpC-specific rabbit hyperimmune serum. FIG. 4D shows GpA RV immunostained with GpA-specific rabbit hyperimmune serum. GpC RV VLPs were specifically labeled with GpC-specific hyperimmune serum and GpA RVs were heavily coated with GpA-specific hyperimmune serum. The bar in FIGS. 4A, 4B, 4C and 4D represents 100 nm.

GpC RV antibody specifically reacted with human GpC VLPs but not with GpA RV, RRV. Correspondingly, GpA antibody exhibited specific reactivity with RRV and not with GpC VLPs. These results indicate the occurrence of group-specific interactions between RV antigen and antibody and confirm the absence of cross-reactivities between GpA and GpC RV reagents.

[VP2 from human strain Asp88-amino acid sequence]

(SEQ ID NO: 1)

```
MISRNRRRNNQQKDIGKEKQLETIIDKEVKENKDSTKEDKLVVTEESNGDVTAVKEQSN
NINLQKNDLVKEVMNIQNQTLNTVVAENKVEIEEIVKKYIPSYNTDSLIVKKLTEIQESSA
KTYNTLFRLFTPVKSYLYDINGEKKLSTRWYWKLLKDDLPAGDYSVRQFFLSLYLNVLE
GMPDYIMLRDMAVDNPYSAEAGKIVDGKSKEILVELYQDQMTEGYIRRYMSELRHKIS
GETNTAKYPAILHPVDNELNQYFLEHQLIQPLTTRNIAELIPTQLYHDPNYVFNIDAAFLT
NSRFVPPYLTQDRIGLHDGFESIWDSKTHADYVSARRFIPDLTELVDAEKQIKEMAAHLQ
LEAITVQVESQFLAGISAAAANEAFKFIIGSVLSTRTIAVEFITSNYMSLASCMYLMTIMPS
EIFLRESLVAMRLAIINTLIYPALGLAQMHYQAGEVRTPFELAEMRVANRSIRQWLHHC
NTLQFGRQITEGIIHLRFTNDIMTGRIVNLFSTMLVALSSQPFATYPLDYKRSVQRALQLL
SNRTAQIADLTRLIVYNYTTLSACIVMNMHLVGTLTVERIQATSLTSLMMLISNKTVIPEP
SSLFSYFSSNINFLTNYNEQIDNVVAEIMAAYRLNLYQQKMLMLVTRFVSRLYIFDAPKI
PPDQMYRLRNRLRNIPVERRRADVFRIIMNNRDLIEKTSERICQGVLLSYTPMPLTYVED
VGLTNVINDTNNFQIINIEEIEKTGDYSAITNALLRDTPIILKGAIPYVTNSSVIDVLSKVDT
```

-continued

TVFASIVKDRDISKLKPIKFIINSDSSEYYLVHNNKWTPTTTTAVYKARSQQFDIQHSVSM
LESNLFFVVYNDLFKYIKTTTVLPINAVSYDGARIMQET

[VP2 from human strain ASP88-nucleotide sequence]

(SEQ ID N

-continued

```
CAGCCTTTTTAACAAATTCAAGATTTGTTCCACCATACTTAACACAGGAT
AGGATTGGATTACATGATGGATTCGAATCAATATGGGATTCAAAAACCCA
TGCTGATTACGTTTCAGCTAGAAGATTTATACCTGATTTAACTGAACTGG
TAGATGCTGAAAAGCAAATAAAAGAAATGGCTGCACATTTACAACTAGAG
GCTATTACAGTACAGGTTGAATCACAATTTTTAGCGGGAATTAGTGCTGC
TGCAGCTAATGAAGCGTTCAAATTTATAATTGGCTCAGTTTTATCTACCA
GAACAATAGCTGTAGAATTCATAACCTCAAACTATATGTCGTTAGCATCA
TGTATGTATTTAATGACTATTATGCCATCAGAGATTTTCTTGAGAGAATC
ATTAGTTGCTATGCGATTAGCAATAATAAATACCCTTATTTATCCAGCTC
TAGGTTTAGCGCAAATGCATTATCAAGCAGGTGAAGTGAGGACCCCATTC
GAATTAGCTGAGATGCGAGTAGCTAATAGATCTATTAGACAATGGTTACA
TCATTGTAATACACTTCAATTTGGTAGACAGATAACGGAAGGGATAATTC
ATCTACGATTTACTAATGATATCATGACAGGTAGGATAGTGAACTTATTT
TCAACAATGCTAGTAGCTTTATCATCTCAGCCATTCGCTACATATCCTTT
AGACTATAAAGATCTGTACAAAGAGCATTACAACTTTTATCAAATAGAA
CAGCCCAAATAGCAGATTTAACCAGATTAATAGTATACAATTATACTACA
TTATCTGCATGTATAGTCATGAATATGCATTTAGTAGGAACTCTTACTGT
TGAACGTATACAGGCCACTTCTCTAACTTCTTTAATGATGTTAATTTCTA
ATAAGACAGTTATTCCAGAACCATCGTCTCTTTTTTCATATTTCTCTAGT
AACATTAATTTTCTTACAAATTATAATGAGCAAATTGATAATGTGGTAGC
AGAAATAATGGCCGCATATAGATTGAATTTATATCAACAGAAAATGTTGA
TGCTCGTTACCAGGTTTGTGTCAAGGTTGTACATATTTGATGCTCCTAAA
ATACCGCCAGATCAGATGTATAGATTAAGAAACCGATTAAGAAATATTCC
AGTTGAAAGAAGAAGAGCTGATGTGTTCAGAATTATTATGAATAATAGAG
ATTTAATCGAAAAACATCAGAACGTATATGTCAGGGTGTGTTGTTATCT
TATACACCAATGCCTTTAACTTACGTTGAAGATGTCGGGTTAACAAATGT
AATTAATGACACTAATAACTTCCAAATAATTAATATAGAAGAAATTGAGA
AGACCGGTGACTATTCAGCCATAACGAATGCATTACTTCGGGATACTCCA
ATTATATTGAAAGGTGCGATTCCATATGTTACTAACTCATCAGTAATTGA
TGTTTTATCTAAAGTGGACACCACAGTGTTCGCAAGCATCGTAAAAGATA
GGGATATTTCAAAGTTAAAACCAATAAAATTCATAATTAATTCAGATTCA
TCCGAATATTATTTAGTACACAATAATAAATGGACACCAACAACAACTAC
AGCAGTATATAAAGCTAGATCTCAGCAATTTGATATACAACATTCAGTAT
CAATGCTAGAGTCAAACTTATTTTTTGTGGTATATAATGATTTATTTAAA
TACATTAAAACCACTACAGTTCTGCCGATAAATGCTGTCTCTTATGATGG
TGCAAGAATTATGCAAGAAACATAA
```

VP2 from human strain ASP88-nucleotide sequence including 36 5' non-coding bases (SEQ ID NO: 43)

GGCTTAAAAAGATCAG
TCGAGGACAAATCGTCCAAGATGATAAGCAGAAACAGGCGCAGAAATAAC
CAACAAAAAGATATAGGAAAAGAGAAACAATTAGAGACTATAATTGACAA
AGAAGTAAAGGAAAACAAAGATTCTACAAAAGAAGATAAGCTAGTAGTTA
CGGAAGAAAGTAATGGTGACGTCACAGCTGTTAAAGAACAATCGAATAAT
ATTAATTTACAAAAGAATGATTTGGTTAAAGAAGTCATGAATATACAGAA
TCAAACATTAAATACAGTAGTTGCTGAGAATAAAGTTGAAATAGAAGAAA
TAGTTAAAAAATACATTCCCTCATATAATACTGACAGCCTTATTGTTAAA
AAGTTAACTGAAATCCAGGAATCAAGTGCTAAAACATATAATACATTATT
CAGATTATTTACTCCAGTTAAAAGTTATTTATATGACATAAATGGTGAGA
AAAAATTATCGACTAGATGGTATTGGAAATTGCTCAAAGATGATTTACCT
GCTGGTGATTACTCAGTTAGACAATTCTTCCTGTCACTATATTTAAATGT
TTTAGAGGGAATGCCCGATTACATAATGCTTCGTGATATGGCAGTGGATA
ACCCATATTCAGCAGAAGCAGGTAAAATCGTAGATGGAAAGTCTAAAGAA
ATTTTAGTTGAACTATATCAAGACCAAATGACAGAAGGGTATATTAGAAG
ATATATGTCTGAATTAAGACATAAAATATCTGGAGAAACAAATACTGCAA
AATATCCAGCTATTCTACATCCCGTGGATAATGAGCTTAATCAATACTTT
CTTGAGCATCAGTTAATTCAACCATTAACTACAAGAAATATTGCAGAATT
GATTCCAACTCAATTATATCATGATCCAAATTACGTTTTTAATATTGATG
CAGCCTTTTTAACAAATTCAAGATTTGTTCCACCATACTTAACACAGGAT
AGGATTGGATTACATGATGGATTCGAATCAATATGGGATTCAAAAACCCA
TGCTGATTACGTTTCAGCTAGAAGATTTATACCTGATTTAACTGAACTGG
TAGATGCTGAAAAGCAAATAAAAGAAATGGCTGCACATTTACAACTAGAG
GCTATTACAGTACAGGTTGAATCACAATTTTTAGCGGGAATTAGTGCTGC
TGCAGCTAATGAAGCGTTCAAATTTATAATTGGCTCAGTTTTATCTACCA
GAACAATAGCTGTAGAATTCATAACCTCAAACTATATGTCGTTAGCATCA
TGTATGTATTTAATGACTATTATGCCATCAGAGATTTTCTTGAGAGAATC
ATTAGTTGCTATGCGATTAGCAATAATAAATACCCTTATTTATCCAGCTC
TAGGTTTAGCGCAAATGCATTATCAAGCAGGTGAAGTGAGGACCCCATTC
GAATTAGCTGAGATGCGAGTAGCTAATAGATCTATTAGACAATGGTTACA
TCATTGTAATACACTTCAATTTGGTAGACAGATAACGGAAGGGATAATTC
ATCTACGATTTACTAATGATATCATGACAGGTAGGATAGTGAACTTATTT
TCAACAATGCTAGTAGCTTTATCATCTCAGCCATTCGCTACATATCCTTT
AGACTATAAAAGATCTGTACAAAGAGCATTACAACTTTTATCAAATAGAA
CAGCCCAAATAGCAGATTTAACCAGATTAATAGTATACAATTATACTACA
TTATCTGCATGTATAGTCATGAATATGCATTTAGTAGGAACTCTTACTGT
TGAACGTATACAGGCCACTTCTCTAACTTCTTTAATGATGTTAATTTCTA
ATAAGACAGTTATTCCAGAACCATCGTCTCTTTTTTCATATTTCTCTAGT
AACATTAATTTTCTTACAAATTATAATGAGCAAATTGATAATGTGGTAGC
AGAAATAATGGCCGCATATAGATTGAATTTATATCAACAGAAAATGTTGA
TGCTCGTTACCAGGTTTGTGTCAAGGTTGTACATATTTGATGCTCCTAAA

-continued
ATACCGCCAGATCAGATGTATAGATTAAGAAACCGATTAAGAAATATTCC
AGTTGAAAGAAGAAGAGCTGATGTGTTCAGAATTATTATGAATAATAGAG
ATTTAATCGAAAAAACATCAGAACGTATATGTCAGGGTGTGTTGTTATCT
TATACACCAATGCCTTTAACTTACGTTGAAGATGTCGGGTTAACAAATGT
AATTAATGACACTAATAACTTCCAAATAATTAATATAGAAGAAATTGAGA
AGACCGGTGACTATTCAGCCATAACGAATGCATTACTTCGGGATACTCCA
ATTATATTGAAAGGTGCGATTCCATATGTTACTAACTCATCAGTAATTGA
TGTTTTATCTAAAGTGGACACCACAGTGTTCGCAAGCATCGTAAAAGATA
GGGATATTTCAAAGTTAAAACCAATAAAATTCATAATTAATTCAGATTCA
TCCGAATATTATTTAGTACACAATAATAAATGGACACCAACAACAACTAC
AGCAGTATATAAAGCTAGATCTCAGCAATTTGATATACAACATTCAGTAT
CAATGCTAGAGTCAAACTTATTTTTTGTGGTATATAATGATTTATTTAAA
TACATTAAAACCACTACAGTTCTGCCGATAAATGCTGTCTCTTATGATGG
TGCAAGAATTATGCAAGAAACATAAATGATTGTATAGTATCATCTTGTAA
CGACCTCAAACTCTGTGGCT

[VP6 from human strain S-1-nucleotide sequence]
(SEQ ID NO: 31)
```
         *   20    *   40    *   60    *   80
ATGGATGTACTTTTTTCTATAGCGAAAACCGTGTCAGATCTTAAAGAGAAAGTTGTAGTTGGAACAATTTATACTAATGT

*  100    *  120    *  140    *  160
AGAAGATGTTGTACAACAGACGAATGAATTGATTAGAACTTTGAATGGAAATATTTTTCATACTGGTGGCATTGGAACAC

*  180    *  200    *  220    *  240
AGCCTCAGAAAGAGTGGAATTTTCAGCTCCCACAATTGGGTACCACTTTATTAAATTTAGATGATAATTATGTTCAATCA

*  260    *  280    *  300    *  320
ACTAGAGGCATAATTGATTTTTTATCATCTTTTATAGAAGCTGTATGTGATGATGAAATTGTTAGAGAAGCTTCAAGAAA

*  340    *  360    *  380    *  400
TGGTATGCAACCTCAATCACCAGCTCTTATATTATTATCTTCATCAAAATTTAAAACAATTAATTTTAATAATAGTTCTC

*  420    *  440    *  460    *  480
AATCTATCAAAAATTGGAATGCTCAATCAAGACGTGAGAATCCTGTATATGAGTACAAAAATCCAATGTTGTTTGAATAT

*  500    *  520    *  540    *  560
AAAAATTCTTATATTTTACAACGCGCAAATCCACAATTTGGAAGCGTCATGGGTTTAAGATATTATACAACAAGTAATAT

*  580    *  600    *  620    *  640
TTGTCAAATTGCAGCATTTGATTCCACCCTAGCTGAAAATGCACCAAATAATACGCAACGCTTCGTTTATAATGGCAGAC

*  660    *  680    *  700    *  720
TAAAAAGACCCATATCAAATGTTTTAATGAAAATAGAAGCTGGTGCTCCAAATATAAGCAACCCAACTATTTTACCTGAT

*  740    *  760    *  780    *  800
CCTAATAATCAAACAACTTGGCTTTTTAATCCGGTACAATTAATGAATGGAACATTTACCATTGAATTCTATAATAATGG

*  820    *  840    *  860    *  880
TCAACTAATTGATATGGTTCGAAATATGGGAATAGTTACTGTAAGAACTTTTGATTCTTATAGAATAACAATTGACATGA

*  900    *  920    *  940    *  960
TTAGACCAGCTGCTATGACTCAATACGTTCAACGAATTTTTCCACAAGGTGGACCTTATCATTTTCAGGCTACATATATG

*  980    *  1000   *  1020   *  1040
TTAACATTAAGTATATTAGATGCTACCACAGAGTCCGTTCTATGTGATTCTCATTCAGTAGAATATTCAATAGTAGCAAA

*  1060   *  1080   *  1100   *  1120
CGTCAGAAGAGATTCAGCAATGCCAGCTGGAACTGTTTTTCAACCGGGATTTCCATGGGAACACACACTATCCAATTACA

*  1140   *  1160   *  1180
CTGTTGCTCAAGAAGATAATTTAGAAAGATTATTGTTAATCGCATCTGTGAAGAGAATGGTAATG
```

[VP6 from human strain S-1-amino acid sequence]
(SEQ ID NO: 32)
```
MDVLFSIAKTVSDLKEKVVVGTIYTNVEDVVQQTNELIRTLNGNIFHTGG           [50]
IGTQPQKEWNFQLPQLGTTLLNLDDNYVQSTRGIIDFLSSFIEAVCDDEI          [100]
VREASRNGMQPQSPALILLSSSKFKTINFNNSSQSIKNWNAQSRRENPVY          [150]
EYKNPMLFEYKNSYILQRANPQFGSVMGLRYYTTSNICQIAAFDSTLAEN          [200]
APNNTQRFVYNGRLKRPISNVLMKIEAGAPNISNPTILPDPNNQTTWLFN          [250]
PVQLMNGTFTIEFYNNGQLIDMVRNMGIVTVRTFDSYRITIDMIRPAAMT          [300]
QYVQRIFPQGGPYHFQATYMLTLSILDATTESVLCDSHSVEYSIVANVRR          [350]
DSAMPAGTVFQPGFPWEHTLSNYTVAQEDNLERLLLIASVKRMVM               [395]
```

[VP7 from human strain S-1-nucleotide sequence]
(SEQ ID NO: 33)
>gi|1314237|gb|U20995.1|RGU20995 Human rotavirus group C isolate S-1 outer
capsid glycoprotein (VP7) gene, complete cds
GGCATTTAAAAAGAAGAAGCTGTCTGACAAACTGGTCTTCTTTTTAAATGGTTTGTACAACATTGTACA
CTGTTTGCGCCATTCTCTTCATTCTTTTCATTTATATATTATTATTTAGAAAAATGTTCCACCTAATAAC
TGATACTTTAATAGTGATGCTTATTTTATCTAATTGTGTAGAGTGGTCACAAGGTCGATGTTTATTGAT -continued

```
GATATACATTATAATGGTAACGTTGAGACTATCATAAATTCTACTGATCCTTTTAATGTTGAATCTTTAT
GTATTTATTTTCCAAATGCAGTTGTAGGATCACAGGGACCAGGTAAATCCGATGGACATTTGAATGATGG
TAATTATGCACAGACTATCGCCACTTTGTTTGAAACAAAAGGATTCCCAAAAGGTTCAATAATAATTAAA
ACATATACACAGACATCAGACTTTATAAATTCAGTAGAAATGACATGCTCTTATAATATAGTTATCATTC
CTGATAGCCCAAATGATTCAGAATCTATTGAACAGATAGCAGAATGGATTTTAAATGTTTGGAGATGTGA
TGACATGAATTTGGAAATTTATACTTATGAACAAATTGGAATAAACAATTTATGGGCTGCATTTGGTAGT
GACTGTGATATATCTGTCTGTCCATTAGATACTACAAGTAATGGAATCGGATGTTCACCAGCTAGTACAG
AAACTTATGAAGTTGTATCAAATGACACCCAATTGGCCTTAATTAATGTTGTGGATAATGTTAGACATAG
AATACAGATGAACACTGCTCAATGTAAATTGAAAAATTGTATTAAGGGTGAAGCTCGACTGAATACTGCA
CTAATAAGAATTTCAACATCATCAAGTTTTGATAATTCATTGTCACCATTAAATAACGGCCAAACAACAA
GATCGTTTAAAATAAATGCAAAGAAATGGTGGACTATATTTTATACAATAATTGATTATATTAATACAAT
TGTACAATCAATGACTCCCAGACATCGGGCGATTTATCCAGAAGGGTGGATGTTGAGGTATGCGTAAACA
AGATCATGTGGCT
```

[VP7 from human strain S-1-nucleotide sequence of open reading frame]
(SEQ ID NO: 45)

```
ATGGTTTGTACAACATTGTACA
CTGTTTGCGCCATTCTCTTCATTCTTTTCATTTATATATTATTATTTAGAAAAATGTTCCACCTAATAAC
TGATACTTTAATAGTGATGCTTATTTTATCTAATTGTGTAGAGTGGTCACAAGGTCAGATGTTTATTGAT
GATATACATTATAATGGTAACGTTGAGACTATCATAAATTCTACTGATCCTTTTAATGTTGAATCTTTAT
GTATTTATTTTCCAAATGCAGTTGTAGGATCACAGGGACCAGGTAAATCCGATGGACATTTGAATGATGG
TAATTATGCACAGACTATCGCCACTTTGTTTGAAACAAAAGGATTCCCAAAAGGTTCAATAATAATTAAA
ACATATACACAGACATCAGACTTTATAAATTCAGTAGAAATGACATGCTCTTATAATATAGTTATCATTC
CTGATAGCCCAAATGATTCAGAATCTATTGAACAGATAGCAGAATGGATTTTAAATGTTTGGAGATGTGA
TGACATGAATTTGGAAATTTATACTTATGAACAAATTGGAATAAACAATTTATGGGCTGCATTTGGTAGT
GACTGTGATATATCTGTCTGTCCATTAGATACTACAAGTAATGGAATCGGATGTTCACCAGCTAGTACAG
AAACTTATGAAGTTGTATCAAATGACACCCAATTGGCCTTAATTAATGTTGTGGATAATGTTAGACATAG
AATACAGATGAACACTGCTCAATGTAAATTGAAAAATTGTATTAAGGGTGAAGCTCGACTGAATACTGCA
CTAATAAGAATTTCAACATCATCAAGTTTTGATAATTCATTGTCACCATTAAATAACGGCCAAACAACAA
GATCGTTTAAAATAAATGCAAAGAAATGGTGGACTATATTTTATACAATAATTGATTATATTAATACAAT
TGTACAATCAATGACTCCCAGACATCGGGCGATTTATCCAGAAGGGTGGATGTTGAGGTATGCGTAA
```

[VP7 from human strain S-1-amino acid sequence]
(SEQ ID NO: 34)

```
MVCTTLYTVCAILFILFIYILLFRKMFHLITDTLIVMLILSNCVEWSQGQMFIDDIHYNG
NVETIINSTDPFNVESLCIYFPNAVVGSQGPGKSDGHLNDGNYAQTIATLFLTKGFPKGS
IIIKTYTQTSDFINSVEMTCSYNIVIIPDSPNDSESIEQIAEWILNVWRCDDMNLEIYTY
EQIGINNLWAAFGSDCDISVCPLDTTSNGIGCSPASTETYEVVSNDTQLALINVVDNVRH
RIQMNTAQCKLKNCIKGEARLNTALIRISTSSSFDNSLSPLNNGQTTRSFKINAKKWWTI
FYTIIDYINTIVQSMTPRHRAIYPEGWMLRYA
```

[VP6 from human strain S-1-nucleotide sequence including 5' and 3'
non-coding; start and stop codons of ORF underlined]
(SEQ ID No. 48)

```
GGCATTTAAAATCTCATTCACAATGGATGTACTTTTTCTATAGCGAAAACCGTGTCAGATCTTAAAGAGAAAGTTGTAG
TTGGAACAATTTATACTAATGTAGAAGATGTTGTACAACAGACGAATGAATTGATTAGAACTTTGAATGGAAATATTTTT
CATACTGGTGGCATTGGAACACAGCCTCAGAAAGAGTGGAATTTTCAGCTCCCACAATTGGGTACCACTTTATTAAATTT
AGATGATAATTATGTTCAATCAACTAGAGGCATAATTGATTTTTTATCATCTTTTATAGAAGCTGTATGTGATGATGAAA
TTGTTAGAGAAGCTTCAAGAAATGGTATGCAACCTCAATCACCAGCTCTTATATTATTATCTTCATCAAAATTTAAAACA
ATTAATTTTAATAATAGTTCTCAATCTATCAAAAATTGGAATGCTCAATCAAGACGTGAGAATCCTGTATATGAGTACAA
AAATCCAATGTTGTTTGAATATAAAAATTCTTATATTTTACAACGCGCAAATCCACAATTTGGAAGCGTCATGGGTTTAA
GATATTATACAACAAGTAATATTTGTCAAATTGCAGCATTTGATTCCACCCTAGCTGAAAATGCACCAAATAATACGCAA
CGCTTCGTTTATAATGGCAGACTAAAAAGACCCATATCAAATGTTTTAATGAAAATAGAAGCTGGTGCTCCAAATATAAG
CAACCCAACTATTTTACCTGATCCTAATAATCAAACAACTTGGCTTTTTAATCCGGTACAATTAATGAATGGAACATTTA
CCATTGAATTCTATAATAATGGTCAACTAATTGATATGGTTCGAAAATATGGAATTAGTTACTGTAAGAACTTTTGATTCT
TATAGAATAACAATTGACATGATTAGACCAGCTGCTATGACTCAATACGTTCAACGAATTTTTCCACAAGGTGGACCTTA
TCATTTTCAGGCTACATATATGTTAACATTAAGTATATTAGATGCTACCACAGAGTCCGTTCTATGTGATTCTCATTCAG
TAGAATATTCAATAGTAGCAAACGTCAGAAGAGATTCAGCAATGCCAGCTGGAACTGTTTTTCAACCGGGATTTCCATGG
GAACACACACTATCCAATTACACTGTTGCTCAAGAAGATAATTTAGAAAGATTATTGTTAATCGCATCTGTGAAGAGAAT
GGTAATGTAGATAAGCTAGAAGACTAAACATCTTCTATGCGGCCTACATACCATGTAGCATGAATCACGACTGGGTTTAG
TCCATGCTCGCATAGGGGCAAATATGCATGATATGGATGATCCCCAGAAGGATGAAATGTGAACTATGTGGCT
```

References

1. Abid, I., et al. 2007. Journal of Clinical Virology 38:78-82.
2. Banyai, K., B. et al. 2006. 37:317-22.
3. Berois, M., C. et al. 2003. 77:1757-63.
4. Castello, A. et al. 2002. 67:106-12.
5. Charpilienne, A., et al. 2002. Journal of Virology 76:7822-31.
6. Cox, M. J. et al. 1998. Tropical Medicine & International Health 3:891-5.
7. Crawford, S. E. et al. 1994. Journal of Virology 68:5945-52.
8. Gabbay, Y. B., et al. 1999. Journal of Diarrhoeal Diseases Research 17:69-74.
9. Harris, J. R., et al. 2006. Microscopy and Analysis 20:17-21.
10. Iturriza-Gomara, et al. 2004. European Journal of Epidemiology 19:589-95.
11. James, V. L., et al. 1997. UK. Journal of Medical Virology 52:86-91.
12. Jiang, B., et al. 1998 Biotechnology & Bioengineering 60:369-74.
13. Jiang, B., et al. 1995. Journal of Infectious Diseases 172:45-50.
14. Jiang, B., H. et al. 1996. Archives of Virology 141:381-90.
15. Kuzuya, M., et al. 1998. Journal of Clinical Microbiology 36:6-10.
16. Laemmli, U. K. 1970. Nature 227:680-5.
17. Mena, J. A., et al. 2006. J Biotechnol 122:443-52.
18. Mena, J. A., et al. 2007. BMC Biotechnol 7:39.
19. Milne, R. G. 1993. Solid Phase Immune Electron Microscopy of Virus Preparations, p. 25-70. In A. D. Hyatt and B.

T. Eaton (ed.), Immuno-Gold Electron Microscopy in Virus Diagnosis and Research; CRC Press, Boca Raton, Fla.
20. Nilsson, M., et al. 2000. Journal of Infectious Diseases 182:678-84.
21. Otsu, R. 1998. Comparative Immunology, Microbiology & Infectious Diseases 21:75-80.
22. Palomares, L. A., et al. 2002. Biotechnol Bioeng 78:635-44.
23. Patton, J. T., and D. Chen. 1999. Journal of Virology 73:1382-91.
24. Patton, J. T., et al. 1997. 71:9618-26.
25. Phan, T. G., et al. 2004. Journal of Medical Virology 74:173-9.
26. Rahman, M., et al. 2005. Journal of Clinical Microbiology 43:4460-5.
27. Riepenhoff-Talty, M., K. et al. 1997. Journal of Clinical Microbiology 35:486-8.
28. Sanchez-Fauquier, A., E. et al. 2003. Archives of Virology 148:399-404.
29. Schnagl, R. D., et al. 2004. Journal of Clinical Microbiology 42:2127-33.
30. Souza, D. F., et al. 1998. An outbreak of group C rotavirus gastroenteritis among adults living in Valentim Gentil, Sao Paulo State, Brazil.[erratum appears in J Diarrhoeal Dis Res 1998 September; 16(3):following x]. Journal of Diarrhoeal Diseases Research 16:59-65.
31. Steele, A. D., and V. L. James. 1999. Journal of Clinical Microbiology 37:4142-4.
32. Steyer, A., M. et al. 2006. Journal of Medical Virology 78:1250-5.
33. Terrett, L. A., and L. J. Saif. 1987. Journal of Clinical Microbiology 25:1316-9.
34. Tsunemitsu, H., B. et al. 1992. Journal of Clinical Microbiology 30:2129-34.
35. Zeng, C. Q., et al. 1998. Journal of Virology 72:201-8.
36. Zeng, C. Q., et al. 1996. Journal of Virology 70:2736-42.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims. All numerical ranges described herein include all integers and decimal values within the range and are also inclusive of the endpoints.

The invention claimed is:

1. A recombinant human rotavirus group C virus-like particle consisting of: human rotavirus group C VP6 protein and a human rotavirus group C VP7 protein.

2. The recombinant human rotavirus group C virus-like particles of claim 1 wherein the human rotavirus group C VP6 protein comprises the amino acid sequence of SEQ ID No. 32.

3. The recombinant human rotavirus group C virus-like particles of claim 1 wherein the human rotavirus group C VP7 protein comprises the amino acid sequence of SEQ ID No. 34.

4. The recombinant human rotavirus group C virus-like particles according to claim 1 admixed with a pharmaceutically acceptable carrier.

5. The recombinant human rotavirus group C virus-like particles of claim 1 attached to a solid substrate.

6. The recombinant human rotavirus group C virus-like particles of claim 1, further comprising an immunological adjuvant.

* * * * *

SEQUENCE LISTING

```
<160> NUMBER OF SEQ ID NOS: 47

<210> SEQ ID NO 1
<211> LENGTH: 884
<212> TYPE: PRT
<213> ORGANISM: Human rotavirus C
<220> FEATURE:
<221> NAME/KEY: MISC_FEATURE
<223> OTHER INFORMATION: Human rotavirus group C strain ASP88 VP2
      protein

<400> SEQUENCE: 1

Met Ile Ser Arg Asn Arg Arg Asn Asn Gln Gln Lys Asp Ile Gly
1               5                   10                  15

Lys Glu Lys Gln Leu Glu Thr Ile Ile Asp Lys Glu Val Lys Glu Asn
                20                  25                  30

Lys Asp Ser Thr Lys Glu Asp Lys Leu Val Val Thr Glu Glu Ser Asn
            35                  40                  45

Gly Asp Val Thr Ala Val Lys Glu Gln Ser Asn Asn Ile Asn Leu Gln
        50                  55                  60

Lys Asn Asp Leu Val Lys Glu Val Met Asn Ile Gln Asn Gln Thr Leu
65                  70                  75                  80

Asn Thr Val Val Ala Glu Asn Lys Val Glu Ile Glu Glu Ile Val Lys
                85                  90                  95

Lys Tyr Ile Pro Ser Tyr Asn Thr Asp Ser Leu Ile Val Lys Lys Leu
                100                 105                 110

Thr Glu Ile Gln Glu Ser Ser Ala Lys Thr Tyr Asn Thr Leu Phe Arg
            115                 120                 125

Leu Phe Thr Pro Val Lys Ser Tyr Leu Tyr Asp Ile Asn Gly Glu Lys
        130                 135                 140

Lys Leu Ser Thr Arg Trp Tyr Trp Lys Leu Leu Lys Asp Asp Leu Pro
145                 150                 155                 160

Ala Gly Asp Tyr Ser Val Arg Gln Phe Phe Leu Ser Leu Tyr Leu Asn
                165                 170                 175
```

-continued

```
Val Leu Glu Gly Met Pro Asp Tyr Ile Met Leu Arg Asp Met Ala Val
                180                 185                 190

Asp Asn Pro Tyr Ser Ala Glu Ala Gly Lys Ile Val Asp Gly Lys Ser
            195                 200                 205

Lys Glu Ile Leu Val Glu Leu Tyr Gln Asp Gln Met Thr Glu Gly Tyr
        210                 215                 220

Ile Arg Arg Tyr Met Ser Glu Leu Arg His Lys Ile Ser Gly Glu Thr
225                 230                 235                 240

Asn Thr Ala Lys Tyr Pro Ala Ile Leu His Pro Val Asp Asn Glu Leu
                245                 250                 255

Asn Gln Tyr Phe Leu Glu His Gln Leu Ile Gln Pro Leu Thr Thr Arg
            260                 265                 270

Asn Ile Ala Glu Leu Ile Pro Thr Gln Leu Tyr His Asp Pro Asn Tyr
        275                 280                 285

Val Phe Asn Ile Asp Ala Ala Phe Leu Thr Asn Ser Arg Phe Val Pro
        290                 295                 300

Pro Tyr Leu Thr Gln Asp Arg Ile Gly Leu His Asp Gly Phe Glu Ser
305                 310                 315                 320

Ile Trp Asp Ser Lys Thr His Ala Asp Tyr Val Ser Ala Arg Arg Phe
                325                 330                 335

Ile Pro Asp Leu Thr Glu Leu Val Asp Ala Glu Lys Gln Ile Lys Glu
            340                 345                 350

Met Ala Ala His Leu Gln Leu Glu Ala Ile Thr Val Gln Val Glu Ser
        355                 360                 365

Gln Phe Leu Ala Gly Ile Ser Ala Ala Ala Asn Glu Ala Phe Lys
        370                 375                 380

Phe Ile Ile Gly Ser Val Leu Ser Thr Arg Thr Ile Ala Val Glu Phe
385                 390                 395                 400

Ile Thr Ser Asn Tyr Met Ser Leu Ala Ser Cys Met Tyr Leu Met Thr
                405                 410                 415

Ile Met Pro Ser Glu Ile Phe Leu Arg Glu Ser Leu Val Ala Met Arg
            420                 425                 430

Leu Ala Ile Ile Asn Thr Leu Ile Tyr Pro Ala Leu Gly Leu Ala Gln
        435                 440                 445

Met His Tyr Gln Ala Gly Glu Val Arg Thr Pro Phe Glu Leu Ala Glu
        450                 455                 460

Met Arg Val Ala Asn Arg Ser Ile Arg Gln Trp Leu His His Cys Asn
465                 470                 475                 480

Thr Leu Gln Phe Gly Arg Gln Ile Thr Glu Gly Ile Ile His Leu Arg
                485                 490                 495

Phe Thr Asn Asp Ile Met Thr Gly Arg Ile Val Asn Leu Phe Ser Thr
            500                 505                 510

Met Leu Val Ala Leu Ser Ser Gln Pro Phe Ala Thr Tyr Pro Leu Asp
        515                 520                 525

Tyr Lys Arg Ser Val Gln Arg Ala Leu Gln Leu Leu Ser Asn Arg Thr
        530                 535                 540

Ala Gln Ile Ala Asp Leu Thr Arg Leu Ile Val Tyr Asn Tyr Thr Thr
545                 550                 555                 560

Leu Ser Ala Cys Ile Val Met Asn Met His Leu Val Gly Thr Leu Thr
                565                 570                 575

Val Glu Arg Ile Gln Ala Thr Ser Leu Thr Ser Leu Met Met Leu Ile
            580                 585                 590
```

```
Ser Asn Lys Thr Val Ile Pro Glu Pro Ser Ser Leu Phe Ser Tyr Phe
            595                 600                 605

Ser Ser Asn Ile Asn Phe Leu Thr Asn Tyr Asn Glu Gln Ile Asp Asn
        610                 615                 620

Val Val Ala Glu Ile Met Ala Ala Tyr Arg Leu Asn Leu Tyr Gln Gln
625                 630                 635                 640

Lys Met Leu Met Leu Val Thr Arg Phe Val Ser Arg Leu Tyr Ile Phe
                645                 650                 655

Asp Ala Pro Lys Ile Pro Pro Asp Gln Met Tyr Arg Leu Arg Asn Arg
            660                 665                 670

Leu Arg Asn Ile Pro Val Glu Arg Arg Arg Ala Asp Val Phe Arg Ile
        675                 680                 685

Ile Met Asn Asn Arg Asp Leu Ile Glu Lys Thr Ser Glu Arg Ile Cys
690                 695                 700

Gln Gly Val Leu Leu Ser Tyr Thr Pro Met Pro Leu Thr Tyr Val Glu
705                 710                 715                 720

Asp Val Gly Leu Thr Asn Val Ile Asn Asp Thr Asn Asn Phe Gln Ile
                725                 730                 735

Ile Asn Ile Glu Glu Ile Glu Lys Thr Gly Asp Tyr Ser Ala Ile Thr
            740                 745                 750

Asn Ala Leu Leu Arg Asp Thr Pro Ile Ile Leu Lys Gly Ala Ile Pro
        755                 760                 765

Tyr Val Thr Asn Ser Ser Val Ile Asp Val Leu Ser Lys Val Asp Thr
770                 775                 780

Thr Val Phe Ala Ser Ile Val Lys Asp Arg Asp Ile Ser Lys Leu Lys
785                 790                 795                 800

Pro Ile Lys Phe Ile Ile Asn Ser Asp Ser Ser Glu Tyr Tyr Leu Val
                805                 810                 815

His Asn Asn Lys Trp Thr Pro Thr Thr Thr Ala Val Tyr Lys Ala
            820                 825                 830

Arg Ser Gln Gln Phe Asp Ile Gln His Ser Val Ser Met Leu Glu Ser
        835                 840                 845

Asn Leu Phe Phe Val Val Tyr Asn Asp Leu Phe Lys Tyr Ile Lys Thr
850                 855                 860

Thr Thr Val Leu Pro Ile Asn Ala Val Ser Tyr Asp Gly Ala Arg Ile
865                 870                 875                 880

Met Gln Glu Thr

<210> SEQ ID NO 2
<211> LENGTH: 33
<212> TYPE: PRT
<213> ORGANISM: Artificial sequence
<220> FEATURE:
<223> OTHER INFORMATION: Antigenic epitope of human rotavirus group C
      VP2 protein

<400> SEQUENCE: 2

Leu Glu Thr Ile Ile Asp Lys Glu Val Lys Glu Asn Lys Asp Ser Thr
1               5                   10                  15

Lys Asp Glu Lys Leu Val Val Thr Glu Glu Ser Asn Gly Asp Val Thr
            20                  25                  30

Ala

<210> SEQ ID NO 3
<211> LENGTH: 33
<212> TYPE: PRT
```

```
<213> ORGANISM: Artificial Sequence
<220> FEATURE:
<223> OTHER INFORMATION: Antigenic epitope of human rotavirus group C
      VP2 protein

<400> SEQUENCE: 3

Leu Glu Thr Ile Ile Asn Lys Glu Val Lys Glu Asn Lys Asp Ser Met
1               5                   10                  15

Lys Glu Asp Lys Leu Val Val Thr Glu Glu Ser Asn Gly Asp Val Thr
            20                  25                  30

Thr

<210> SEQ ID NO 4
<211> LENGTH: 33
<212> TYPE: PRT
<213> ORGANISM: Artificial Sequence
<220> FEATURE:
<223> OTHER INFORMATION: Antigenic epitope of porcine rotavirus group C
      VP2 protein

<400> SEQUENCE: 4

Thr Glu Asn Val Glu Glu Lys Glu Ile Lys Glu Ala Lys Glu Gln Val
1               5                   10                  15

Lys Asp Glu Lys Gln Val Ile Thr Glu Glu Asn Val Asp Ser Pro Lys
            20                  25                  30

Asp

<210> SEQ ID NO 5
<211> LENGTH: 22
<212> TYPE: PRT
<213> ORGANISM: Artificial Sequence
<220> FEATURE:
<223> OTHER INFORMATION: Antigenic epitope of human rotavirus group C
      VP2 protein

<400> SEQUENCE: 5

Lys Leu Thr Glu Ile Gln Glu Ser Ser Ala Lys Thr Tyr Asn Thr Leu
1               5                   10                  15

Phe Arg Leu Phe Thr Pro
            20

<210> SEQ ID NO 6
<211> LENGTH: 18
<212> TYPE: PRT
<213> ORGANISM: Artificial Sequence
<220> FEATURE:
<223> OTHER INFORMATION: Antigenic epitope of porcine rotavirus group C
      VP2 protein

<400> SEQUENCE: 6

Asn Tyr Arg Asn Ser Arg Ile Lys Cys Gln Thr Tyr Asn Lys Leu Phe
1               5                   10                  15

Arg Leu

<210> SEQ ID NO 7
<211> LENGTH: 18
<212> TYPE: PRT
<213> ORGANISM: Artificial Sequence
<220> FEATURE:
<223> OTHER INFORMATION: Antigenic epitope of human rotavirus group C
      VP2 protein

<400> SEQUENCE: 7
```

```
Leu Asn Val Leu Glu Gly Met Pro Asp Tyr Ile Met Leu Arg Asp Met
1               5                   10                  15

Ala Val

<210> SEQ ID NO 8
<211> LENGTH: 18
<212> TYPE: PRT
<213> ORGANISM: Artificial Sequence
<220> FEATURE:
<223> OTHER INFORMATION: Antigenic epitope of human rotavirus group C
      VP2 protein

<400> SEQUENCE: 8

Leu Asn Val Leu Glu Glu Met Pro Asp Tyr Ile Met Leu Arg Asp Met
1               5                   10                  15

Ala Val

<210> SEQ ID NO 9
<211> LENGTH: 18
<212> TYPE: PRT
<213> ORGANISM: Artificial Sequence
<220> FEATURE:
<223> OTHER INFORMATION: Antigenic epitope of porcine rotavirus group C
      VP2 protein

<400> SEQUENCE: 9

Leu Asn Val Leu Asp Glu Met Pro Asp Tyr Val Met Leu Arg Asp Met
1               5                   10                  15

Ala Val

<210> SEQ ID NO 10
<211> LENGTH: 29
<212> TYPE: PRT
<213> ORGANISM: Artificial Sequence
<220> FEATURE:
<223> OTHER INFORMATION: Antigenic epitope of human rotavirus group C
      VP2 protein

<400> SEQUENCE: 10

Ala Ala His Leu Gln Leu Glu Ala Ile Thr Val Gln Val Glu Ser Gln
1               5                   10                  15

Phe Leu Ala Gly Ile Ser Ala Ala Ala Ala Asn Glu Ala
            20                  25

<210> SEQ ID NO 11
<211> LENGTH: 19
<212> TYPE: PRT
<213> ORGANISM: Artificial Sequence
<220> FEATURE:
<223> OTHER INFORMATION: Antigenic epitope of porcine rotavirus group C
      VP2 protein

<400> SEQUENCE: 11

Leu Gln Cys Lys Leu Asn His Asn Ser Trp Gln Glu Leu Val His Gly
1               5                   10                  15

Arg Asn Glu

<210> SEQ ID NO 12
<211> LENGTH: 13
<212> TYPE: PRT
<213> ORGANISM: Artificial Sequence
<220> FEATURE:
<223> OTHER INFORMATION: Antigenic epitope of human rotavirus group C
      VP2 protein
```

```
<400> SEQUENCE: 12

Leu Ser Ala Cys Ile Val Met Asn Met His Leu Val Gly
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Antigenic epitope of human rotavirus group C
      VP2 protein

<400> SEQUENCE: 13

Ile Pro Pro Asp Gln Met Tyr Arg Leu Arg Asn Arg Leu Arg Asn Ile
1               5                   10                  15

Pro

<210> SEQ ID NO 14
<211> LENGTH: 20
<212> TYPE: DNA
<213> ORGANISM: Artificial Sequence
<220> FEATURE:
<223> OTHER INFORMATION: synthetic primer

<400> SEQUENCE: 14
agccacatag ttcacatttc                                               20

<210> SEQ ID NO 15
<211> LENGTH: 19
<212> TYPE: DNA
<213> ORGANISM: Artificial Sequence
<220> FEATURE:
<223> OTHER INFORMATION: synthetic primer

<400> SEQUENCE: 15
atctcattca caatggatg                                                19

<210> SEQ ID NO 16
<211> LENGTH: 884
<212> TYPE: PRT
<213> ORGANISM: Human rotavirus C
<220> FEATURE:
<221> NAME/KEY: MISC_FEATURE
<223> OTHER INFORMATION: Human rotavirus group C Bristol strain VP2
      protein

<400> SEQUENCE: 16

Met Ile Ser Arg Asn Arg Arg Asn Asn Gln Gln Lys Asn Ile Glu
1               5                   10                  15

Lys Glu Lys Gln Leu Glu Thr Ile Ile Asn Lys Glu Val Lys Glu Asn
                20                  25                  30

Lys Asp Ser Met Lys Glu Asp Lys Leu Val Val Thr Glu Glu Ser Asn
            35                  40                  45

Gly Asp Val Thr Thr Ala Lys Glu Gln Ser Asn Asn Ile Asn Leu Gln
        50                  55                  60

Lys Asn Asp Leu Val Lys Glu Val Met Asn Ile Gln Asn Gln Thr Leu
65                  70                  75                  80

Asn Thr Val Val Thr Glu Asn Lys Val Glu Ile Glu Glu Ile Val Lys
                85                  90                  95

Lys Tyr Ile Pro Ser Tyr Asn Thr Asp Ser Leu Ile Val Lys Lys Leu
            100                 105                 110
```

-continued

Thr Glu Ile Gln Glu Ser Ser Ala Lys Thr Tyr Asn Thr Leu Phe Arg
115                 120                 125

Leu Phe Thr Pro Val Lys Ser Tyr Leu Tyr Asp Ile Asn Gly Glu Lys
130                 135                 140

Lys Leu Ser Thr Arg Trp Tyr Trp Lys Leu Leu Lys Asp Asp Leu Pro
145                 150                 155                 160

Ala Gly Asp Tyr Ser Val Arg Gln Phe Phe Leu Ser Leu Tyr Leu Asn
            165                 170                 175

Val Leu Glu Glu Met Pro Asp Tyr Ile Met Leu Arg Asp Met Ala Val
        180                 185                 190

Asp Asn Pro Tyr Ser Ala Glu Ala Gly Lys Ile Val Asp Gly Lys Ser
    195                 200                 205

Lys Glu Ile Leu Ile Glu Leu Tyr Gln Asp Gln Met Thr Glu Gly Tyr
210                 215                 220

Ile Arg Arg Tyr Met Ser Glu Leu Arg His Lys Ile Ser Gly Glu Thr
225                 230                 235                 240

Asn Thr Ala Lys Tyr Pro Ala Ile Leu His Pro Val Asp Asn Glu Leu
            245                 250                 255

Asn Gln Tyr Phe Leu Glu His Gln Leu Ile Gln Pro Leu Thr Thr Arg
        260                 265                 270

Asn Ile Ala Glu Leu Ile Pro Thr Gln Leu Tyr His Asp Pro Asn Tyr
    275                 280                 285

Val Phe Asn Ile Asp Ala Ala Phe Leu Thr Asn Ser Arg Phe Val Pro
290                 295                 300

Pro Tyr Leu Thr Gln Asp Arg Ile Gly Leu His Asp Gly Phe Glu Ser
305                 310                 315                 320

Ile Trp Asp Ser Lys Thr His Ala Asp Tyr Val Ser Ala Arg Arg Phe
            325                 330                 335

Ile Pro Asp Leu Thr Glu Leu Val Asp Ala Glu Lys Gln Ile Lys Glu
        340                 345                 350

Met Ala Ala His Leu Gln Leu Glu Ala Ile Thr Val Gln Val Glu Ser
    355                 360                 365

Gln Phe Leu Ala Gly Ile Ser Ala Ala Ala Asn Glu Ala Phe Lys
370                 375                 380

Phe Ile Ile Gly Ser Val Leu Ser Thr Arg Thr Ile Ala Val Glu Phe
385                 390                 395                 400

Ile Thr Ser Asn Tyr Met Ser Leu Ala Ser Cys Met Tyr Leu Met Thr
            405                 410                 415

Ile Met Pro Ser Glu Ile Phe Leu Arg Glu Ser Leu Val Ala Met Gln
        420                 425                 430

Leu Ala Ile Ile Asn Thr Leu Ile Tyr Pro Ala Leu Gly Leu Ala Gln
    435                 440                 445

Met His Tyr Gln Ala Gly Glu Val Arg Thr Pro Phe Glu Leu Ala Glu
450                 455                 460

Met Gln Val Ala Asn Arg Ser Ile Arg Gln Trp Leu His His Cys Asn
465                 470                 475                 480

Thr Leu Gln Phe Gly Arg Gln Ile Thr Glu Gly Ile Ile His Leu Arg
            485                 490                 495

Phe Thr Asn Asp Ile Met Thr Gly Arg Ile Val Asn Leu Phe Ser Thr
        500                 505                 510

Met Leu Val Ala Leu Ser Ser Gln Pro Phe Ala Thr Tyr Pro Leu Asp
    515                 520                 525

Tyr Lys Arg Ser Val Gln Arg Ala Leu Gln Leu Leu Ser Asn Arg Thr
            530                 535                 540

Ala Gln Ile Ala Asp Leu Thr Arg Leu Ile Val Tyr Asn Tyr Thr Thr
545                 550                 555                 560

Leu Ser Ala Cys Ile Val Met Asn Met His Leu Val Gly Thr Leu Thr
                565                 570                 575

Val Glu Arg Ile Gln Ala Thr Ser Leu Thr Ser Leu Met Met Leu Ile
            580                 585                 590

Ser Asn Lys Thr Val Ile Pro Glu Pro Ser Ser Leu Phe Ser Tyr Phe
            595                 600                 605

Ser Ser Asn Ile Asn Phe Leu Thr Asn Tyr Asn Glu Gln Ile Asp Asn
610                 615                 620

Val Val Ala Glu Ile Met Ala Ala Tyr Arg Leu Asn Leu Tyr Gln Gln
625                 630                 635                 640

Lys Met Leu Met Leu Val Thr Arg Phe Val Ser Arg Leu Tyr Ile Phe
                645                 650                 655

Asp Ala Pro Lys Ile Pro Pro Asp Gln Met Tyr Arg Leu Arg Asn Arg
            660                 665                 670

Leu Arg Asn Ile Pro Val Glu Arg Arg Arg Ala Asp Val Phe Arg Ile
            675                 680                 685

Ile Met Asn Asn Arg Asp Leu Ile Glu Lys Thr Ser Glu Arg Ile Cys
690                 695                 700

Gln Gly Val Leu Leu Ser Tyr Thr Pro Met Pro Leu Thr Tyr Val Glu
705                 710                 715                 720

Asp Val Gly Leu Thr Asn Val Ile Asn Asp Thr Asn Phe Gln Ile
                725                 730                 735

Ile Asn Ile Glu Glu Ile Glu Lys Thr Gly Asp Tyr Ser Ala Ile Thr
            740                 745                 750

Asn Ala Leu Leu Arg Asp Thr Pro Ile Ile Leu Lys Gly Ala Ile Pro
            755                 760                 765

Tyr Val Thr Asn Ser Ser Val Ile Asp Val Leu Ser Lys Val Asp Thr
770                 775                 780

Thr Val Phe Ala Ser Ile Val Lys Asp Arg Asp Ile Ser Lys Leu Lys
785                 790                 795                 800

Pro Ile Lys Phe Ile Ile Asn Ser Asp Ser Ser Glu Tyr Tyr Leu Val
                805                 810                 815

His Asn Asn Lys Trp Thr Pro Thr Thr Thr Ala Val Tyr Lys Ala
            820                 825                 830

Arg Ser Gln Gln Phe Asp Ile Gln His Ser Val Ser Met Leu Glu Ser
            835                 840                 845

Asn Leu Phe Phe Val Val Tyr Asn Asp Leu Phe Lys Tyr Ile Lys Thr
850                 855                 860

Thr Thr Val Leu Pro Ile Asn Ala Val Ser Tyr Asp Gly Ala Arg Ile
865                 870                 875                 880

Met Gln Glu Thr

<210> SEQ ID NO 17
<211> LENGTH: 884
<212> TYPE: PRT
<213> ORGANISM: Porcine rotavirus
<220> FEATURE:
<221> NAME/KEY: MISC_FEATURE
<223> OTHER INFORMATION: porcine rotavirus group C Cowden strain VP2
    protein

<400> SEQUENCE: 17

-continued

```
Met Ile Ser Arg Asn Arg Arg Asn Thr Gln Gln Lys Asp Ala Glu
1               5                   10                  15

Lys Glu Lys Gln Thr Glu Asn Val Glu Lys Glu Ile Lys Glu Ala
            20                  25                  30

Lys Glu Gln Val Lys Asp Glu Lys Gln Val Ile Thr Glu Glu Asn Val
        35                  40                  45

Asp Ser Pro Lys Asp Val Lys Glu Gln Ser Asn Thr Val Asn Leu Gln
    50                  55                  60

Lys Asn Asp Leu Val Lys Glu Val Ile Asn Ile Gln Asn Gln Thr Leu
65                  70                  75                  80

Asn Thr Ile Val Ala Glu Asn Lys Val Glu Ile Glu Glu Val Val Lys
                85                  90                  95

Lys Tyr Ile Pro Ser Tyr Ser Thr Asp Lys Leu Ile Val Lys Lys Leu
                100                 105             110

Thr Glu Ile Gln Glu Ser Ser Ala Lys Thr Tyr Asn Lys Leu Phe Arg
            115                 120                 125

Leu Phe Thr Pro Val Lys Ser Tyr Leu Tyr Asp Val Asn Gly Glu Lys
        130                 135                 140

Lys Leu Ser Thr Arg Trp Tyr Trp Lys Leu Leu Lys Asp Asp Leu Pro
145                 150                 155                 160

Ala Gly Asp Tyr Ser Val Arg Gln Phe Phe Leu Ser Leu Tyr Leu Asn
                165                 170                 175

Val Leu Asp Glu Met Pro Asp Tyr Val Met Leu Arg Asp Met Ala Val
                180                 185                 190

Asp Asn Pro Tyr Ser Ala Glu Ala Gly Lys Ile Val Asp Glu Lys Ser
            195                 200                 205

Lys Glu Ile Leu Val Glu Ile Tyr Gln Asp Gln Met Thr Glu Gly Tyr
210                 215                 220

Ile Arg Arg Tyr Met Ser Asp Leu Arg His Arg Ile Ser Gly Glu Thr
225                 230                 235                 240

Asn Thr Ala Lys Tyr Pro Ala Ile Leu His Pro Val Asp Glu Glu Leu
                245                 250                 255

Asn Lys Tyr Phe Leu Glu His Gln Leu Ile Gln Pro Leu Thr Thr Arg
                260                 265                 270

Asn Ile Ala Glu Leu Ile Pro Thr Gln Leu Tyr His Asp Pro Asn Tyr
            275                 280                 285

Val Phe Asn Ile Asp Ala Ala Phe Leu Thr Asn Ser Arg Phe Val Pro
        290                 295                 300

Pro Tyr Leu Thr Gln Asp Arg Ile Gly Leu His Asp Gly Phe Glu Ser
305                 310                 315                 320

Ile Trp Asp Ala Lys Thr His Ala Asp Tyr Val Ser Ala Arg Arg Phe
                325                 330                 335

Val Pro Asp Leu Thr Glu Leu Val Asp Ala Glu Lys Gln Met Lys Glu
            340                 345                 350

Met Ala Ala His Leu Gln Leu Glu Ala Ile Thr Val Gln Val Glu Ser
                355                 360                 365

Gln Phe Leu Ala Gly Ile Ser Ala Ala Ala Asn Glu Ala Phe Lys
        370                 375                 380

Phe Ile Ile Gly Thr Val Leu Ser Thr Arg Thr Ile Ala Val Glu Phe
385                 390                 395                 400

Ile Thr Ser Asn Tyr Met Ser Leu Ala Ser Cys Met Tyr Leu Met Thr
                405                 410                 415
```

```
Ile Met Pro Ser Glu Ile Phe Leu Arg Glu Ser Leu Val Ala Met Gln
            420                 425                 430

Leu Ala Val Ile Asn Thr Leu Thr Tyr Pro Ala Leu Gly Leu Ala Gln
        435                 440                 445

Met His Tyr Gln Ala Gly Glu Ile Arg Thr Pro Phe Glu Leu Ala Glu
    450                 455                 460

Met Gln Val Ala Asn Arg Pro Ile Arg Gln Trp Leu His His Cys Asn
465                 470                 475                 480

Thr Leu Gln Phe Gly Arg Gln Val Thr Glu Gly Val Thr His Leu Arg
                485                 490                 495

Phe Thr Asn Asp Ile Met Thr Gly Arg Ile Val Asn Leu Phe Ser Thr
            500                 505                 510

Met Leu Val Ala Leu Ser Ser Gln Pro Phe Ala Thr Tyr Pro Leu Asp
        515                 520                 525

Tyr Lys Arg Ser Val Gln Arg Ala Leu Gln Leu Leu Ser Asn Arg Thr
    530                 535                 540

Ala Gln Ile Ala Asp Leu Thr Arg Leu Ile Val Tyr Asn Tyr Thr Thr
545                 550                 555                 560

Leu Ser Ala Cys Ile Val Met Asn Met His Leu Val Gly Thr Leu Thr
                565                 570                 575

Val Glu Arg Ile Gln Ala Thr Ala Leu Thr Ser Leu Ile Met Leu Ile
            580                 585                 590

Ser Asn Lys Thr Val Ile Pro Glu Pro Ser Ser Leu Phe Ser Tyr Phe
        595                 600                 605

Ser Ser Asn Ile Asn Phe Leu Thr Asn Tyr Asn Glu Gln Ile Asp Asn
    610                 615                 620

Val Val Ala Glu Ile Met Ala Ala Tyr Arg Leu Asp Leu Tyr Gln Gln
625                 630                 635                 640

Lys Met Leu Met Leu Val Thr Arg Phe Val Ser Arg Leu Tyr Ile Phe
                645                 650                 655

Asp Ala Pro Lys Ile Pro Pro Asp Gln Met Tyr Arg Leu Arg Asn Arg
            660                 665                 670

Leu Arg Asn Ile Pro Val Glu Arg Arg Arg Ala Asp Val Phe Arg Ile
        675                 680                 685

Ile Met Asn Asn Arg Asp Leu Ile Glu Lys Thr Ser Glu Arg Ile Cys
    690                 695                 700

Gln Gly Val Leu Leu Ser Tyr Ser Pro Met Pro Leu Thr Tyr Val Glu
705                 710                 715                 720

Asp Val Gly Leu Thr Asn Val Asn Asp Thr Asn Gly Phe Gln Ile
                725                 730                 735

Ile Asn Ile Glu Glu Ile Glu Lys Thr Gly Asp Tyr Ser Ala Ile Thr
            740                 745                 750

Asn Ala Leu Leu Arg Asp Thr Pro Ile Ile Leu Lys Gly Ala Ile Pro
        755                 760                 765

Tyr Val Thr Asn Ser Ser Val Ile Asp Val Leu Ser Lys Ile Asp Thr
    770                 775                 780

Thr Val Phe Ala Ser Ile Val Lys Asp Arg Asp Ile Ser Lys Leu Lys
785                 790                 795                 800

Pro Ile Lys Phe Thr Ile Asn Ser Asp Ser Ser Glu Tyr Tyr Leu Val
                805                 810                 815

His Asn Asn Lys Trp Thr Pro Thr Thr Thr Ala Val Tyr Lys Ala
            820                 825                 830
```

Arg Ser Gln Gln Phe Asn Ile Gln His Ser Val Ser Met Leu Glu Ser
835                 840                 845

Asn Leu Phe Phe Val Val Tyr Asn Asp Leu Phe Lys Tyr Ile Lys Thr
850                 855                 860

Thr Thr Val Leu Pro Ile Asn Ala Val Ser Tyr Asp Gly Ala Arg Ile
865                 870                 875                 880

Met Gln Glu Thr

<210> SEQ ID NO 18
<211> LENGTH: 2720
<212> TYPE: DNA
<213> ORGANISM: Human rotavirus C
<220> FEATURE:
<221> NAME/KEY: misc_feature
<223> OTHER INFORMATION: Human rotavirus group C strain ASP88 VP2
      nucleotide sequence

<400> SEQUENCE: 18

```
tcgaggacaa atcgtccaag atgataagca gaaacaggcg cagaaataac caacaaaaag      60
atataggaaa agagaaacaa ttagagacta taattgacaa agaagtaaag gaaaacaaag     120
attctacaaa agaagataag ctagtagtta cggaagaaag taatggtgac gtcacagctg     180
ttaaagaaca atcgaataat attaatttac aaaagaatga tttggttaaa gaagtcatga     240
atatacagaa tcaaacatta atacagtag ttgctgagaa taaagttgaa atagaagaaa     300
tagttaaaaa atacattccc tcatataata ctgacagcct tattgttaaa aagttaactg     360
aaatccagga atcaagtgct aaaacatata atacattatt cagattattt actccagtta     420
aaagttattt atatgacata aatggtgaga aaaaattatc gactagatgg tattggaaat     480
tgctcaaaga tgatttacct gctggtgatt actcagttag acaattcttc ctgtcactat     540
atttaaatgt tttagaggga atgcccgatt acataatgct tcgtgatatg gcagtggata     600
acccatattc agcagaagca ggtaaaaatcg tagatggaaa gtctaaagaa attttagttg     660
aactatatca agaccaaatg acagaagggt atattagaag atatatgtct gaattaagac     720
ataaaatatc tggagaaaca aatactgcaa aatatccagc tattctacat cccgtggata     780
atgagcttaa tcaatacttt cttgagcatc agttaattca accattaact acaagaaata     840
ttgcagaatt gattccaact caattatatc atgatccaaa ttacgttttt aatattgatg     900
cagccttttt aacaaattca agatttgttc caccatactt aacacaggat aggattggat     960
tacatgatgg attcgaatca atatgggatt caaaacccca tgctgattac gtttcagcta    1020
gaagatttat acctgattta actgaactgg tagatgctga aaagcaaata aaagaaatgg    1080
ctgcacattt acaactagag gctattacag tacaggttga atcacaattt ttagcgggaa    1140
ttagtgctgc tgcagctaat gaagcgttca aatttataat tggctcagtt ttatctacca    1200
gaacaatagc tgtagaattc ataaccctcaa actatatgtc gttagcatca tgtatgtatt    1260
taatgactat tatgccatca gagattttct tgagagaatc attagttgct atgcgattag    1320
caataataaa taccctttatt tatccagctc taggtttagc gcaaatgcat tatcaagcag    1380
gtgaagtgag gacccccattc gaattagctg agatgcgagt agctaataga tctattagac    1440
aatggttaca tcattgtaat acacttcaat ttggtagaca gataacggaa gggataattc    1500
atctacgatt tactaatgat atcatgacag gtaggatagt gaacttatttt caacaatgc    1560
tagtagcttt atcatctcag ccattcgcta catatccttt agactataaa agatctgtac    1620
aaagagcatt acaacttttta tcaaatagaa cagcccaaat agcagattta accagattaa    1680
```

```
tagtatacaa ttatactaca ttatctgcat gtatagtcat gaatatgcat ttagtaggaa      1740
ctcttactgt tgaacgtata caggccactt ctctaacttc tttaatgatg ttaatttcta      1800
ataagacagt tattccagaa ccatcgtctc tttttttcata tttctctagt aacattaatt     1860
ttcttacaaa ttataatgag caaattgata atgtggtagc agaaataatg gccgcatata      1920
gattgaattt atatcaacag aaaatgttga tgctcgttac caggtttgtg tcaaggttgt      1980
acatatttga tgctcctaaa ataccgccag atcagatgta tagattaaga aaccgattaa      2040
gaaatattcc agttgaaaga agaagagctg atgtgttcag aattattatg aataatagag      2100
atttaatcga aaaacatca gaacgtatat gtcagggtgt gttgttatct tatacaccaa       2160
tgcctttaac ttacgttgaa gatgtcgggt taacaaatgt aattaatgac actaataact      2220
tccaaataat taatatagaa gaaattgaga agaccggtga ctattcagcc ataacgaatg      2280
cattacttcg ggatactcca attatattga aggtgcgat tccatatgtt actaactcat       2340
cagtaattga tgttttatct aaagtggaca ccacagtgtt cgcaagcatc gtaaaagata      2400
gggatatttc aaagttaaaa ccaataaaat tcataattaa ttcagattca tccgaatatt      2460
atttagtaca caataataaa tggacaccaa caacaactac agcagtatat aaagctagat      2520
ctcagcaatt tgatatacaa cattcagtat caatgctaga gtcaaactta ttttttgtgg      2580
tatataatga tttatttaaa tacattaaaa ccactacagt tctgccgata aatgctgtct      2640
cttatgatgg tgcaagaatt atgcaagaaa cataaatgat tgtatagtat catcttgtaa      2700
cgacctcaaa ctctgtggct                                                  2720
```

<210> SEQ ID NO 19
<211> LENGTH: 2736
<212> TYPE: DNA
<213> ORGANISM: Human rotavirus C
<220> FEATURE:
<221> NAME/KEY: misc_feature
<223> OTHER INFORMATION: Human rotavirus group C Bristol strain VP2
      nucleotide sequence

<400> SEQUENCE: 19

```
ggcttaaaaa gatcagttga ggacaaatcg ttcaagatga taagcagaaa caggcgcaga       60
aataatcaac aaaaaaacat agaaaaagag aaacaattag agactataat taacaaagaa      120
gttaaggaaa acaagagttc tatgaaagaa gataagctag tagttacaga agaaagcaat      180
ggagacgtca caactgctaa agaacaatcg aataatatta atttacaaaa gaatgatttg      240
gttaaagaag tcatgaatat acagaatcaa acattaaata cagtagttac tgagaataaa      300
gttgaaatag aagaaatagt taaaaaatac attccatcat ataatactga tagcctcatt      360
gttaaaaagt taactgaaat ccaggaatca agtgctaaaa catataatac attgtttaga      420
ttatttactc cagttaaaag ttatttatat gatataaatg gtgagaaaaa attatcgact      480
agatggtatt ggaaattgct caaagatgat ttacctgctg gtgattactc agttagacaa      540
ttcttcctgt cactatattt aaatgtttta gaggaaatgc cgattacat aatgcttcgt       600 gatatggcag tggataaccc atattcagca gaagcaggta aaatcgtaga tggaaagtct      660
aaagaaattt tgattgaact atatcaagac cagatgacag aaggatatat tagaagatat      720
atgtctgaat taagacataa aatatctgga gagacaaata ctgcaaaata cccagctatt      780
ctacatcccg tggataatga acttaatcaa tactttcttg agcatcagtt aattcaacca      840
ttaactacaa ggaacattgc agaattgatt ccaactcaat tatatcatga tccaaattac      900 gttttttaata ttgatgcagc cttttttaaca aattcaagat ttgttccacc atacttaaca    960
```

```
caggatagga ttggattaca tgatggattt gaatcaatat gggattcaaa aactcatgct    1020
gattacgttt cagctagaag atttatacct gatttaactg aactggtgga tgctgaaaag    1080
caaataaaag aaatggctgc acatttacaa ctagaggcta ttacggtaca ggttgaatca    1140 caattttag caggaattag tgctgctgca gctaatgaag cgtttaaatt tataattggc    1200
tcagttttat ctaccagaac aatagctgta gaattcataa cctcaaacta tatgtcacta    1260
gcatcatgta tgtatttaat gactattatg ccatcagaga ttttcttaag agaatcatta    1320
gttgctatgc aattagcaat aataaatacc cttatttatc cagctctagg tttagcgcaa    1380
atgcattatc aagcaggtga agtgaggact ccattcgaat tagctgaaat gcaagtagct    1440
aatagatcta ttagacaatg gttacatcat tgtaatacac ttcaatttgg tagacagata    1500
acggaaggga taattcatct acgatttact aatgatatca tgacaggcag atagtgaac    1560 ttattttcaa caatgttagt ggctctatca tctcagcctt tcgctacata tcctttagac    1620
tataaaagat ctgtacaaag agcgttacaa cttttatcaa atagaacagc tcaaatagca    1680
gatttaacca gattaatagt atacaattat actacattat ctgcttgtat agttatgaat    1740
atgcatttag taggaactct tactgttgaa cgtatacaag ccacttctct aacttcttta    1800
atgatgttaa tctctaataa gacagttatt ccggaaccat cgtctctttt ttcatatttc    1860
tctagtaaca ttaattttct tacaaattat aatgagcaaa ttgataatgt ggtagcagaa    1920
ataatggccg catatagatt gaatttatat caacagaaaa tgttgatgct cgttaccaga    1980
tttgtgtcaa agttatacat atttgatgct cctaagatac caccagatca gatgtataga    2040
ttaagaaacc gattaagaaa tattccagtt gaaagaagaa gagctgacgt attcagaatt    2100
attatgaata atagagattt aatcgaaaaa acatcagaac gtatatgcca gggtgtgctg    2160
ttatcttata caccaatgcc tttaacttac gttgaagatg tcgggttaac aaatgtaatt    2220
aatgacacta atagctttca ataattaat attgaagaaa ttgagaagac cggtgactat    2280
tcagctataa cgaatgcatt acttcgggat actccaatca tattgaaagg tgcgattcca    2340
tatgttacta actcatcagt aattgatgtt ttatctaaag tggacaccac agtgttcgca    2400
agcattgtaa aagataggga catttcaaag ttaaaaccaa taaaattcat aattaattca    2460
gattcatccg aatattattt agtacataat aataaatgga caccaacaac aactacagca    2520
gtatataaag ctagatctca gcaatttgat atacaacatt cagtatcaat gctagagtca    2580
aacttatttt ttgtggtata taatgattta tttaaataca ttaaaaccac tacagttctg    2640
ccgataaatg ctgtctctta tgacggtgca agaattatgc aagaaacata aatgattgta    2700
tagtatcatc ttgtgacgac ctcaaacttt gtggct    2736
```

<210> SEQ ID NO 20
<211> LENGTH: 18
<212> TYPE: DNA
<213> ORGANISM: Artificial Sequence
<220> FEATURE:
<223> OTHER INFORMATION: synthetic primer

<400> SEQUENCE: 20

```
agccacatga tcttgttt                                                       18
```

<210> SEQ ID NO 21
<211> LENGTH: 18
<212> TYPE: DNA
<213> ORGANISM: Artificial Sequence
<220> FEATURE:

```
<223> OTHER INFORMATION: synthetic primer

<400> SEQUENCE: 21
ggcatttaaa aaagaaga                                                 18

<210> SEQ ID NO 22
<211> LENGTH: 20
<212> TYPE: DNA
<213> ORGANISM: Artificial Sequence
<220> FEATURE:
<223> OTHER INFORMATION: synthetic primer

<400> SEQUENCE: 22
tcgaggacaa atcgtccaag                                               20

<210> SEQ ID NO 23
<211> LENGTH: 19
<212> TYPE: DNA
<213> ORGANISM: Artificial Sequence
<220> FEATURE:
<223> OTHER INFORMATION: synthetic primer

<400> SEQUENCE: 23
agccacagag tttgaggtc                                                19

<210> SEQ ID NO 24
<211> LENGTH: 395
<212> TYPE: PRT
<213> ORGANISM: Human rotavirus C
<220> FEATURE:
<221> NAME/KEY: MISC_FEATURE
<223> OTHER INFORMATION: Human rotavirus group C VP6 consensus sequence

<400> SEQUENCE: 24
```

Met Asp Val Leu Phe Ser Ile Ala Lys Thr Val Ser Asp Leu Lys Lys
1               5                   10                  15

Lys Val Val Val Gly Thr Ile Tyr Thr Asn Val Glu Asp Val Val Gln
                20                  25                  30

Gln Thr Asn Glu Leu Ile Arg Thr Leu Asn Gly Asn Ile Phe His Thr
            35                  40                  45

Gly Gly Ile Gly Thr Gln Pro Gln Lys Glu Trp Asn Phe Gln Leu Pro
        50                  55                  60

Gln Leu Gly Thr Thr Leu Leu Asn Leu Asp Asp Asn Tyr Val Gln Ser
65                  70                  75                  80

Thr Arg Gly Ile Ile Asp Phe Leu Ser Ser Phe Ile Glu Ala Val Cys
                85                  90                  95

Asp Asp Glu Ile Val Arg Glu Ala Ser Arg Asn Gly Met Gln Pro Gln
            100                 105                 110

Ser Pro Ala Leu Ile Leu Leu Ser Ser Lys Phe Lys Thr Ile Asn
        115                 120                 125

Phe Asn Asn Ser Ser Gln Ser Ile Lys Asn Trp Asn Ala Gln Ser Arg
        130                 135                 140

Arg Glu Asn Pro Val Tyr Glu Tyr Lys Asn Pro Met Leu Phe Glu Tyr
145                 150                 155                 160

Lys Asn Ser Tyr Ile Leu Gln Arg Ala Asn Pro Gln Phe Gly Ser Val
                165                 170                 175

Met Gly Leu Arg Tyr Tyr Thr Thr Ser Asn Thr Cys Gln Ile Ala Ala
            180                 185                 190

Phe Asp Ser Thr Leu Ala Glu Asn Ala Pro Asn Asn Thr Gln Arg Phe
        195                 200                 205

Val Tyr Asn Gly Arg Leu Lys Arg Pro Ile Ser Asn Val Leu Met Lys
    210                 215                 220
Ile Glu Ala Gly Ala Pro Asn Ile Ser Asn Pro Thr Ile Leu Pro Asp
225                 230                 235                 240
Pro Asn Asn Gln Thr Thr Trp Leu Phe Asn Pro Val Gln Leu Met Asn
                245                 250                 255
Gly Thr Phe Thr Ile Glu Phe Tyr Asn Asn Gly Gln Leu Ile Asp Met
            260                 265                 270
Val Arg Asn Met Gly Ile Val Thr Val Arg Thr Phe Asp Ser Tyr Arg
        275                 280                 285
Ile Thr Ile Asp Met Ile Arg Pro Ala Ala Met Thr Gln Tyr Val Gln
    290                 295                 300
Arg Ile Phe Pro Gln Gly Gly Pro Tyr His Phe Gln Ala Thr Tyr Met
305                 310                 315                 320
Leu Thr Leu Ser Ile Leu Asp Ala Thr Thr Glu Ser Val Leu Cys Asp
                325                 330                 335
Ser His Ser Val Glu Tyr Ser Ile Val Ala Asn Val Arg Arg Asp Ser
            340                 345                 350
Ala Met Pro Ala Gly Thr Val Phe Gln Pro Gly Phe Pro Trp Glu His
        355                 360                 365
Thr Leu Ser Asn Tyr Thr Val Ala Gln Glu Asp Asn Leu Glu Arg Leu
    370                 375                 380
Leu Leu Ile Ala Ser Val Lys Arg Met Val Met
385                 390                 395

<210> SEQ ID NO 25
<211> LENGTH: 1185
<212> TYPE: DNA
<213> ORGANISM: Human rotavirus C
<220> FEATURE:
<221> NAME/KEY: misc_feature
<223> OTHER INFORMATION: Human rotavirus group C VP6 Bristol nucleotide
      sequence

<400> SEQUENCE: 25
atggatgtac tttttttctat agcgaaaact gtgtcagatc ttaaaaagaa agttgtggtt      60
ggaacaattt atactaatgt agaagatgtt gtacaacaga cgaatgaatt gattagaact     120
ttaaatggaa atattttttca tactggtggc attggaacac agcctcagaa agagtggaat     180
tttcagctgc cacaattggg tacaacttta ttaaatttag atgataatta tgttcaatca     240
actagaggca taatcgattt tttatcatct tttatagaag ctgtatgtga tgatgaaatt     300
gttagagaag cttcaagaaa tggtatgcaa cctcaatcac cagctcttat attattatct     360
tcatcaaaat ttaaaacaat taattttaat aatagttctc aatctattaa aaattggaat     420
gctcaatcaa gacgtgagaa tcctgtatat gagtatataaaa atccaatgtt gtttgaatat     480 aaaaaattcgt atattttaca cgcgcaaat ccacaatttg gaagcgtcat gggtttaaga     540
tattatacaa caagtaatac ttgtcaaatt gcagcatttg attccaccct agctgaaaat     600
gcaccaaaca atacacaacg cttcgtttat aatggcagac taaaaagacc catatcaaac     660
gttttaatga aaatagaagc tggtgctcca aatataagca acccaactat tttacctgat     720
cctaataatc aaacaacttg gctttttaat ccggtacaat aatgaatgg aacatttacc     780 attgaattct ataataatgg tcaactaatt gatatggttc gaaatatggg aatagttact     840
gtaagaactt ttgattctta tagaataaca attgacatga ttagaccagc tgctatgact     900

```
caatacgttc aacgaatttt ccacaaggt ggaccttatc attttcaggc tacatatatg    960
ttaacattaa gtatattaga tgctaccaca gagtccgttc tatgtgattc tcattcagtg   1020
gaatattcaa tagtagcaaa cgttagaaga gattcagcga tgccagctgg aactgttttt   1080
caaccgggat tccatggga acacacacta tccaattaca ctgttgctca agaagataat    1140
ttagaaagat tattgttaat tgcatctgtg aagagaatgg taatg                   1185
```

<210> SEQ ID NO 26
<211> LENGTH: 1185
<212> TYPE: DNA
<213> ORGANISM: Human rotavirus C
<220> FEATURE:
<221> NAME/KEY: misc_feature
<223> OTHER INFORMATION: Human rotavirus group C VP6 Jajeri nucleotide
      sequence

<400> SEQUENCE: 26

```
atggatgtac ttttttctat agcgaaaact gtgtcagatc ttaaaaagaa agttgtagtt     60
ggaacaattt atactaatgt agaagatgtt gtacaacaga cgaatgaatt gattagaact    120
ttgaatggaa atattttta tactggtggt attggaacac agcctcagaa agagtggaat     180
tttcagctac cacaatttggg tacaacttta ttaaatttag atgacaatta tgttcaatca    240
accagaggca taattgattt tttatcatct tttatagaag ctgtatgtga tgatgaaatt    300
gttagagaag cttcaagaaa tggtatgcaa cctcaatcac cagctcttat attattatct    360
tcatcaaaat ttaaaacaat taattttaat aatagttctc aatctatcaa aaattggaat    420
gctcaatcaa gacgtgagaa tcctgtatat gagtacaaaa atccaatggt gtttgaatat    480
aaaaattctt atattttaca acgcgcaaat ccacaatttg gaagcgtcat gggtttaaga    540
tattatacaa caagtaatac ttgtcaaatt gcagcatttg attccaccct agctgaaaat    600
gcaccaaaca atacgcaacg cttcgtttat aatggcagac taaaaagacc catatcaaat    660 gtttttaatga aaatagaagc tggtgcccca aatataagca acccaactat tttacctgat    720
cctaataatc aaacaacttg gcttttaat ccagtacagt taatgaatgg aacattcact     780
attgaattct ataataatgg tcaactaatt gatatggttc gaaatatggg aatagttacc    840
gtaagaactt tgattctta gaataaca attgacataa ttagaccagc tgctatgact       900
caatacgttc aacgaatttt ccacaaggt ggaccttatc attttcaggc tacatatatg    960
ttaacattaa gtatattaga tgctactaca gagtccgttc tatgtgattc tcattcagta   1020
gaatattcaa tagtagcaaa cgtcagaaga gattcagcga tgccagctgg aactgttttt   1080
caaccaggat tccatggga acacacacta tccaattaca ctgttgctca agaagataat    1140
ttagaaagat tattgttaat cgcatctgtg aagagaatgg taatg                   1185
```

<210> SEQ ID NO 27
<211> LENGTH: 1185
<212> TYPE: DNA
<213> ORGANISM: Human rotavirus C
<220> FEATURE:
<221> NAME/KEY: misc_feature
<223> OTHER INFORMATION: Human rotavirus group C VP6 CMH004 nucleotide
      sequence

<400> SEQUENCE: 27

```
atggatgtac ttttttctat agcgaaaact gtatcagatc ttaaaaagaa agttgtagtt     60
ggaacaattt atactaatgt agaagatgtt gtacaacaga cgaatgaatt gattagaact    120
ttgaatggaa atatttttca tactggtggc attggaacac agcctcataa agagtggaat    180
```

```
tttcagctac cacaattagg tacaacttta ttaaatttag atgataatta tgttcaatca      240
actagaggca taattgattt tttatcatct tttatagaag ctgtatgtga tgatgaaatt      300
gttagagaag cttcaagaaa tggtatgcaa cctcaatcac cagctcttat attattatct     360
tcatcaaaat ttaaaacaat taattttaat aatagttctc aatctatcaa aaattggaat     420
gctcaatcaa gacgtgagaa tcctgtatat gagtacaaaa atccaatgtt gtttgaatat     480
aaaaattctt atattttaca acgcgcaaat ccacaatttg aagtgttat gggtttaaga      540 tattacacaa caagtaatac ttgtcaaatt gcagcatttg attccaccct agctgaaaat     600
gcaccgaaca atacgcaacg cttcgtttat aatggcagac taaaaagacc catatcaaat     660
gttttaatga aaatagaagc tggtgctcca aatataagca acccaactat tttacctgat     720
cctaataatc aaacaacttg gcttttaat ccggtacaat taatgaatgg aacatttacc     780
attgaattct ataataatgg tcaactaatt gatatggttc gaaatatggg aatagttact     840
gtaagaactt ttgattctta tagaataaca attgacatga ttagaccagc tgctatgacc     900
caatacgttc aacgaatttt tccacaaggt ggaccttatc attttcaggc tacatatatg     960
ttaacattaa gtatattaga tgctaccaca gaatccgttc tatgtgattc tcattcagta    1020
gaatattcaa tagtagcaaa cgtcagaaga gattcagcga tgccagctgg aactgttttt     1080
caaccgggat ttcatggga acacacacta tccaattaca ctgttgctca agaagataat     1140
ttagagagat tattgttaat cgcatctgtg aagagaatgg taatg                     1185

<210> SEQ ID NO 28
<211> LENGTH: 1185
<212> TYPE: DNA
<213> ORGANISM: Human rotavirus C
<220> FEATURE:
<221> NAME/KEY: misc_feature
<223> OTHER INFORMATION: Human rotavirus group C VP6 V508 nucleotide
      sequence

<400> SEQUENCE: 28
atggatgtac ttttttctat agcgaaaact gtgtcagatc ttaaaaagaa agttgtagtt       60
ggaacaattt ataccaatgt agaagatgtt gtacaacaga cgaatgaatt gattagaact      120
ttgaatggaa atgttttca tactggtggc attggaacac agcctcagaa agagtggaat       180
tttcaactac cacaattggg tacaacttta ttaaatttag atgataatta tgttcaatca     240
actagaggca taattgattt tttatcatct tttatagaag ctgtatgtga tgatgaaatt      300
gttagagaag cttcaagaaa tggtatgcaa ccccaatcac cagctcttat attattatct     360
tcatcaaaat ttaaaacaat taatttgaat aatagttctc aatctatcaa aaattggaat     420
gctcaatcaa gacgtgagaa tcctgtatat gagtacaaaa atccaatgtt gtttgaatat     480
aaaaattctt atattttaca acgcgcaaat ccacaatttg aagcgtcat gggtttaaga      540 tattatacaa caagtaatac ttgtcaaatt gcagcatttg attccaccct agctgaaaat     600
gcaccaaaca atacgcaacg cttcgtttat aatggcagac taaaaagacc catatcaaat     660
gttttaatga aaatagaagc tggtgctcca aatataagca acccaactat tttacctgat     720
cctaataatc aaacaacttg gcttttaat ccagtacaat tgatgaatgg aacattcacc     780
attgagttct ataataatgg tcaactaatt gatatggttc gaaatatggg aatagttact     840
gtaagaactt ttgattctta tagaataaca attgacatga ttagaccagc tgctatgact     900
caatacgttc aacgaatttt tccacaaggc ggaccttatc attttcaggc tacatatatg     960
```

-continued

```
ttaacgttaa gtatattaga tgctaccaca gagtccgttt tatgtgattc tcattcagta    1020
gaatattcaa tagtagccaa cgtcagaaga gattcagcga tgccagctgg aaccgttttt    1080
caaccgggat ttccatggga acacacacta tccaattaca ctgttgctca agaagataat    1140
ttagaaagat tattgttaat cgcatctgtg aagagaatgg taatg                    1185
```

<210> SEQ ID NO 29
<211> LENGTH: 1185
<212> TYPE: DNA
<213> ORGANISM: Human rotavirus C
<220> FEATURE:
<221> NAME/KEY: misc_feature
<223> OTHER INFORMATION: Human rotavirus group C VP6 China nucleotide
    sequence

<400> SEQUENCE: 29

```
atggatgtac tttttttctat agcgaaaact gtgtcagatc ttaaaaagaa agttgtagtt      60
ggaacaattt atactaatgt agaagatgtt gtacaacaga cgaatgaact gattagaact     120
ttgaatggaa atatttttca tactggtggt attggaacac agccccagaa agagtggaat     180
tttcagctac cacaattggg tacaacttta ttaaatttag atgataatta tgttcaatca     240
actagaggca taattgattt tttatcatct tttatagaag ctgtatgtga tgatgaaatt     300
gttagagaag cttcaagaaa tggtatgcaa cctcaatcac cagctcttat attattatct     360
tcatcaaaat ttaagacaat taattttaat aatagttctc aatctatcaa aaattggaat     420
gctcaatcaa gacgtgagaa tcctgtatat gaatacaaaa atccaatgtt gttggaatat     480 aaaaaattctt atattttaca acgcgcaatt ccacaatttg gaagcgtcat gggttttaaga    540 tattatacaa caagtaatac ttgtcaaatt gcagcatttg attccaccct agctgaaaat     600
gcaccaaaca tacgcaacg cttcgtttat aatggcagac taaaaagacc catatcaaat     660
gttttaatga aaatagaagc tggtgctcca aatataagca acccaactat tttacctgat     720
cctaataatc aaacaacttg gctttttaat ccggtacaat taatgaatgg aacattcacc     780
attgaattct ataataatgg tcaactaatt gatatggttc gaaatatggg aatagttact     840
gtaaggactt tgattcttta gaataaca attgacatga ttagaccagc tgctaggact      900
caatacgttc aacaaattt tccacaaggt ggaccttatc atttcaggc tacatatatg      960 ttaacattaa gtatattaga tgctaccaca gagtccgttc tatgtgattc tcattcagta    1020
gaatattcaa tagtagcaaa cgtcagaaga gattcagcga tgccagctgg aactgttttt    1080
caaccgggtt ttccatggga acacacacta tccaattaca ctgttgctca agaagataat    1140
ttagaaagat tattgttaat cgcatctgtg aagagaatgg taatg                    1185
```

<210> SEQ ID NO 30
<211> LENGTH: 1185
<212> TYPE: DNA
<213> ORGANISM: Human rotavirus C
<220> FEATURE:
<221> NAME/KEY: misc_feature
<223> OTHER INFORMATION: Human rotavirus group C VP6 BCN6 nucleotide
    sequence

<400> SEQUENCE: 30

```
atggatgtac tttttttctat agcgaaaact gtgtcagatc ttaaaaagaa agttgtagtt      60
ggaacaattt atactaatgt agaagatgtt gtacaacaga cgaatgaatt gattagaact     120
ttaaatggaa atgtttttca tactggtggc attggaacac agcctcagaa agagtggaat     180
tttcagctgc cacaattggg tacaacttta ttaaatttag atgataatta tgttcaatca     240
```

```
actagaggca taattgattt tttatcatct tttatagaag ctgtatgtga tgatgaaatt    300
gttagagaag cttcaagaaa tggtatgcaa cctcaatcac cagctcttat attattatct    360
tcatcaaagt ttaaaacaat taattttaat aatagttctc aatccattaa aaattggaat    420
gctcaatcaa gacgtgagaa tcctgtatat gagtataaaa atccaatgtt gtttgaatat    480
aaaaattcgt atattttaca acgcgcaaat ccacaatttg gaagcgtcat gggtttaaga    540
tactatacaa caagtaatac ttgtcaaatt gcagcatttg attccacctt agctgaaaat    600
gcaccaaaca atacacaacg tttcgtttat aatggcagac taaaaagacc catatcaaac    660
gttttaatga aaattgaagc tggtgctcca aatataagca acccaactat tttacctgat    720
cctaataatc aaacaacttg gctatttaat ccggtacaat aatgaatgg aacatttacc    780 attgaattct ataataatgg tcaactaatt gatatggttc gaaatatggg aatagttact    840
gtaagaactt ttgattctta tagaataaca attgacatga ttagaccagc tgctatgact    900
caatacgttc aacgaatctt tccacaaggt ggaccttatc attttcaggc tacatatatg    960
ttaacattaa gtatattaga tgctaccaca gagtccgttc tatgtgattc tcattcagtg   1020
gaatattcaa tagtagcaaa cgttagaaga gattcagcga tgccaactgg aactgttttt   1080
caaccgggat ttccatggga acacacacta tccaattaca ctgttgctca agaagataat   1140
ttagaaagat tattgttaat tgcatctgtg aagagaatgg taatg                   1185

<210> SEQ ID NO 31
<211> LENGTH: 1185
<212> TYPE: DNA
<213> ORGANISM: Human rotavirus C
<220> FEATURE:
<221> NAME/KEY: misc_feature
<223> OTHER INFORMATION: Human rotavirus group C VP6 S1 nucleotide
      sequence

<400> SEQUENCE: 31
atggatgtac tttttttctat agcgaaaacc gtgtcagatc ttaaagagaa agttgtagtt     60
ggaacaattt atactaatgt agaagatgtt gtacaacaga cgaatgaatt gattagaact    120
ttgaatggaa atattttca tactggtggc attggaacac agcctcagaa agagtggaat    180
tttcagctcc cacaatttggg taccacttta ttaaatttag atgataatta tgttcaatca    240
actagaggca taattgattt tttatcatct tttatagaag ctgtatgtga tgatgaaatt    300
gttagagaag cttcaagaaa tggtatgcaa cctcaatcac cagctcttat attattatct    360
tcatcaaaat ttaaaacaat taattttaat aatagttctc aatctatcaa aaattggaat    420
gctcaatcaa gacgtgagaa tcctgtatat gagtacaaaa atccaatgtt gtttgaatat    480
aaaaattctt atattttaca acgcgcaaat ccacaatttg gaagcgtcat gggtttaaga    540
tattatacaa caagtaatat ttgtcaaatt gcagcatttg attccaccct agctgaaaat    600
gcaccaaata atacgcaacg cttcgtttat aatggcagac taaaaagacc catatcaaat    660
gttttaatga aaatagaagc tggtgctcca aatataagca acccaactat tttacctgat    720
cctaataatc aaacaacttg gctttttaat ccggtacaat aatgaatgg aacatttacc    780 attgaattct ataataatgg tcaactaatt gatatggttc gaaatatggg aatagttact    840
gtaagaactt ttgattctta tagaataaca attgacatga ttagaccagc tgctatgact    900
caatacgttc aacgaatttt tccacaaggt ggaccttatc attttcaggc tacatatatg    960
ttaacattaa gtatattaga tgctaccaca gagtccgttc tatgtgattc tcattcagta   1020
```

```
gaatattcaa tagtagcaaa cgtcagaaga gattcagcaa tgccagctgg aactgttttt    1080
caaccgggat tccatggga acacacacta tccaattaca ctgttgctca agaagataat    1140
ttagaaagat tattgttaat cgcatctgtg aagagaatgg taatg                   1185
```

<210> SEQ ID NO 32
<211> LENGTH: 395
<212> TYPE: PRT
<213> ORGANISM: Human rotavirus C
<220> FEATURE:
<221> NAME/KEY: MISC_FEATURE
<223> OTHER INFORMATION: Human rotavirus group C VP6 S1 protein sequence

<400> SEQUENCE: 32

```
Met Asp Val Leu Phe Ser Ile Ala Lys Thr Val Ser Asp Leu Lys Glu
1               5                   10                  15

Lys Val Val Gly Thr Ile Tyr Thr Asn Val Glu Asp Val Val Gln
            20                  25                  30

Gln Thr Asn Glu Leu Ile Arg Thr Leu Asn Gly Asn Ile Phe His Thr
        35                  40                  45

Gly Gly Ile Gly Thr Gln Pro Gln Lys Glu Trp Asn Phe Gln Leu Pro
    50                  55                  60

Gln Leu Gly Thr Thr Leu Leu Asn Leu Asp Asp Asn Tyr Val Gln Ser
65                  70                  75                  80

Thr Arg Gly Ile Ile Asp Phe Leu Ser Ser Phe Ile Glu Ala Val Cys
                85                  90                  95

Asp Asp Glu Ile Val Arg Glu Ala Ser Arg Asn Gly Met Gln Pro Gln
            100                 105                 110

Ser Pro Ala Leu Ile Leu Leu Ser Ser Ser Lys Phe Lys Thr Ile Asn
        115                 120                 125

Phe Asn Asn Ser Ser Gln Ser Ile Lys Asn Trp Asn Ala Gln Ser Arg
    130                 135                 140

Arg Glu Asn Pro Val Tyr Glu Tyr Lys Asn Pro Met Leu Phe Glu Tyr
145                 150                 155                 160

Lys Asn Ser Tyr Ile Leu Gln Arg Ala Asn Pro Gln Phe Gly Ser Val
                165                 170                 175

Met Gly Leu Arg Tyr Tyr Thr Thr Ser Asn Ile Cys Gln Ile Ala Ala
            180                 185                 190

Phe Asp Ser Thr Leu Ala Glu Asn Ala Pro Asn Thr Gln Arg Phe
        195                 200                 205

Val Tyr Asn Gly Arg Leu Lys Arg Pro Ile Ser Asn Val Leu Met Lys
    210                 215                 220

Ile Glu Ala Gly Ala Pro Asn Ile Ser Asn Pro Thr Ile Leu Pro Asp
225                 230                 235                 240

Pro Asn Asn Gln Thr Thr Trp Leu Phe Asn Pro Val Gln Leu Met Asn
                245                 250                 255

Gly Thr Phe Thr Ile Glu Phe Tyr Asn Asn Gly Gln Leu Ile Asp Met
            260                 265                 270

Val Arg Asn Met Gly Ile Val Thr Val Arg Thr Phe Asp Ser Tyr Arg
        275                 280                 285

Ile Thr Ile Asp Met Ile Arg Pro Ala Ala Met Thr Gln Tyr Val Gln
    290                 295                 300

Arg Ile Phe Pro Gln Gly Gly Pro Tyr His Phe Gln Ala Thr Tyr Met
305                 310                 315                 320

Leu Thr Leu Ser Ile Leu Asp Ala Thr Thr Glu Ser Val Leu Cys Asp
                325                 330                 335
```

Ser His Ser Val Glu Tyr Ser Ile Val Ala Asn Val Arg Arg Asp Ser
            340                 345                 350

Ala Met Pro Ala Gly Thr Val Phe Gln Pro Gly Phe Pro Trp Glu His
            355                 360                 365

Thr Leu Ser Asn Tyr Thr Val Ala Gln Glu Asp Asn Leu Glu Arg Leu
            370                 375                 380

Leu Leu Ile Ala Ser Val Lys Arg Met Val Met
385                 390                 395

<210> SEQ ID NO 33
<211> LENGTH: 1063
<212> TYPE: DNA
<213> ORGANISM: Human rotavirus C
<220> FEATURE:
<221> NAME/KEY: misc_feature
<223> OTHER INFORMATION: Human rotavirus group C VP7 S1 nucleotide
      sequence

<400> SEQUENCE: 33
ggcatttaaa aaagaagaag ctgtctgaca aactggtctt cttttttaaat ggtttgtaca      60 acattgtaca ctgtttgcgc cattctcttc attcttttca tttatatatt attatttaga     120
aaaatgttcc acctaataac tgatacttta atagtgatgc ttattttatc taattgtgta     180
gagtggtcac aaggtcagat gtttattgat gatatacatt ataatggtaa cgttgagact     240
atcataaatt ctactgatcc ttttaatgtt gaatctttat gtatttattt tccaaatgca     300
gttgtaggat cacagggacc aggtaaatcc gatggacatt tgaatgatgg taattatgca     360
cagactatcg ccactttgtt tgaaacaaaa ggattcccaa aaggttcaat ataattaaa      420 acatatacac agacatcaga ctttataaat tcagtagaaa tgacatgctc ttataatata     480
gttatcattc ctgatagccc aaatgattca gaatctattg aacagatagc agaatggatt     540
ttaaatgttt ggagatgtga tgacatgaat ttggaaattt atacttatga acaaattgga     600
ataaacaatt tatgggctgc atttggtagt gactgtgata tatctgtctg tccattagat     660
actacaagta atggaatcgg atgttcacca gctagtacag aaacttatga agttgtatca     720
aatgacaccc aattggcctt aattaatgtt gtggataatg ttagacatag aatacagatg     780
aacactgctc aatgtaaatt gaaaaattgt attaagggtg aagctcgact gaatactgca     840
ctaataagaa tttcaacatc atcaagtttt gataattcat tgtcaccatt aaataacggc     900
caaacaacaa gatcgtttaa aataaatgca agaaatggt ggactatatt ttatacaata     960
attgattata ttaatacaat tgtacaatca atgactccca gacatcgggc gatttatcca    1020
gaagggtgga tgttgaggta tgcgtaaaca agatcatgtg gct                      1063

<210> SEQ ID NO 34
<211> LENGTH: 332
<212> TYPE: PRT
<213> ORGANISM: Human rotavirus C
<220> FEATURE:
<221> NAME/KEY: MISC_FEATURE
<223> OTHER INFORMATION: Human rotavirus group C VP7 S1 nucleotide
      sequence
<220> FEATURE:
<221> NAME/KEY: MISC_FEATURE
<223> OTHER INFORMATION: Human rotavirus group C VP7 S1 protein
      sequence

<400> SEQUENCE: 34

Met Val Cys Thr Thr Leu Tyr Thr Val Cys Ala Ile Leu Phe Ile Leu
1               5                   10                  15

-continued

```
Phe Ile Tyr Ile Leu Leu Phe Arg Lys Met Phe His Leu Ile Thr Asp
            20                  25                  30
Thr Leu Ile Val Met Leu Ile Leu Ser Asn Cys Val Glu Trp Ser Gln
        35                  40                  45
Gly Gln Met Phe Ile Asp Asp Ile His Tyr Asn Gly Asn Val Glu Thr
    50                  55                  60
Ile Ile Asn Ser Thr Asp Pro Phe Asn Val Glu Ser Leu Cys Ile Tyr
65                  70                  75                  80
Phe Pro Asn Ala Val Val Gly Ser Gln Gly Pro Gly Lys Ser Asp Gly
                85                  90                  95
His Leu Asn Asp Gly Asn Tyr Ala Gln Thr Ile Ala Thr Leu Phe Glu
            100                 105                 110
Thr Lys Gly Phe Pro Lys Gly Ser Ile Ile Lys Thr Tyr Thr Gln
        115                 120                 125
Thr Ser Asp Phe Ile Asn Ser Val Glu Met Thr Cys Ser Tyr Asn Ile
    130                 135                 140
Val Ile Ile Pro Asp Ser Pro Asn Asp Ser Glu Ser Ile Glu Gln Ile
145                 150                 155                 160
Ala Glu Trp Ile Leu Asn Val Trp Arg Cys Asp Asp Met Asn Leu Glu
                165                 170                 175
Ile Tyr Thr Tyr Glu Gln Ile Gly Ile Asn Asn Leu Trp Ala Ala Phe
            180                 185                 190
Gly Ser Asp Cys Asp Ile Ser Val Cys Pro Leu Asp Thr Thr Ser Asn
        195                 200                 205
Gly Ile Gly Cys Ser Pro Ala Ser Thr Glu Thr Tyr Glu Val Val Ser
    210                 215                 220
Asn Asp Thr Gln Leu Ala Leu Ile Asn Val Val Asp Asn Val Arg His
225                 230                 235                 240
Arg Ile Gln Met Asn Thr Ala Gln Cys Lys Leu Lys Asn Cys Ile Lys
                245                 250                 255
Gly Glu Ala Arg Leu Asn Thr Ala Leu Ile Arg Ile Ser Thr Ser Ser
            260                 265                 270
Ser Phe Asp Asn Ser Leu Ser Pro Leu Asn Asn Gly Thr Thr Arg
        275                 280                 285
Ser Phe Lys Ile Asn Ala Lys Lys Trp Trp Thr Ile Phe Tyr Thr Ile
    290                 295                 300
Ile Asp Tyr Ile Asn Thr Ile Val Gln Ser Met Thr Pro Arg His Arg
305                 310                 315                 320
Ala Ile Tyr Pro Glu Gly Trp Met Leu Arg Tyr Ala
                325                 330
```

<210> SEQ ID NO 35
<211> LENGTH: 395
<212> TYPE: PRT
<213> ORGANISM: Human rotavirus C
<220> FEATURE:
<221> NAME/KEY: MISC_FEATURE
<223> OTHER INFORMATION: Human rotavirus group C VP6 Bristol protein
   sequence

<400> SEQUENCE: 35

```
Met Asp Val Leu Phe Ser Ile Ala Lys Thr Val Ser Asp Leu Lys Lys
1               5                   10                  15
Lys Val Val Gly Thr Ile Tyr Thr Asn Val Glu Asp Val Val Gln
            20                  25                  30
```

```
Gln Thr Asn Glu Leu Ile Arg Thr Leu Asn Gly Asn Ile Phe His Thr
         35                  40                  45

Gly Gly Ile Gly Thr Gln Pro Gln Lys Glu Trp Asn Phe Gln Leu Pro
 50                  55                  60

Gln Leu Gly Thr Thr Leu Leu Asn Leu Asp Asp Asn Tyr Val Gln Ser
 65                  70                  75                  80

Thr Arg Gly Ile Ile Asp Phe Leu Ser Ser Phe Ile Glu Ala Val Cys
                 85                  90                  95

Asp Asp Glu Ile Val Arg Glu Ala Ser Arg Asn Gly Met Gln Pro Gln
             100                 105                 110

Ser Pro Ala Leu Ile Leu Leu Ser Ser Lys Phe Lys Thr Ile Asn
             115                 120                 125

Phe Asn Asn Ser Ser Gln Ser Ile Lys Asn Trp Asn Ala Gln Ser Arg
 130                 135                 140

Arg Glu Asn Pro Val Tyr Glu Tyr Lys Asn Pro Met Leu Phe Glu Tyr
145                 150                 155                 160

Lys Asn Ser Tyr Ile Leu Gln Arg Ala Asn Pro Gln Phe Gly Ser Val
                 165                 170                 175

Met Gly Leu Arg Tyr Tyr Thr Thr Ser Asn Thr Cys Gln Ile Ala Ala
             180                 185                 190

Phe Asp Ser Thr Leu Ala Glu Asn Ala Pro Asn Asn Thr Gln Arg Phe
 195                 200                 205

Val Tyr Asn Gly Arg Leu Lys Arg Pro Ile Ser Asn Val Leu Met Lys
     210                 215                 220

Ile Glu Ala Gly Ala Pro Asn Ile Ser Asn Pro Thr Ile Leu Pro Asp
225                 230                 235                 240

Pro Asn Asn Gln Thr Thr Trp Leu Phe Asn Pro Val Gln Leu Met Asn
                 245                 250                 255

Gly Thr Phe Thr Ile Glu Phe Tyr Asn Asn Gly Gln Leu Ile Asp Met
             260                 265                 270

Val Arg Asn Met Gly Ile Val Thr Val Arg Thr Phe Asp Ser Tyr Arg
 275                 280                 285

Ile Thr Ile Asp Met Ile Arg Pro Ala Ala Met Thr Gln Tyr Val Gln
     290                 295                 300

Arg Ile Phe Pro Gln Gly Gly Pro Tyr His Phe Gln Ala Thr Tyr Met
305                 310                 315                 320

Leu Thr Leu Ser Ile Leu Asp Ala Thr Thr Glu Ser Val Leu Cys Asp
                 325                 330                 335

Ser His Ser Val Glu Tyr Ser Ile Val Ala Asn Val Arg Arg Asp Ser
             340                 345                 350

Ala Met Pro Ala Gly Thr Val Phe Gln Pro Gly Phe Pro Trp Glu His
 355                 360                 365

Thr Leu Ser Asn Tyr Thr Val Ala Gln Glu Asp Asn Leu Glu Arg Leu
     370                 375                 380

Leu Leu Ile Ala Ser Val Lys Arg Met Val Met
385                 390                 395

<210> SEQ ID NO 36
<211> LENGTH: 395
<212> TYPE: PRT
<213> ORGANISM: Human rotavirus C
<220> FEATURE:
<221> NAME/KEY: MISC_FEATURE
<223> OTHER INFORMATION: Human rotavirus group C VP6 Jajeri protein
      sequence
```

<400> SEQUENCE: 36

```
Met Asp Val Leu Phe Ser Ile Ala Lys Thr Val Ser Asp Leu Lys Lys
1               5                   10                  15
Lys Val Val Gly Thr Ile Tyr Thr Asn Val Glu Asp Val Val Gln
            20                  25                  30
Gln Thr Asn Glu Leu Ile Arg Thr Leu Asn Gly Asn Ile Phe Tyr Thr
        35                  40                  45
Gly Gly Ile Gly Thr Gln Pro Gln Lys Glu Trp Asn Phe Gln Leu Pro
    50                  55                  60
Gln Leu Gly Thr Thr Leu Leu Asn Leu Asp Asp Asn Tyr Val Gln Ser
65                  70                  75                  80
Thr Arg Gly Ile Ile Asp Phe Leu Ser Ser Phe Ile Glu Ala Val Cys
                85                  90                  95
Asp Asp Glu Ile Val Arg Glu Ala Ser Arg Asn Gly Met Gln Pro Gln
            100                 105                 110
Ser Pro Ala Leu Ile Leu Leu Ser Ser Lys Phe Lys Thr Ile Asn
        115                 120                 125
Phe Asn Asn Ser Ser Gln Ser Ile Lys Asn Trp Asn Ala Gln Ser Arg
    130                 135                 140
Arg Glu Asn Pro Val Tyr Glu Tyr Lys Asn Pro Met Val Phe Glu Tyr
145                 150                 155                 160
Lys Asn Ser Tyr Ile Leu Gln Arg Ala Asn Pro Gln Phe Gly Ser Val
                165                 170                 175
Met Gly Leu Arg Tyr Tyr Thr Thr Ser Asn Thr Cys Gln Ile Ala Ala
            180                 185                 190
Phe Asp Ser Thr Leu Ala Glu Asn Ala Pro Asn Asn Thr Gln Arg Phe
        195                 200                 205
Val Tyr Asn Gly Arg Leu Lys Arg Pro Ile Ser Asn Val Leu Met Lys
    210                 215                 220
Ile Glu Ala Gly Ala Pro Asn Ile Ser Asn Pro Thr Ile Leu Pro Asp
225                 230                 235                 240
Pro Asn Asn Gln Thr Thr Trp Leu Phe Asn Pro Val Gln Leu Met Asn
                245                 250                 255
Gly Thr Phe Thr Ile Glu Phe Tyr Asn Asn Gly Gln Leu Ile Asp Met
            260                 265                 270
Val Arg Asn Met Gly Ile Val Thr Val Arg Thr Phe Asp Ser Tyr Arg
        275                 280                 285
Ile Thr Ile Asp Ile Ile Arg Pro Ala Ala Met Thr Gln Tyr Val Gln
    290                 295                 300
Arg Ile Phe Pro Gln Gly Gly Pro Tyr His Phe Gln Ala Thr Tyr Met
305                 310                 315                 320
Leu Thr Leu Ser Ile Leu Asp Ala Thr Thr Glu Ser Val Leu Cys Asp
                325                 330                 335
Ser His Ser Val Glu Tyr Ser Ile Val Ala Asn Val Arg Arg Asp Ser
            340                 345                 350
Ala Met Pro Ala Gly Thr Val Phe Gln Pro Gly Phe Pro Trp Glu His
        355                 360                 365
Thr Leu Ser Asn Tyr Thr Val Ala Gln Glu Asp Asn Leu Glu Arg Leu
    370                 375                 380
Leu Leu Ile Ala Ser Val Lys Arg Met Val Met
385                 390                 395
```

<210> SEQ ID NO 37

```
<211> LENGTH: 395
<212> TYPE: PRT
<213> ORGANISM: Human rotavirus C
<220> FEATURE:
<221> NAME/KEY: MISC_FEATURE
<223> OTHER INFORMATION: Human rotavirus group C VP6 CMH004 protein
      sequence

<400> SEQUENCE: 37
```

| |

```
Thr Leu Ser Asn Tyr Thr Val Ala Gln Glu Asp Asn Leu Glu Arg Leu
        370                 375                 380

Leu Leu Ile Ala Ser Val Lys Arg Met Val Met
385                 390                 395

<210> SEQ ID NO 38
<211> LENGTH: 395
<212> TYPE: PRT
<213> ORGANISM: Human rotavirus C
<220> FEATURE:
<221> NAME/KEY: MISC_FEATURE
<223> OTHER INFORMATION: Human rotavirus group C VP6 V508 protein
      sequence

<400> SEQUENCE: 38

Met Asp Val Leu Phe Ser Ile Ala Lys Thr Val Ser Asp Leu Lys Lys
1               5                   10                  15

Lys Val Val Val Gly Thr Ile Tyr Thr Asn Val Glu Asp Val Val Gln
                20                  25                  30

Gln Thr Asn Glu Leu Ile Arg Thr Leu Asn Gly Asn Val Phe His Thr
            35                  40                  45

Gly Gly Ile Gly Thr Gln Pro Gln Lys Glu Trp Asn Phe Gln Leu Pro
        50                  55                  60

Gln Leu Gly Thr Thr Leu Leu Asn Leu Asp Asp Asn Tyr Val Gln Ser
65                  70                  75                  80

Thr Arg Gly Ile Ile Asp Phe Leu Ser Ser Phe Ile Glu Ala Val Cys
                85                  90                  95

Asp Asp Glu Ile Val Arg Glu Ala Ser Arg Asn Gly Met Gln Pro Gln
            100                 105                 110

Ser Pro Ala Leu Ile Leu Leu Ser Ser Lys Phe Lys Thr Ile Asn
        115                 120                 125

Leu Asn Asn Ser Ser Gln Ser Ile Lys Asn Trp Asn Ala Gln Ser Arg
130                 135                 140

Arg Glu Asn Pro Val Tyr Glu Tyr Lys Asn Pro Met Leu Phe Glu Tyr
145                 150                 155                 160

Lys Asn Ser Tyr Ile Leu Gln Arg Ala Asn Pro Gln Phe Gly Ser Val
                165                 170                 175

Met Gly Leu Arg Tyr Tyr Thr Thr Ser Asn Thr Cys Gln Ile Ala Ala
            180                 185                 190

Phe Asp Ser Thr Leu Ala Glu Asn Ala Pro Asn Thr Gln Arg Phe
        195                 200                 205

Val Tyr Asn Gly Arg Leu Lys Arg Pro Ile Ser Asn Val Leu Met Lys
210                 215                 220

Ile Glu Ala Gly Ala Pro Asn Ile Ser Asn Pro Thr Ile Leu Pro Asp
225                 230                 235                 240

Pro Asn Asn Gln Thr Thr Trp Leu Phe Asn Pro Val Gln Leu Met Asn
                245                 250                 255

Gly Thr Phe Thr Ile Glu Phe Tyr Asn Asn Gly Gln Leu Ile Asp Met
            260                 265                 270

Val Arg Asn Met Gly Ile Val Thr Val Arg Thr Phe Asp Ser Tyr Arg
        275                 280                 285

Ile Thr Ile Asp Met Ile Arg Pro Ala Ala Met Thr Gln Tyr Val Gln
            290                 295                 300

Arg Ile Phe Pro Gln Gly Gly Pro Tyr His Phe Gln Ala Thr Tyr Met
305                 310                 315                 320
```

Leu Thr Leu Ser Ile Leu Asp Ala Thr Thr Glu Ser Val Leu Cys Asp
             325                 330                 335

Ser His Ser Val Glu Tyr Ser Ile Val Ala Asn Val Arg Arg Asp Ser
        340                 345                 350

Ala Met Pro Ala Gly Thr Val Phe Gln Pro Gly Phe Pro Trp Glu His
        355                 360                 365

Thr Leu Ser Asn Tyr Thr Val Ala Gln Glu Asp Asn Leu Glu Arg Leu
        370                 375                 380

Leu Leu Ile Ala Ser Val Lys Arg Met Val Met
385                 390                 395

<210> SEQ ID NO 39
<211> LENGTH: 395
<212> TYPE: PRT
<213> ORGANISM: Human rotavirus C
<220> FEATURE:
<221> NAME/KEY: MISC_FEATURE
<223> OTHER INFORMATION: Human rotavirus group C VP6 China protein
      sequence

<400> SEQUENCE: 39

Met Asp Val Leu Phe Ser Ile Ala Lys Thr Val Ser Asp Leu Lys Lys
1               5                   10                  15

Lys Val Val Gly Thr Ile Tyr Thr Asn Val Glu Asp Val Val Gln
            20                  25                  30

Gln Thr Asn Glu Leu Ile Arg Thr Leu Asn Gly Asn Ile Phe His Thr
        35                  40                  45

Gly Gly Ile Gly Thr Gln Pro Gln Lys Glu Trp Asn Phe Gln Leu Pro
50                  55                  60

Gln Leu Gly Thr Thr Leu Leu Asn Leu Asp Asp Asn Tyr Val Gln Ser
65                  70                  75                  80

Thr Arg Gly Ile Ile Asp Phe Leu Ser Ser Phe Ile Glu Ala Val Cys
                85                  90                  95

Asp Asp Glu Ile Val Arg Glu Ala Ser Arg Asn Gly Met Gln Pro Gln
            100                 105                 110

Ser Pro Ala Leu Ile Leu Leu Ser Ser Lys Phe Lys Thr Ile Asn
        115                 120                 125

Phe Asn Asn Ser Ser Gln Ser Ile Lys Asn Trp Asn Ala Gln Ser Arg
130                 135                 140

Arg Glu Asn Pro Val Tyr Glu Tyr Lys Asn Pro Met Leu Leu Glu Tyr
145                 150                 155                 160

Lys Asn Ser Tyr Ile Leu Gln Arg Ala Ile Pro Gln Phe Gly Ser Val
                165                 170                 175

Met Gly Leu Arg Tyr Tyr Thr Thr Ser Asn Thr Cys Gln Ile Ala Ala
            180                 185                 190

Phe Asp Ser Thr Leu Ala Glu Asn Ala Pro Asn Asn Thr Gln Arg Phe
        195                 200                 205

Val Tyr Asn Gly Arg Leu Lys Arg Pro Ile Ser Asn Val Leu Met Lys
210                 215                 220

Ile Glu Ala Gly Ala Pro Asn Ile Ser Asn Pro Thr Ile Leu Pro Asp
225                 230                 235                 240

Pro Asn Asn Gln Thr Thr Trp Leu Phe Asn Pro Val Gln Leu Met Asn
                245                 250                 255

Gly Thr Phe Thr Ile Glu Phe Tyr Asn Asn Gly Gln Leu Ile Asp Met
            260                 265                 270

```
Val Arg Asn Met Gly Ile Val Thr Val Arg Thr Phe Asp Ser Tyr Arg
            275                 280                 285

Ile Thr Ile Asp Met Ile Arg Pro Ala Ala Arg Thr Gln Tyr Val Gln
    290                 295                 300

Gln Ile Phe Pro Gln Gly Gly Pro Tyr His Phe Gln Ala Thr Tyr Met
305                 310                 315                 320

Leu Thr Leu Ser Ile Leu Asp Ala Thr Thr Glu Ser Val Leu Cys Asp
                325                 330                 335

Ser His Ser Val Glu Tyr Ser Ile Val Ala Asn Val Arg Arg Asp Ser
                340                 345                 350

Ala Met Pro Ala Gly Thr Val Phe Gln Pro Gly Phe Pro Trp Glu His
            355                 360                 365

Thr Leu Ser Asn Tyr Thr Val Ala Gln Glu Asp Asn Leu Glu Arg Leu
    370                 375                 380

Leu Leu Ile Ala Ser Val Lys Arg Met Val Met
385                 390                 395

<210> SEQ ID NO 40
<211> LENGTH: 395
<212> TYPE: PRT
<213> ORGANISM: Human rotavirus C
<220> FEATURE:
<221> NAME/KEY: MISC_FEATURE
<223> OTHER INFORMATION: Human rotavirus group C VP6 BCN6 protein
      sequence

<400> SEQUENCE: 40

Met Asp Val Leu Phe Ser Ile Ala Lys Thr Val Ser Asp Leu Lys Lys
1               5                   10                  15

Lys Val Val Val Gly Thr Ile Tyr Thr Asn Val Glu Asp Val Val Gln
            20                  25                  30

Gln Thr Asn Glu Leu Ile Arg Thr Leu Asn Gly Asn Val Phe His Thr
        35                  40                  45

Gly Gly Ile Gly Thr Gln Pro Gln Lys Glu Trp Asn Phe Gln Leu Pro
    50                  55                  60

Gln Leu Gly Thr Thr Leu Leu Asn Leu Asp Asp Asn Tyr Val Gln Ser
65                  70                  75                  80

Thr Arg Gly Ile Ile Asp Phe Leu Ser Ser Phe Ile Glu Ala Val Cys
                85                  90                  95

Asp Asp Glu Ile Val Arg Glu Ala Ser Arg Asn Gly Met Gln Pro Gln
            100                 105                 110

Ser Pro Ala Leu Ile Leu Leu Ser Ser Lys Phe Lys Thr Ile Asn
        115                 120                 125

Phe Asn Asn Ser Ser Gln Ser Ile Lys Asn Trp Asn Ala Gln Ser Arg
    130                 135                 140

Arg Glu Asn Pro Val Tyr Glu Tyr Lys Asn Pro Met Leu Phe Glu Tyr
145                 150                 155                 160

Lys Asn Ser Tyr Ile Leu Gln Arg Ala Asn Pro Gln Phe Gly Ser Val
                165                 170                 175

Met Gly Leu Arg Tyr Tyr Thr Thr Ser Asn Thr Cys Gln Ile Ala Ala
            180                 185                 190

Phe Asp Ser Thr Leu Ala Glu Asn Ala Pro Asn Asn Thr Gln Arg Phe
        195                 200                 205

Val Tyr Asn Gly Arg Leu Lys Arg Pro Ile Ser Asn Val Leu Met Lys
    210                 215                 220
```

Ile Glu Ala Gly Ala Pro Asn Ile Ser Asn Pro Thr Ile Leu Pro Asp
225                 230                 235                 240

Pro Asn Asn Gln Thr Thr Trp Leu Phe Asn Pro Val Gln Leu Met Asn
            245                 250                 255

Gly Thr Phe Thr Ile Glu Phe Tyr Asn Asn Gly Gln Leu Ile Asp Met
        260                 265                 270

Val Arg Asn Met Gly Ile Val Thr Val Arg Thr Phe Asp Ser Tyr Arg
    275                 280                 285

Ile Thr Ile Asp Met Ile Arg Pro Ala Ala Met Thr Gln Tyr Val Gln
290                 295                 300

Arg Ile Phe Pro Gln Gly Gly Pro Tyr His Phe Gln Ala Thr Tyr Met
305                 310                 315                 320

Leu Thr Leu Ser Ile Leu Asp Ala Thr Thr Glu Ser Val Leu Cys Asp
            325                 330                 335

Ser His Ser Val Glu Tyr Ser Ile Val Ala Asn Val Arg Arg Asp Ser
        340                 345                 350

Ala Met Pro Thr Gly Thr Val Phe Gln Pro Gly Phe Pro Trp Glu His
    355                 360                 365

Thr Leu Ser Asn Tyr Thr Val Ala Gln Glu Asp Asn Leu Glu Arg Leu
370                 375                 380

Leu Leu Ile Ala Ser Val Lys Arg Met Val Met
385                 390                 395

<210> SEQ ID NO 41
<211> LENGTH: 1185
<212> TYPE: DNA
<213> ORGANISM: Human rotavirus C
<220> FEATURE:
<221> NAME/KEY: misc_feature
<223> OTHER INFORMATION: Human rotavirus group C VP6 nucleotide
      consensus sequence

<400> SEQUENCE: 41
atggatgtac ttttttctat agcgaaaact gtgtcagatc ttaaaaagaa agttgtagtt      60
ggaacaattt atactaatgt agaagatgtt gtacaacaga cgaatgaatt gattagaact     120
ttgaatggaa atattttca tactggtggc attggaacac agcctcagaa agagtggaat     180
tttcagctac cacaattggg tacaacttta ttaaatttag atgataatta tgttcaatca     240
actagaggca taattgattt tttatcatct tttatagaag ctgtatgtga tgatgaaatt     300
gttagagaag cttcaagaaa tggtatgcaa cctcaatcac cagctcttat attattatct     360
tcatcaaaat ttaaaacaat taattttaat aatagttctc aatctatcaa aaattggaat     420
gctcaatcaa gacgtgagaa tcctgtatat gagtacaaaa atccaatgtt gtttgaatat     480
aaaaattctt atatttaca acgcgcaaat ccacaatttg gaagcgtcat gggtttaaga     540
tattatacaa caagtaatac ttgtcaaatt gcagcatttg attccaccct agctgaaaat     600
gcaccaaaca atacgcaacg cttcgtttat aatggcagac taaaaagacc catatcaaat     660 gtttttaatga aaatagaagc tggtgctcca aatataagca acccaactat tttacctgat     720
cctaataatc aaacaacttg gcttttttaat ccggtacaat taatgaatgg aacatttacc     780
attgaattct ataataatgg tcaactaatt gatatggttc gaaatatggg aatagttact     840
gtaagaactt tgattcttta gaataacaa attgacatga ttagaccagc tgctatgact     900
caatacgttc aacgaatttt tccacaaggt ggaccttatc attttcaggc tacatatatg     960
ttaacattaa gtatattaga tgctaccaca gagtccgttc tatgtgattc tcattcagta    1020

```
gaatattcaa tagtagcaaa cgtcagaaga gattcagcga tgccagctgg aactgttttt    1080
caaccgggat ttccatggga acacacacta tccaattaca ctgttgctca agaagataat    1140
ttagaaagat tattgttaat cgcatctgtg aagagaatgg taatg                    1185

<210> SEQ ID NO 42
<211> LENGTH: 2655
<212> TYPE: DNA
<213> ORGANISM: Human rotavirus C
<220> FEATURE:
<221> NAME/KEY: misc_feature
<223> OTHER INFORMATION: Human rotavirus group C strain ASP88 VP2 S1
      nucleotide sequence of open reading frame
<220> FEATURE:
<221> NAME/KEY: misc_feature
<223> OTHER INFORMATION: Human rotavirus group C strain ASP88 VP2
      nucleotide sequence of open reading frame

<400> SEQUENCE: 42
atgataagca gaaacaggcg cagaataac caacaaaaag atataggaaa agagaaacaa       60
ttagagacta taattgacaa agaagtaaag gaaaacaaag attctacaaa agaagataag     120
ctagtagtta cggaagaaag taatggtgac gtcacagctg ttaaagaaca atcgaataat     180
attaatttac aaaagaatga tttggttaaa gaagtcatga atatacagaa tcaaacatta     240
aatacagtag ttgctgagaa taaagttgaa atagaagaaa tagttaaaaa atacattccc     300
tcatataata ctgacagcct tattgttaaa agttaactg aaatccagga atcaagtgct      360
aaaacatata atacattatt cagattattt actccagtta aaagttattt atatgacata     420
aatggtgaga aaaattatc gactagatgg tattggaaat tgctcaaaga tgatttacct      480
gctggtgatt actcagttag acaattcttc ctgtcactat atttaaatgt tttagaggga     540
atgcccgatt acataatgct tcgtgatatg gcagtggata cccatattc agcagaagca     600 ggtaaaatcg tagatggaaa gtctaaagaa attttagttg aactatatca agaccaaatg     660
acagaagggt atattagaag atatatgtct gaattaagac ataaaaatatc tggagaaaca     720 aatactgcaa atatccagc tattctacat cccgtggata tgagcttaa tcaatacttt       780 cttgagcatc agttaattca accattaact acaagaaata ttgcagaatt gattccaact     840
caattatatc atgatccaaa ttacgttttt aatattgatg cagccttttt aacaaattca     900
agatttgttc caccatactt aacacaggat aggattggat acatgatgg attcgaatca     960 atatgggatt caaaaaccca tgctgattac gtttcagcta aagatttat acctgattta     1020 actgaactgg tagatgctga aaagcaaata aagaaatgg ctgcacattt acaactagag     1080
gctattacag tacaggttga atcacaattt ttagcgggaa ttagtgctgc tgcagctaat     1140
gaagcgttca aatttataat tggctcagtt ttatctacca gaacaatagc tgtagaattc     1200
ataacctcaa actatatgtc gttagcatca tgtatgtatt taatgactat tatgccatca     1260
gagattttct tgagagaatc attagttgct atgcgattag caataataaa taccccttatt   1320 tatccagctc taggtttagc gcaaatgcat tatcaagcag gtgaagtgag gacccccattc    1380 gaattagctg agatgcgagt agctaataga tctattagac aatggttaca tcattgtaat     1440
acacttcaat ttggtagaca gataacggaa gggataattc atctacgatt tactaatgat     1500
atcatgacag gtaggatagt gaacttattt tcaacaatgc tagtagcttt atcatctcag     1560
ccattcgcta catatccttt agactataaa agatctgtac aaagagcatt acaacttta     1620 tcaaatagaa cagcccaaat agcagattta accagattaa tagtatacaa ttatactaca     1680
ttatctgcat gtatagtcat gaatatgcat ttagtaggaa ctcttactgt tgaacgtata     1740
```

-continued

| | |
|---|---|
| caggccactt ctctaacttc tttaatgatg ttaatttcta ataagacagt tattccagaa | 1800 |
| ccatcgtctc ttttttcata tttctctagt aacattaatt ttcttacaaa ttataatgag | 1860 |
| caaattgata atgtggtagc agaaataatg gccgcatata gattgaattt atatcaacag | 1920 |
| aaaatgttga tgctcgttac caggtttgtg tcaaggttgt acatatttga tgctcctaaa | 1980 |
| ataccgccag atcagatgta tagattaaga aaccgattaa gaaatattcc agttgaaaga | 2040 |
| agaagagctg atgtgttcag aattattatg aataatagag atttaatcga aaaaacatca | 2100 |
| gaacgtatat gtcagggtgt gttgttatct tatacaccaa tgcctttaac ttacgttgaa | 2160 |
| gatgtcgggt taacaaatgt aattaatgac actaataact tccaaataat taatatagaa | 2220 |
| gaaattgaga agaccggtga ctattcagcc ataacgaatg cattacttcg ggatactcca | 2280 |
| attatattga aaggtgcgat tccatatgtt actaactcat cagtaattga tgttttatct | 2340 |
| aaagtggaca ccacagtgtt cgcaagcatc gtaaaagata gggatatttc aaagttaaaa | 2400 |
| ccaataaaat tcataattaa ttcagattca tccgaatatt atttagtaca caataataaa | 2460 |
| tggacaccaa caacaactac agcagtatat aaagctagat ctcagcaatt tgatatacaa | 2520 |
| cattcagtat caatgctaga gtcaaactta tttttgtgg tatataatga tttatttaaa | 2580 |
| tacattaaaa ccactacagt tctgccgata aatgctgtct cttatgatgg tgcaagaatt | 2640 |
| atgcaagaaa cataa | 2655 |

<210> SEQ ID NO 43
<211> LENGTH: 2736
<212> TYPE: DNA
<213> ORGANISM: Human rotavirus C
<220> FEATURE:
<221> NAME/KEY: misc_feature
<223> OTHER INFORMATION: Human rotavirus group C strain ASP88 VP2
      nucleotide sequence

<400> SEQUENCE: 43

| | |
|---|---|
| ggcttaaaaa gatcagtcga ggacaaatcg tccaagatga taagcagaaa caggcgcaga | 60 |
| aataaccaac aaaagatat aggaaaagag aaacaattag agactataat tgacaaagaa | 120 |
| gtaaggaaa acaaagattc tacaaaagaa gataagctag tagttacgga agaaagtaat | 180 |
| ggtgacgtca cagctgttaa agaacaatcg aataatatta atttacaaaa gaatgatttg | 240 |
| gttaaagaag tcatgaatat acagaatcaa acattaaata cagtagttgc tgagaataaa | 300 |
| gttgaaatag aagaaatagt taaaaaatac attccctcat ataatactga cagccttatt | 360 |
| gttaaaaagt taactgaaat ccaggaatca agtgctaaaa catataatac attattcaga | 420 |
| ttatttactc cagttaaaag ttatttatat gacataaatg gtgagaaaaa attatcgact | 480 |
| agatggtatt ggaaattgct caagatgat ttacctgctg gtgattactc agttagacaa | 540 |
| ttcttcctgt cactatattt aaatgtttta gagggaatgc ccgattacat aatgcttcgt | 600 |
| gatatggcag tggataaccc atattcagca gaagcaggta aaatcgtaga tggaaagtct | 660 |
| aaagaaattt tagttgaact atatcaagac caaatgacag aagggtatat tagaagatat | 720 |
| atgtctgaat taagacataa aatatctgga gaaacaaata ctgcaaaata tccagctatt | 780 |
| ctacatcccg tggataatga gcttaatcaa tactttcttg agcatcagtt aattcaacca | 840 |
| ttaactacaa gaaatattgc agaattgatt ccaactcaat tatatcatga tccaaattac | 900 |
| gttttttaata ttgatgcagc cttttttaaca aattcaagat ttgttccacc atacttaaca | 960 |
| caggatagga ttggattaca tgatggattc gaatcaatat gggattcaaa aacccatgct | 1020 |

```
gattacgttt cagctagaag atttatacct gatttaactg aactggtaga tgctgaaaag    1080
caaataaaag aaatggctgc acatttacaa ctagaggcta ttacagtaca ggttgaatca    1140
caatttttag cgggaattag tgctgctgca gctaatgaag cgttcaaatt tataattggc    1200
tcagttttat ctaccagaac aatagctgta gaattcataa cctcaaacta tatgtcgtta    1260
gcatcatgta tgtatttaat gactattatg ccatcagaga ttttcttgag agaatcatta    1320
gttgctatgc gattagcaat aataaatacc cttatttatc cagctctagg tttagcgcaa    1380
atgcattatc aagcaggtga agtgaggacc ccattcgaat tagctgagat gcgagtagct    1440
aatagatcta ttagacaatg gttacatcat tgtaatacac ttcaatttgg tagacagata    1500
acggaaggga taattcatct acgatttact aatgatatca tgacaggtag atagtgaac     1560 ttattttcaa caatgctagt agctttatca tctcagccat tcgctacata tcctttagac    1620
tataaaagat ctgtacaaag agcattacaa cttttatcaa atagaacagc ccaaatagca    1680
gatttaacca gattaatagt atacaattat actacattat ctgcatgtat agtcatgaat    1740
atgcatttag taggaactct tactgttgaa cgtatacagg ccacttctct aacttcttta    1800
atgatgttaa tttctaataa gacagttatt ccagaaccat cgtctctttt ttcatatttc    1860
tctagtaaca ttaattttct tacaaattat aatgagcaaa ttgataatgt ggtagcagaa    1920
ataatggccg catatagatt gaatttatat caacagaaaa tgttgatgct cgttaccagg    1980
tttgtgtcaa ggttgtacat atttgatgct cctaaaatac cgccagatca gatgtataga    2040
ttaagaaacc gattaagaaa tattccagtt gaaagaagaa gagctgatgt gttcagaatt    2100
attatgaata atagagattt aatcgaaaaa acatcagaac gtatatgtca gggtgtgttg    2160
ttatcttata caccaatgcc tttaacttac gttgaagatg tcgggttaac aaatgtaatt    2220
aatgacacta taacttcca aataattaat atagaagaaa ttgagaagac cggtgactat     2280
tcagccataa cgaatgcatt acttcgggat actccaatta tattgaaagg tgcgattcca    2340
tatgttacta actcatcagt aattgatgtt ttatctaaag tggacaccac agtgttcgca    2400
agcatcgtaa agatagggga tatttcaaag ttaaaaccaa taaaattcat aattaattca    2460
gattcatccg aatattattt agtacacaat aataaatgga caccaacaac aactacagca    2520
gtatataaag ctagatctca gcaatttgat atacaacatt cagtatcaat gctagagtca    2580
aacttatttt ttgtggtata taatgattta tttaaataca ttaaaaccac tacagttctg    2640
ccgataaatg ctgtctctta tgatggtgca agaattatgc aagaaacata aatgattgta    2700
tagtatcatc ttgtaacgac ctcaaactct gtggct                              2736
```

<210> SEQ ID NO 44
<211> LENGTH: 2736
<212> TYPE: DNA
<213> ORGANISM: Porcine rotavirus
<220> FEATURE:
<221> NAME/KEY: misc_feature
<223> OTHER INFORMATION: Porcine rotavirus group C strain Cowden VP2
      nucleotide sequence

<400> SEQUENCE: 44

```
ggtttaaaaa gatcaatcga ggacaaatcg tccaagatga taagcagaaa tagacgtaga     60
aacactcaac agaaagatgc tgaaaaggaa aagcagacag aaaatgtgga ggagaaagag    120
ataaaggaag ctaagaaaca agttaaagat gaaaagcaag tgattacaga agaaaacgtc    180
gatagtccta aggatgttaa agaacaatca acaccgtaa atctacaaaa aaatgactta     240 gttaagaag ttataaatat ccaaaatcaa acattgaata caatagttgc tgagaataaa     300
```

```
gtggaaattg aagaagtggt taaaaagtat attccatcat actcaactga caagctaata    360
gttaaaaaat taactgaaat tcaagaatca agtgctaaaa catacaataa attgtttaga    420
ttatttacac cggttaagag ttatctatat gatgtaaatg gagagaaaaa actatccact    480
agatggtatt ggaaactact taaagatgat ctacctgctg gtgattactc agttagacaa    540
ttctttctat ctttatactt gaatgtatta gatgaaatgc ctgattatgt tatgcttcgt    600
gatatggctg tggataatcc atattcagca gaggcaggaa aaatagtaga tgaaaaatca    660
aaagaaatcc tagtagaaat atatcaagat caaatgactg aagggtatat acggagatat    720
atgtctgatt tgagacatag aatatctggt gaaacgaata ctgctaaata tccagctatt    780
ttacatcctg tagatgaaga actaaataaa tactttcttg agcaccaact gattcaacca    840
ttgactacaa gaaatatagc agaattaatt ccaactcaat tgtatcatga tccaaattat    900
gtgtttaaca ttgatgctgc attttaaca aactcaagat ttgttccacc gtatctaaca    960
caagatagaa ttggattaca tgatggattt gagtcaattt gggatgcaaa acacatgct   1020 gattacgttt cagctagaag atttgtacct gatttaactg agttagttga tgctgaaaaa   1080
cagatgaaag aaatggcagc acatttacag cttgaagcta ttacagtgca agttgaatca   1140
caattcttgg caggaattag tgcagcggca gctaatgaag catttaagtt tataattggt   1200
actgtgctgt caactagaac aatagcagta gaattcatca catcaaatta tatgtcatta   1260
gcgtcatgta tgtatttaat gacgattatg ccatcagaaa tctttttgag agaatcgcta   1320
gttgcaatgc agttagcagt aataaatact cttacctatc cagctttagg attagcacaa   1380
atgcattatc aggcaggtga aataagaacg ccctttgaac tagcagaaat gcaagtagca   1440
aataggccca ttaggcaatg gttgcatcat tgtaatacac ttcaatttgg cagacaagta   1500
actgaaggag taacacatct acggtttaca aatgacatca tgacaggtag aatagttaat   1560
ctcttttcaa ctatgttggt agctttatca tctcagcctt ttgctacata tccattagat   1620
tacaaaagat ctgtccagag agcattacag cttctttcaa acaggactgc tcaaatagct   1680
gatttgacta gattaatagt gtacaactat acaacattgt cagcatgcat agtcatgaac   1740
atgcatttgg ttgaaccctt aactgtagaa cgtatacaag ctacagcttt aacttcactg   1800
ataatgttga tatccaataa aacggttatt ccagaaccat catccctctt ttcatacttt   1860
tctagtaata ttaatttctt gacaaactac aatgaacaga ttgataacgt agtggctgaa   1920
ataatggcag catacagact agatctatat caacagaaaa tgctaatgct tgttactcga   1980
tttgtttcac gactgtacat atttgatgct cctaagatac caccagacca gatgtataga   2040
ttaagaaata gactgaggaa cattccagtt gaaagaagaa gagcagatgt gttcagaatc   2100
attatgaata acagagatct tatagagaaa acatcagaac gcatttgtca aggagtgtta   2160
ctatcatatt caccaatgcc attaacatat gttgaggatg ttggtttgac aaatgtggtt   2220
aatgacacta atggttttca gataataaac attgaagaaa tcgagaagac aggtgattat   2280
tcagcaatta caaacgcatt actccgtgat actccaatca tactgaaggg cgctattccg   2340
tacgttacca attcatcagt aatagatgtt ctatctaaaa tagatacaac agtgtttgcg   2400
agtatcgtta aagacagaga tatttcaaaa ttaaaaccga taaaattcac aattaattca   2460
gactcatcag aatactattt agtacacaat aataaatgga caccaacaac aacaactgct   2520
gtgtacaaag ccagatctca gcaatttaat atacaacatt cagtgtcaat gttagagtca   2580
aacttgttct ttgttgtata taatgatctg tttaagtaca tcaaaacaac tacagtatta   2640
```

| | |
|---|---:|
| ccaatcaatg ccgtgtctta tgatggtgcg agaattatgc aggaaacatg aactgattaa | 2700 |
| ttatatcatc ttgtgatgac ctcaaactct gtggct | 2736 |

<210> SEQ ID NO 45
<211> LENGTH: 999
<212> TYPE: DNA
<213> ORGANISM: Human rotavirus C
<220> FEATURE:
<221> NAME/KEY: misc_feature
<223> OTHER INFORMATION: Human rotavirus group C VP7 S1 nucleotide sequence of open reading frame

<400> SEQUENCE: 45

| | |
|---|---:|
| atggtttgta caacattgta cactgtttgc gccattctct tcattctttt catttatata | 60 |
| ttattattta gaaaaatgtt ccacctaata actgatactt aatagtgat gcttatttta | 120 |
| tctaattgtg tagagtggtc acaaggtcag atgtttattg atgatataca ttataatggt | 180 |
| aacgttgaga ctatcataaa ttctactgat ccttttaatg ttgaatcttt atgtatttat | 240 |
| tttccaaatg cagttgtagg atcacaggga ccaggtaaat ccgatggaca tttgaatgat | 300 |
| ggtaattatg cacagactat cgccactttg tttgaaacaa aaggattccc aaaaggttca | 360 |
| ataataatta aacatatac acagacatca gactttataa attcagtaga aatgacatgc | 420 |
| tcttataata tagttatcat tcctgatagc ccaaatgatt cagaatctat tgaacagata | 480 |
| gcagaatgga ttttaaatgt tggagatgt gatgacatga atttggaaat ttatacttat | 540 |
| gaacaaattg gaataaacaa tttatgggct gcatttggta gtgactgtga tatatctgtc | 600 |
| tgtccattag atactacaag taatggaatc ggatgttcac cagctagtac agaaacttat | 660 |
| gaagttgtat caaatgacac ccaattggcc ttaattaatg ttgtggataa tgttagacat | 720 |
| agaatacaga tgaacactgc tcaatgtaaa ttgaaaaatt gtattaaggg tgaagctcga | 780 |
| ctgaatactg cactaataag aatttcaaca tcatcaagtt ttgataattc attgtcacca | 840 |
| ttaaataacg gccaaacaac aagatcgttt aaaataaatg caagaaatg gtggactata | 900 |
| ttttatacaa taattgatta tattaataca attgtacaat caatgactcc cagacatcgg | 960 |
| gcgatttatc cagaagggtg gatgttgagg tatgcgtaa | 999 |

<210> SEQ ID NO 46
<211> LENGTH: 1343
<212> TYPE: DNA
<213> ORGANISM: Human rotavirus C
<220> FEATURE:
<221> NAME/KEY: misc_feature
<223> OTHER INFORMATION: Human rotavirus group C VP6 S1 nucleotide sequence

<400> SEQUENCE: 46

| | |
|---|---:|
| atctcattca caatggatgt acttttttct atagcgaaaa ccgtgtcaga tcttaaagag | 60 |
| aaagttgtag ttggaacaat ttatactaat gtagaagatg ttgtacaaca gacgaatgaa | 120 |
| ttgattagaa cttgaatgg aaatattttt cactactggt gcattggaac acagcctcag | 180 |
| aaagagtgga atttcagct cccacaattg gtaccacctt tattaaattt agatgataat | 240 |
| tatgttcaat caactagagg cataattgat ttttatcat cttttataga agctgtatgt | 300 |
| gatgatgaaa ttgttagaga agcttcaaga aatggtatgc aacctcaatc accagctctt | 360 |
| atattattat cttcatcaaa atttaaaaca attaatttta ataatagttc tcaatctatc | 420 |
| aaaaattgga atgctcaatc aagacgtgag aatcctgtat atgagtacaa aaatccaatg | 480 |
| ttgtttgaat ataaaaattc ttatattta caacgcgcaa atccacaatt tggaagcgtc | 540 |

| | |
|---|---|
| atgggtttaa gatattatac aacaagtaat atttgtcaaa ttgcagcatt tgattccacc | 600 |
| ctagctgaaa atgcaccaaa taatacgcaa cgcttcgttt ataatggcag actaaaaga | 660 |
| cccatatcaa atgttttaat gaaaatagaa gctggtgctc caaatataag caacccaact | 720 |
| attttacctg atcctaataa tcaaacaact tggcttttta atccggtaca attaatgaat | 780 |
| ggaacattta ccattgaatt ctataataat ggtcaactaa ttgatatggt tcgaaatatg | 840 |
| ggaatagtta ctgtaagaac ttttgattct tatagaataa caattgacat gattagacca | 900 |
| gctgctatga ctcaatacgt tcaacgaatt tttccacaag gtggacctta tcattttcag | 960 |
| gctacatata tgttaacatt aagtatatta gatgctacca cagagtccgt tctatgtgat | 1020 |
| tctcattcag tagaatattc aatagtagca aacgtcagaa gagattcagc aatgccagct | 1080 |
| ggaactgttt ttcaaccggg atttccatgg aacacacac tatccaatta cactgttgct | 1140 |
| caagaagata atttagaaag attattgtta atcgcatctg tgaagagaat ggtaatgtag | 1200 |
| ataagctaga agactaaaca tcttctatgc ggcctacata ccatgtagca tgaatcacga | 1260 |
| ctgggtttag tccatgctcg catagggca aatatgcatg atatggatga tccccagaag | 1320 |
| gatgaaatgt gaactatgtg gct | 1343 |

<210> SEQ ID NO 47
<211> LENGTH: 1353
<212> TYPE: DNA
<213> ORGANISM: Human rotavirus C
<220> FEATURE:
<221> NAME/KEY: misc_feature
<223> OTHER INFORMATION: Human rotavirus group C VP6 Bristol nucleotide sequence

<400> SEQUENCE: 47

| | |
|---|---|
| ggcatttaaa atctcattca caatggatgt acttttttct atagcgaaaa ctgtgtcaga | 60 |
| tcttaaaaag aaagttgtgg ttggaacaat ttatactaat gtagaagatg ttgtacaaca | 120 |
| gacgaatgaa ttgattagaa cttaaatgg aaatattttt cactactggtg gcattggaac | 180 |
| acagcctcag aaagagtgga attttcagct gccacaattg gtacaactt tattaaattt | 240 |
| agatgataat tatgttcaat caactagagg cataatcgat tttttatcat cttttataga | 300 |
| agctgtatgt gatgatgaaa ttgttagaga agcttcaaga aatggtatgc aacctcaatc | 360 |
| accagctctt atattattat cttcatcaaa atttaaaaca attaattta ataatagttc | 420 |
| tcaatctatt aaaaattgga atgctcaatc aagacgtgag atcctgtat atgagtataa | 480 |
| aaatccaatg ttgttttgaat ataaaaattc gtatatttta caacgcgcaa atccacaatt | 540 |
| tggaagcgtc atgggtttaa gatattatac aacaagtaat acttgtcaaa ttgcagcatt | 600 |
| tgattccacc ctagctgaaa atgcaccaaa caatacacaa cgcttcgttt ataatggcag | 660 |
| actaaaaga cccatatcaa acgttttaat gaaaatagaa gctggtgctc caaatataag | 720 |
| caacccaact attttacctg atcctaataa tcaaacaact tggctttta atccggtaca | 780 |
| attaatgaat ggaacattta ccattgaatt ctataataat ggtcaactaa ttgatatggt | 840 |
| tcgaaatatg ggaatagtta ctgtaagaac ttttgattct tatagaataa caattgacat | 900 |
| gattagacca gctgctatga ctcaatacgt tcaacgaatt tttccacaag gtggacctta | 960 |
| tcattttcag gctacatata tgttaacatt aagtatatta gatgctacca cagagtccgt | 1020 |
| tctatgtgat tctcattcag tggaatattc aatagtagca aacgttagaa gagattcagc | 1080 |
| gatgccagct ggaactgttt ttcaaccggg atttccatgg aacacacac tatccaatta | 1140 |

```
cactgttgct caagaagata atttagaaag attattgtta attgcatctg tgaagagaat    1200
ggtaatgtag ataagctaga gggctaaaca tcttctatgc ggcctacata ccatgtagca    1260
tgaatcacga ctgggtttag tccatgcttg catagggggca aatatgcatg atatggatga   1320
tccccagaag gatgaaatgt gaactatgtg gct                                  1353
```